(12) United States Patent
Taub et al.

(10) Patent No.: US 12,727,760 B2
(45) Date of Patent: Sep. 8, 2026

(54) MEDICAL MONITORING SYSTEMS WITH CLOUD COMMUNICATION INTERFACE

(71) Applicant: ABBOTT DIABETES CARE INC., Alameda, CA (US)

(72) Inventors: Marc B. Taub, Mountain View, CA (US); Namvar Kiaie, Danville, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 490 days.

(21) Appl. No.: 17/846,977

(22) Filed: Jun. 22, 2022

(65) Prior Publication Data

US 2022/0409052 A1 Dec. 29, 2022

Related U.S. Application Data

(60) Provisional application No. 63/214,109, filed on Jun. 23, 2021.

(51) Int. Cl.
*A61B 5/00* (2006.01)
*G16H 10/60* (2018.01)
*H04W 12/06* (2021.01)

(52) U.S. Cl.
CPC ............ *A61B 5/0022* (2013.01); *A61B 5/746* (2013.01); *G16H 10/60* (2018.01); *H04W 12/06* (2013.01)

(58) Field of Classification Search
CPC ...... A61B 5/0022; A61B 5/746; G16H 10/60; G16H 50/50; G16H 40/67; H04W 12/06
See application file for complete search history.

(56) References Cited

U.S. PATENT DOCUMENTS 4,561,443 A 12/1985 Hogrefe et al.
4,592,745 A 6/1986 Rex et al.
(Continued)

FOREIGN PATENT DOCUMENTS

CA 2690742 A1 12/2008
CA 2 766 693 9/2011
(Continued)

OTHER PUBLICATIONS

IoT_Based_Real-Time_Remote_Patient_Monitoring_System (Year: 2020).*

(Continued)

*Primary Examiner* — Philip J Chea
*Assistant Examiner* — Jasmine Mochen Day
(74) *Attorney, Agent, or Firm* — ONE LLP

(57) ABSTRACT

Embodiments described herein include a medical monitoring system with a cloud communication interface in which individual components of the medical monitoring system, including medical sensors and data receiving devices are configured to communicate with remote cloud servers of the medical monitoring system using cellular networks. The remote cloud servers process medical data reported by the medical sensors and deliver data to the data receiving devices. The components of the medical monitoring system are low-cost and durable. The sensors are considered disposable after the expiration of their active use lifetime. The data receiving device can be manufactured using low-cost durable components to be protected against loss caused by accidental damage, destruction, or misplacement. Embodiments described herein further provide for authentication and for secure communication among the components of the medical monitoring system.

9 Claims, 8 Drawing Sheets

(56) References Cited

U.S. PATENT DOCUMENTS 4,627,445 A 12/1986 Garcia et al.
4,924,879 A 5/1990 O'Brien
5,267,963 A 12/1993 Bachynsky
5,318,583 A 6/1994 Rabenau et al.
5,390,671 A 2/1995 Lord et al.
5,391,250 A 2/1995 Cheney, II et al.
5,407,431 A 4/1995 Botich et al.
5,482,473 A 1/1996 Lord et al.
5,584,813 A 12/1996 Livingston et al.
5,626,566 A 5/1997 Petersen et al.
5,690,119 A 11/1997 Rytky et al.
5,786,439 A 7/1998 Van Antwerp et al.
5,865,804 A 2/1999 Bachynsky
5,954,643 A 9/1999 VanAntwerp et al.
5,971,941 A 10/1999 Simons et al.
6,093,172 A 7/2000 Funderburk et al.
6,096,268 A 8/2000 Inbar
6,103,033 A 8/2000 Say et al.
6,106,484 A 8/2000 Terwilliger et al.
6,149,626 A 11/2000 Bachynsky et al.
6,175,752 B1 1/2001 Say et al.
6,237,394 B1 5/2001 Harris et al.
6,259,181 B1 7/2001 Kawano et al.
6,283,982 B1 9/2001 Levaughn et al.
6,293,924 B1 9/2001 Safabash et al.
6,293,925 B1 9/2001 Safabash et al.
6,377,829 B1 4/2002 Al-Ali
6,424,847 B1 7/2002 Mastrototaro et al.
6,424,874 B1 7/2002 Mastrototaro et al.
6,560,471 B1 5/2003 Heller et al.
6,565,509 B1 5/2003 Say et al.
6,579,690 B1 6/2003 Bonnecaze et al.
6,607,543 B2 8/2003 Purcell et al.
6,637,611 B2 10/2003 Luch
6,641,533 B2 11/2003 Causey, III et al.
6,689,056 B1 2/2004 Kilcoyne et al.
6,695,860 B1 2/2004 Ward et al.
6,809,653 B1 10/2004 Mann et al.
6,850,859 B1 2/2005 Schuh
6,931,327 B2 * 8/2005 Goode, Jr. ........... A61B 5/1495 702/22
6,960,192 B1 11/2005 Flaherty et al.
6,990,366 B2 1/2006 Say et al.
7,027,859 B1 4/2006 McNichols et al.
7,098,803 B2 8/2006 Mann et al.
7,110,803 B2 9/2006 Shults et al.
7,144,384 B2 12/2006 Gorman et al.
7,155,729 B1 12/2006 Andrew et al.
7,207,974 B2 4/2007 Safabash et al.
7,299,082 B2 11/2007 Feldman et al.
7,301,463 B1 11/2007 Paterno
7,324,012 B2 1/2008 Mann et al.
7,344,500 B2 3/2008 Talbot et al.
7,381,184 B2 6/2008 Funderburk et al.
7,406,105 B2 7/2008 DelMain et al.
7,481,819 B2 1/2009 Koeppel et al.
7,585,287 B2 9/2009 Bresina et al.
7,643,798 B2 1/2010 Ljung
7,699,807 B2 4/2010 Faust et al.
7,731,691 B2 6/2010 Cote et al.
7,768,408 B2 8/2010 Reggiardo et al.
7,837,633 B2 11/2010 Conway et al.
7,846,132 B2 12/2010 Gravesen et al.
7,867,244 B2 1/2011 Lathrop et al.
7,883,473 B2 2/2011 LeVaughn et al.
7,946,984 B2 5/2011 Brister et al.
8,016,774 B2 9/2011 Freeman et al.
8,028,837 B2 10/2011 Gerstle et al.
8,175,673 B2 5/2012 Say et al.
8,221,332 B2 7/2012 Robbins et al.
8,382,681 B2 2/2013 Escutia et al.
8,398,664 B2 3/2013 Lamps et al.
8,469,986 B2 6/2013 Schraga
8,515,519 B2 8/2013 Brister et al.
8,747,363 B2 6/2014 Nielsen et al.
8,750,955 B2 6/2014 Brister et al.
8,864,651 B2 10/2014 Kuyava et al.
8,945,056 B2 2/2015 Iio et al.
9,241,631 B2 1/2016 Valdes et al.
9,402,544 B2 8/2016 Yee et al.
9,474,479 B2 10/2016 Pusey et al.
9,544,313 B2 * 1/2017 Love .................. A61B 5/14532
9,566,384 B2 2/2017 Gyrn et al.
9,577,934 B2 2/2017 Gross
9,668,682 B2 6/2017 Brister et al.
9,801,541 B2 10/2017 Mensinger et al.
9,808,574 B2 11/2017 Yodfat et al.
9,996,668 B2 6/2018 Reihman et al.
10,085,640 B2 10/2018 Mensinger et al.
10,292,632 B2 5/2019 Lee et al.
10,772,547 B1 9/2020 Lee et al.
10,827,954 B2 11/2020 Hoss et al.
10,855,788 B2 12/2020 Arabo et al.
10,945,647 B2 3/2021 Mazza et al.
10,973,443 B2 4/2021 Funderburk et al.
10,980,461 B2 4/2021 Simpson et al.
11,000,213 B2 5/2021 Kamath et al.
11,013,440 B2 5/2021 Lee et al.
11,017,058 B1 * 5/2021 McDavid-Arno ........................... G06F 16/2237
11,064,917 B2 7/2021 Simpson et al.
11,116,431 B1 9/2021 Harper
11,141,084 B2 10/2021 Funderburk et al.
11,202,591 B2 12/2021 Yee et al.
11,213,204 B2 1/2022 Mensinger et al.
11,298,056 B2 4/2022 Harper
2002/0022855 A1 2/2002 Bobroff et al.
2002/0161288 A1 10/2002 Shin et al.
2002/0169439 A1 11/2002 Flaherty
2002/0173703 A1 11/2002 Lebel et al.
2003/0028184 A1 2/2003 Lebel et al.
2003/0065536 A1 4/2003 Hansen et al.
2003/0100821 A1 5/2003 Heller et al.
2003/0144581 A1 7/2003 Conn et al.
2003/0153900 A1 8/2003 Aceti et al.
2003/0208113 A1 11/2003 Mault et al.
2003/0225373 A1 12/2003 Bobroff et al.
2004/0002682 A1 1/2004 Kovelman et al.
2004/0010207 A1 1/2004 Flaherty et al.
2004/0068230 A1 4/2004 Estes et al.
2004/0106860 A1 6/2004 Say et al.
2004/0117204 A1 6/2004 Mazar et al.
2004/0122353 A1 6/2004 Shahmirian et al.
2004/0133164 A1 7/2004 Funderburk et al.
2004/0186365 A1 9/2004 Jin et al.
2004/0193025 A1 9/2004 Steil et al.
2004/0204673 A1 10/2004 Flaherty
2004/0204687 A1 10/2004 Mogensen et al.
2004/0263354 A1 12/2004 Mann et al.
2005/0027463 A1 2/2005 Goode, Jr. et al.
2005/0038465 A1 2/2005 Shraga
2005/0038680 A1 2/2005 McMahon
2005/0101912 A1 5/2005 Faust et al.
2005/0101932 A1 5/2005 Cote et al.
2005/0148890 A1 7/2005 Hastings
2005/0240245 A1 10/2005 Bange et al.
2005/0242479 A1 11/2005 Petisce et al.
2005/0261563 A1 11/2005 Zhou et al.
2005/0283114 A1 12/2005 Bresina et al.
2005/0283208 A1 12/2005 Von Arx et al.
2006/0016700 A1 1/2006 Brister et al.
2006/0019327 A1 1/2006 Brister et al.
2006/0020187 A1 1/2006 Brister et al.
2006/0020189 A1 1/2006 Brister et al.
2006/0081469 A1 4/2006 Lee
2006/0094944 A1 5/2006 Chuang
2006/0095014 A1 5/2006 Ethelfeld
2006/0142651 A1 6/2006 Brister et al.
2006/0155180 A1 7/2006 Brister et al.
2006/0202859 A1 9/2006 Mastrototaro et al.
2006/0224109 A1 10/2006 Steil et al.
2006/0258959 A1 11/2006 Sode
2007/0016129 A1 1/2007 Liniger et al.
2007/0027381 A1 2/2007 Stafford

(56) References Cited

U.S. PATENT DOCUMENTS

2007/0038044 A1 2/2007 Dobbles et al.
2007/0060801 A1 3/2007 Neinast
2007/0073129 A1 3/2007 Shah et al.
2007/0093754 A1 4/2007 Mogensen et al.
2007/0093786 A1 4/2007 Goldsmith et al.
2007/0109117 A1 5/2007 Heitzmann et al.
2007/0135774 A1 6/2007 Turner et al.
2007/0142727 A1 6/2007 Zhang et al.
2007/0173708 A9 7/2007 Dobbles et al.
2007/0173710 A1 7/2007 Petisce et al.
2007/0207750 A1 9/2007 Brown et al.
2007/0219480 A1 9/2007 Kamen et al.
2007/0231846 A1 10/2007 Cosentino et al.
2007/0251835 A1 11/2007 Mehta et al.
2007/0255116 A1 11/2007 Mehta et al.
2008/0009805 A1 1/2008 Ethelfeld et al.
2008/0092638 A1 4/2008 Brenneman et al.
2008/0097246 A1 4/2008 Stafford
2008/0103447 A1 5/2008 Reggiardo et al.
2008/0114280 A1 5/2008 Stafford
2008/0119705 A1 5/2008 Patel et al.
2008/0129486 A1 6/2008 Jeckelmann et al.
2008/0154099 A1 6/2008 Aspel et al.
2008/0169904 A1 7/2008 Schulman et al.
2008/0172205 A1 7/2008 Breton et al.
2008/0214900 A1 9/2008 Fennell et al.
2008/0228045 A1 9/2008 Gao et al.
2008/0242962 A1 10/2008 Roesicke et al.
2008/0255440 A1 10/2008 Eilersen et al.
2008/0269687 A1 10/2008 Chong et al.
2008/0275313 A1 11/2008 Brister et al.
2008/0278333 A1 11/2008 Fennell et al.
2008/0281179 A1 11/2008 Fennell et al.
2008/0300476 A1 12/2008 Stafford
2008/0319414 A1 12/2008 Yodfat et al.
2009/0033482 A1 2/2009 Hayter et al.
2009/0054737 A1 2/2009 Magar et al.
2009/0076360 A1 3/2009 Brister et al.
2009/0085768 A1 4/2009 Patel et al.
2009/0099521 A1 4/2009 Gravesen et al.
2009/0124979 A1 5/2009 Raymond et al.
2009/0178459 A1 7/2009 Li et al.
2009/0198186 A1 8/2009 Mernoe et al.
2009/0216215 A1 8/2009 Thalmann et al.
2009/0237216 A1 9/2009 Twitchell, Jr.
2009/0240120 A1 9/2009 Mensinger et al.
2009/0240121 A1 9/2009 Bickoff
2009/0240128 A1 9/2009 Mensinger et al.
2009/0291634 A1 11/2009 Saarisalo
2010/0014626 A1 1/2010 Fennell et al.
2010/0045425 A1 2/2010 Chivallier
2010/0052899 A1 3/2010 Bruce
2010/0111066 A1 5/2010 Mehta
2010/0145377 A1 6/2010 Lai et al.
2010/0160759 A1 6/2010 Celentano et al.
2010/0198034 A1 8/2010 Thomas et al.
2010/0230285 A1 9/2010 Hoss et al.
2010/0268157 A1 10/2010 Wehba et al.
2010/0280782 A1 11/2010 Harper
2011/0002223 A1 1/2011 Gross
2011/0003610 A1 1/2011 Key et al.
2011/0009727 A1 1/2011 Mensinger et al.
2011/0009813 A1 1/2011 Rankers
2011/0058485 A1 3/2011 Sloan
2011/0173308 A1* 7/2011 Gutekunst .............. G16H 40/67 709/222
2011/0178378 A1 7/2011 Mernoe et al.
2011/0178717 A1 7/2011 Goodnow et al.
2011/0202495 A1 8/2011 Gawlick
2011/0210830 A1 9/2011 Talty et al.
2011/0213225 A1 9/2011 Bernstein et al.
2011/0320130 A1 12/2011 Valdes et al.
2012/0003933 A1 1/2012 Baker et al.
2012/0078071 A1* 3/2012 Bohm .................. A61B 5/0002 600/345
2012/0084053 A1 4/2012 Yuen et al.
2012/0108931 A1 5/2012 Taub et al.
2012/0233679 A1 9/2012 Shedrinsky
2012/0238851 A1 9/2012 Kamen et al.
2012/0255875 A1 10/2012 Vicente et al.
2012/0309302 A1 12/2012 Buhot
2012/0313785 A1 12/2012 Hanson et al.
2013/0127627 A1 5/2013 Hayter et al.
2014/0176338 A1 6/2014 He et al.
2015/0005601 A1 1/2015 Hoss et al.
2015/0363563 A1* 12/2015 Hallwachs ............. G16H 40/67 705/3
2016/0088428 A1* 3/2016 San Vicente ............ H04W 4/80 726/3
2017/0112531 A1 4/2017 Schoonmaker et al.
2017/0188910 A1* 7/2017 Halac ................. A61B 5/14532
2018/0182491 A1* 6/2018 Belliveau ................. A43B 3/34
2019/0216373 A1 7/2019 Harper
2019/0336055 A1* 11/2019 Shah ................. H04W 52/0232
2020/0037939 A1* 2/2020 Castagna ............. A61B 5/0004
2020/0375457 A1* 12/2020 Van Tassel ............ H04W 76/14
2021/0377726 A1* 12/2021 Finney .................. H04W 12/08
2022/0031947 A1* 2/2022 Onesti ................. A61M 5/1723
2022/0160309 A1* 5/2022 Poltorak .............. A61B 5/7264

FOREIGN PATENT DOCUMENTS

CA 2 766 685 12/2011
DE 20 2015 010 002 U1 12/2022
EP 2 407 094 1/2012
EP 2498196 A2 9/2012
EP 1789116 5/2013
EP 3 831 282 3/2022
EP 2939158 3/2022
EP 3730045 3/2022
WO WO 97/18639 A1 5/1997
WO WO 99/58190 11/1999
WO WO 00/62664 A1 10/2000
WO WO 2001/17875 3/2001
WO WO 02/15778 2/2002
WO WO 2002/058537 8/2002
WO WO 02/071305 A2 9/2002
WO WO 03/026728 4/2003
WO WO 2004/006982 1/2004
WO WO 2004/098682 11/2004
WO WO 2005/011779 2/2005
WO WO 2005/018450 3/2005
WO WO 2005/046780 5/2005
WO WO 2006/040083 4/2006
WO WO 2006/094513 9/2006
WO WO 2006/121921 11/2006
WO WO 2007/097754 8/2007
WO WO 2008/065646 A1 6/2008
WO WO 2008/073813 6/2008
WO WO 2008/114223 9/2008
WO WO 2008/115409 9/2008
WO WO 2008/155377 12/2008
WO WO 2008/157821 A1 12/2008
WO WO 2009/001347 12/2008
WO WO 2009/005952 1/2009
WO WO 2009/007287 1/2009
WO WO 2009/035773 3/2009
WO WO 2009/039013 3/2009
WO WO 2009/051832 A1 4/2009
WO WO 2009/066288 5/2009
WO WO 2009/105709 A1 8/2009
WO WO 2012/154286 A1 11/2012
WO WO 2013/019225 A1 2/2013
WO WO 2013/090791 A1 6/2013
WO WO 2014/105631 A2 7/2014

OTHER PUBLICATIONS

Medical_system_based_on_wireleless_sensors_for_real_time_remote_monitoring_of_people_with_disabilities (Year: 2017).*
SemanMedical_a_kind_of_semantic_medical_monitoring_system_model_based_on_the_IoT_sensors (Year: 2012).*

(56) References Cited

OTHER PUBLICATIONS

Zigbee_technology_for_designing_and_implementing_a_remote_medical_monitoring_system (Year: 2010).*
Abbott Press Release—Abbott Receives CE Mark for FreeStyle® Libre, A Revolutionary Glucose Monitoring System for People with Diabetes—https://abbott.mediaroom.com/2014-09-03-Abbott-Receives-CE-Mark-for-FreeStyle-Libre-a-Revolutionary-Glucose-Monitoring-System-for-People-with, Abbott, 5 pages (2014).
Breton, et al., "Optimum Subcutaneous Glucose Sampling and Fourier Analysis of Continuous Glucose Monitors," Journal of Diabetes Science and Technology, vol. 2, Issue 3, 495-500 (May 2008).
Continuous Glucose Monitoring Systems, Product Reference Guide, Diabetes Health Magazine, Dec. 2006-Jan. 2007, 3 pages.
Das, et al., "Review—Electrochemistry and Other Emerging Technologies for Continuous Glucose Monitoring Devices", ECS Sensors Plus, 20 pages (2022).
Dexcom G6, Continuous Glucose Monitoring System, User Guide, Dexcom, Inc., 346 pages (2022).
Diabetes Forecast, "Continuous Glucose Monitors for Kids," Practical Living, 10 pages (Aug. 2007).
Englert, et al., "Skin and Adhesive Issues With Continuous Glucose Monitors: A Sticky Situation", Journal of Diabetes Science and Technology, 8(4):745-751 (2014).
File History of U.S. Pat. No. 10,194,844, issued Feb. 5, 2019, 151 pages.
File History of U.S. Pat. No. 11,013,431, issued May 25, 2021, 212 pages.
File History of U.S. Pat. No. 11,116,431, issued Sep. 14, 2021, 168 pages.
File History of U.S. Pat. No. 8,483,967, issued Jul. 9, 2013, 140 pages.
File History of U.S. Pat. No. 9,310,230, issued Apr. 12, 2016, 214 pages.
U.S. Appl. No. 13/071,487, filed Mar. 24, 2011, 132 pages.
U.S. Appl. No. 13/071,497, filed Mar. 24, 2011, 162 pages.
U.S. Appl. No. 14/884,622, filed Oct. 15, 2015, 488 pages.
U.S. Appl. No. 17/008,630, filed Aug. 31, 2020, 484 pages.
U.S. Appl. No. 17/017,590, filed Sep. 10, 2020, 486 pages.
Freckmann, et al., "Performance Evaluation of Three Continuous Glucose Monitoring Systems: Comparison of Six Sensors per Subject in Parallel", Journal of Diabetes Science and Technology, 7(4):842-853 (2013).
Harris, et al., "Common Causes of Glucose Oxidase Instability in In Vivo Biosensing: A Brief Review", Journal of Diabetes Science and Technology, 7(4):1030-1038 (2013).
Hoss, et al., "Feasibility of Factory Calibration for Subcutaneous Glucose Sensors in Subjects With Diabetes", Journal of Diabetes Science and Technology, 8(1):89-94 (2014).
IPro™ 2, User Guide, Medtronic MiniMed, Inc., 108 pages (2010).
Medtronic, The MiniMed Paradigm® Real-Time Insulin Pump and Continuous Glucose Monitoring System, Sensor Features User Guide, https://web.archive.org/web/20071028164026/http://www.medtronicdiabetes.com/pdf/x22_sensor_features.pdf 77 pages (2007).
Nichols, et al., "Biocompatible Materials for Continuous Glucose Monitoring Devices", Chem Rev., 113(4), 44 pages (2013).
Rice, et al., "Continuous Measurement of Glucose, Facts and Challenges", Anesthesiology, 116(1):199-204 (2012).
Rigo, et al., "Cutaneous Reactions to Continuous Glucose Monitoring and Continuous Subcutaneous Insulin Infusion Devices in Type I Diabetes Mellitus", Journal of Diabetes Science and Technology, 15(4):786-791 (2021).
Rocchitta, et al., "Enzyme Biosensors for Biomedical Applications: Strategies for Safeguarding Analytical Performances in Biological Fluids", Sensors, 16(6):780, 22 pages (2016).
Seven® Plus Continuous Glucose Monitoring System, User's Guide, DexCom, Inc., 145 pages (2010).
WaybackMachine, Medtronic, User Guides, https://web.archive.org/web/20071023121553/http://www.medtronicdiabetes.com/products/insulinpumps/userguides.html, 3 pages (2007).
WaybackMachine, Medtronic, User Guides, https://web.archive.org/web/20071023121437/http://www.medtronicdiabetes.com/products/insulinpumps/userguides.html 9 pages (2007).
WaybackMachine, Medtronic, User Guides, https://web.archive.org/web/20071023121607/http://www.medtronicdiabetes.com/products/insulinpumps/userguides.html, 3 pages (2007).
WaybackMachine, Medtronic, User Guides, https://web.archive.org/web/20071009143917/http://www.medtronicdiabetes.com/products/insulinpumps/ 2 pages (2007).
WaybackMachine, Medtronic, User Guides, https://web.archive.org/web/20071009144413/http://www.medtronicdiabetes.com/index.html, 2 pages (2007).
Xu, et al., "Anti-Biofouling Strategies for Long-Term Continuous Use of Implantable Biosensors", Chemosensors, 8(3):66, 30 pages (2020).
"Abbott Receives CE Mark for Freestyle® Libre, A Revolutionary Glucose Monitoring System for People with Diabetes," 8 pages (2023).
U.S. Appl. No. 10/335,256 Specification and Drawings for "Relay device for transferring information between a sensor system and a fluid delivery system," filed Dec. 31, 2002, 88 pages.
U.S. Appl. No. 11/322,568 Specification and Drawings for "Telemetered characteristic monitor system and method of using the same," filed Dec. 30, 2005, 50 pages.
Armstrong, "Wireless connectivity for health and sports monitoring: a review," Br J Sports Med, 41:285-289 (2007).
ATTD Program, 4 pages (2009).
Boise, Interview with Dexcom CEO, Dexcom CEO Kevin Sayer Explains G6, 9 pages (2018).
Breton et al., "Optimum Subcutaneous Glucose Sampling and Fourier," Journal of Diabetes Science and Technology, vol. 2, Issue 3, 495-500, May 2008.
Buckingham et al., "Real-time continuous glucose monitoring," Curr Opinion Endocrinology, Diabetes & Obesity, 14:288-295 (2007).
Buckingham, "Clinical Overview of Continuous Glucose Monitoring," Journal of Diabetes Science and Technology, vol. 2, Issue 2, 300-306 (2008).
Burge et al., "Continuous Glucose Monitoring: The Future of Diabetes Management," Diabetes Spectrum, vol. 21, No. 2, 112-119 (2008).
Choleau et al., "Calibration of a subcutaneous amperometric glucose sensor implanted for 7 days in diabetic patients Part 2. Superiority of the one-point calibration method," Biosensors and Bioelectronics 17, 647-654 (2002).
Dexcom (DXCM) Company Profile, 2017 /Q4 Earnings call transcript, 12 pages (2017).
Dexcom G6 Continuous Glucose Monitoring System User Guide, 7 pages (2020).
Email communication from Sophie Hood, Jan. 24, 2023, 6 pages.
Excerpts F. White Affidavit, Medronic MiniMed, Inc., MiniMed User Guides, 11 pages (2007).
Excerpts F. White Affidavit, Medronic MiniMed, Inc., Questions regarding MiniMed Paradigm, 94 pages (2007).
Excerpts from Diabetes Forecast, 18 pages, Nov. 2007.
FDA, Premarket Approval (PMA), 3 pages, Apr. 7, 2006.
File History, U.S. Appl. No. 09/935,827, 97 pages, filed Aug. 23, 2001.
File History, U.S. Appl. No. 10/335,256, 103 pages, filed Dec. 31, 2002.
File History, U.S. Appl. No. 11/322,568, 94 pages, filed Dec. 30, 2005.
File History, U.S. Appl. No. 11/931,363, 72 pages, filed Oct. 31, 2007.
File History, U.S. Appl. No. 12/056,651, 323 pages, filed Mar. 27, 2008.
File History, U.S. Appl. No. 12/769,635, 280 pages, filed Apr. 28, 2010.
File History, U.S. Appl. No. 13/925,694, 214 pages, filed Jun. 24, 2013.
File History, U.S. Appl. No. 15/061,774, 151 pages, filed Mar. 4, 2016.

(56) References Cited

OTHER PUBLICATIONS

File History, U.S. Appl. No. 16/228,910, 212 pages, filed Dec. 21, 2018.
File History, U.S. Appl. No. 17/245,719, 168 pages, filed Mar. 30, 2021.
File History, U.S. Appl. No. 17/411,154, 320 pages, filed Aug. 25, 2021.
Hall, Interview with Kevin Sayer, President and CEO of Dexcom About the New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, (2009).
Keenan et al., "Delays in Minimally Invasive Continuous Glucose Monitoring Devices: A Review of Current Technology," J Diabetes Sci Technol, vol. 3, Issue 5, 1207-1214 (2009).
Mastrototaro, "The MiniMed Continuous Glucose Monitoring System," Diabetes Technology & Therapeutics, vol. 2, Suppl 1, S-13-S-18 (2000).
McGarraugh, "The Chemistry of Commercial Continuous Glucose Monitors," Diatebes Technology & Theraputics, vol. 11, Suppl. 1, S-17-S-24 (2009).
News Release, "*Medtronic Receives FDA Approval for World's First Insulin Pump with Real-Time Continuous Glucose Monitoring—MiniMed Paradigm® REAL-Time System Allows Patients to Make Immediate Diabetes Management Decisions; Marks Major Step Toward an Artificial Pancreas*," The Wayback Machine—https://web.archive.org/web/20060427084431/http://wwwp.medtronic.com:80/Newsroom/NewsReleaseDetails.do?itemld=114487, 2 pages (2006).
Omnipod image, Exhibit 182, 2 pages, Sep. 22, 2022.
Pantelopoulos et al., "A Survey on Wearable Biosensor Systems for Health Monitoring," 30th Annual International IEEE EMBS Conference, Vancouver, British Columbia, Canada, Aug. 20-24, 2008, 4887-4890 (2018).
Poitout et al., "A glucose monitoring system for on line estimation in man of blood glucose concentration using a miniaturized glucose sensor implanted in the subcutaneous tissue and a wearable control unit," Diabetologia, 36: 658-663 (1993).
Ruder, "Continuous Glucose Monitors for Kids," Diabetes Forecast, 1 page, Aug. 2007.
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
S&P Global Market Intelligence "DexCom, Inc. NasdaqGS:DXCM, Company Conference Presentation," 17 pages (2021).
Sayer, CGMS Changing Diabetes Management: Kevin Sayer, DIC Interview Transcript, Featuring Steve Freed, 11 pages (2019).
Shenoi, "Introduction to Digital Signal Processing and Filter Design," Wiley & Sons, 46 pages (2006).
Smith, The Science and Engineer's Guide to Digital Signal Processing, 2nd Ed., 46 pages (1999).
Sonix, Dexcom CEO—Prime Position in Our Market—Mad Money—CNBC.mp4, 4 pages (2023).
U.S. Food & Drug Administration, "Deciding When to Submit a 510(k) for a Change to an Existing Device, Guidance for Industry and Food and Drug Administration Staff," 32 pages (2017).
U.S. Food & Drug Administration, "Deciding When to Submit a 510(k) for a Change to an Existing Device, Guidance for Industry and Food and Drug Administration Staff," 78 pages (2017).
U.S. Appl. No. 16/228,910, filed Dec. 21, 2018, 37 pages.
U.S. Appl. No. 17/245,719, filed Apr. 30, 2021, 51 pages.
U.S. Appl. No. 60/976,886, filed Oct. 2, 2007, 62 pages.
Velho et al., "In vivo calibration of a subcutaneous glucose sensor for determination of subcutaneous glucose kinetics," Diabetes, American Diabetes Association, 1 (3), pp. 227-233. hal-01179359 (1988).
Watkin, "An Introduction to Flash Glucose Monitoring," 16 pages (2013).
Abbott 2023 Annual Report, 86 pages (2023).
Abbott Press Release —"Abbott's FreeStyle Libre® is Named Best Medical Technology in Last 50 Years by the Galien Foundation", 2 pages (2022).
Abbott Press Release—"Abbott's FreeStyle® Libre 2 ICGM Cleared in U.S. for Adults and Children with Diabetes, Achieving Highest Level of Accuracy and Performance Standards", 3 pages (2020).
Abbott Press Release—"FreeStyle Libre Honored by Prix Galien", 4 pages (2019).
Abbott Press Release—"Real-World Data Show Abbott's FreeStyle Libre® Systems and GLP-1 Medicines Work Better Together for People with Type 2 Diabetes", 2 pages (2024).
Ahn, "Abbott's Euro Approved Wearable Glucose Monitor is Different than Anything on the Market", 6 pages (2014).
CDC National Diabetes Statistics Report, Nov. 29, 2023, 17 pgs.
CES 2022 Innovation Award Product, Innovation Awards Honorees, FreeStyle Libre 3 System, 1 page (2022).
Chicago Innovation Awards—Abbott Laboratories, retrieved from: https://chicagoinnovation.com/winners/abbott-laboratories/, 5 pages (2018).
Custodio et al., "A Review on Architectures and Communications Technologies for Wearable Health-Monitoring Systems," Sensors 12:13907-13946 (2012).
Deposition of Gary Fletcher, Ph.D., dated Jun. 26, 2024, 54 pages in *Abbott Diabetes Care Inc., et al.* v. *Dexcom, Inc.*, Case No. 03946-82752US01, In the United States District Court for the District of Delaware.
Dexcom G5 Mobile, Continuous Glucose Monitoring System, Quick Start Guide, Dexcom, 36 pages (2020).
Dexcom G6 CGM Users Guide, 2022, 347 pgs., Revised Nov. 2022.
Dexcom G6, Start Here, Set up Guide, Dexcom, 20 pages (2022).
Dexcom G7, Overview Webpage, retrieved from: https://www.dexcom.com/g7-cgm-system, 20 pages (2024).
Dexcom G7, User Guide, Dexcom, 196 pages (2024).
Diabetes Product Review: Abbott FreeStyle Libre Flash Glucose Monitor, DiabetesMine, 6 pages (2017).
DXCM STS-7 CGM User Guide FCC Submission, 2006, 4 pgs.
Ex Parte Reexamination Certificate for U.S. Pat. No. 10,959,654, certificate issued on Aug. 5, 2024, 2 pages.
Excerpts from the "German Health Report Diabetes 2023" of the German Diabetes Society, Nov. 14, 2022, 24 pgs. [with English translation].
Extract from the privacy notice for LibreView, Jul. 13, 2024, 7 pgs.
FreeStyle Libre 14 day, "Your FreeStyle Libre 14 day System", In-Service Guide, Abbott, 28 pages (2021).
FreeStyle Libre 2, Get Started, Your guide to the FreeStyle Libre 2 system, Abbott, 15 pages (2023).
FreeStyle Libre 3 Flash Glucose Monitoring System, Get Started with the FreeStyle Libre 3 System, Abbott, 11 pages (2023).
FreeStyle Libre FAQs, retrieved from https://www.freestyle.abbott/uk-en/support/faq/question-answer.html?q=UKFaqquestion-55#, 2 pages (2024).
Galien Golden Jubilee Webpage—https://www.galienfoundation.org/galien-golden-jubilee, 3 pages (2022).
German Innovation Award—FreeStyle Libre 2—Measure Sugar without Piercing Using a Sensor and App, 1 page (2020).
Gomez et al., "Overview and Evaluation of Bluetooth Low Energy: An Emerging Low-Power Wireless Technology," Sensors 12:11734-11753 (2012).
Gonzales, et al., "The Progress of Glucose Monitoring—A Review of Invasive to Minimally and Non-Invasive Techniques, Devices and Sensors", Sensors, 19(4):800, 45 pages (2019).
Good Design Award—2017 Good Design Award, Abbott Japan Co., Ltd., Glucose Monitoring Systems, FreeStyle Libre, 9 pages (2017).
Gough, et al., "Perspectives in Diabetes, Development of the Implantable Glucose Sensor, What Are the Prospects and Why Is It Taking So Long?", Diabetes, vol. 44, pp. 1005-1009 (1995).
Hermanides, et al., "Current Application of Continuous Glucose Monitoring in the Treatment of Diabetes", Diabetes Care, vol. 34, Supp. 2, pp. S197-S201 (2011).

(56) References Cited

OTHER PUBLICATIONS

Joseph, et al., "Glucose Sensing in the Subcutaneous Tissue: Attempting to Correlate the Immune Response with Continuous Glucose Monitoring Accuracy", Diabetes Technology & Therapeutics, vol. 20, No. 5, pp. 321-324 (2018).
Letter from the U.S. Food & Drug Administration to Dexcom, Inc. regarding the Dexcom G7 Continuous Glucose Monitoring (CGM) System, 510(k) Premarket Notification and 510(k) summary, 10 pages, Dec. 7, 2022.
LibreLinkUp User Guide, Dec. 12, 2023, 28 pgs.
Lovett, "What's Next for Dexcom? CEO, CTO Talk G6 for Inpatient Use, Expanding CGMs for Patients without Diabetes", Global Edition, Digital Health, 17 pages (2020).
Medical Design Excellence Awards®, "27 Winners Announced at the 19$^{th}$ Annual Medical Design Excellence Awards (MDEA) Award Ceremony", 4 pages (2017).
Mosa et al., "A Systemic Review of Healthcare Applications for Smartphones," BMC Medical Informatics and Decision Making 12:67 (2012) 32 pgs.
News Release—Abbott—"BinaxNOW, FreeStyle Libre 2 Win Big Innovation Honors", 6 pages (2021).
News Release—Abbott Ireland—"Abbott's FreeStyle Libre Flash Glucose Monitoring System Wins the IMSTA Most Innovative Product Multi-National Award 2017", 2 pages (2017).
News Release—Business Intelligence Group—"55 Chosen as Winners in Annual Big Innovation Awards", 3 pages (2018).
News Release—Edison Awards—"Edison Awards Announces 2016 Gold, Silver, and Bronze Awards Winners", 9 pages (2016).
Not Just a Patch, Dexcom G7 Release: The Most Exciting New Features, "Dexcom G7: These are the Most Exciting Features", 14 pages (2024).
Padgette et al., "Guide to Bluetooth Security, Recommendations of the National Institute of Standards and Technology," NIST Special Publication 800-121, Revision 1, National Institute of Standards and Technology, U.S. Department of Commerce, 48 pages (2012).
Press Release—"Abbott's FreeStyle Libre® 3 Receives U.S. FDA Clearance—Features World's Smallest, Thinnest and Most Accurate 14-Day Glucose Sensor", 3 pages (2022).
Press Release—"Abbott's FreeStyle® Libre 14 Day Flash Glucose Monitoring System Now Approved in U.S.", 2 pages (2018).
The Edison Awards—About Us, Recognizing Global Innovation Excellence, 3 pages (2024).
The Edison Awards—Edison Best New Product Awards, 2022 Winners, 52 pages (2022).
The Edison Awards—Edison Best New Product Awards™, 2021 Winners, 19 pages (2024).
UPC Court of Appeal, Feb. 26, 2024, 335/2023, 38 pgs.
Van den Boom, et al., "Changes in the utilization of blood glucose test strips among patients using intermittent-scanning continuous glucose monitoring in Germany", Diabetes Obes Metab., 22:922-928 (2020).
U.S. Appl. No. 17/847,001 (2022/0409053 A1), filed Jun. 22, 2022 (Dec. 29, 2022).
Dowla, "The Basics of Radio Frequency Identification (RFID) Technology", Handbook of RF & Wireless Technologies, Chapter 14, 44 pages (2004).
Evans, et al., "Clinical temperature acquisition using proximity telemetry", J. Biomed. Eng., 13:83-86 (1991).
Finkenzeller, "RFID Handbook: Fundamentals and Applications in Contactless Smart Cards and Identification", Second Edition, 114 pages (2003).
Heller, et al., "Electrochemical Glucose Sensors and Their Applications in Diabetes Management", Chemical Reviews, 108(7):2482-2505 (2008).
Lee, "RFID Coil Design", Microchip Technology Inc., DS00678B, pp. 1-19 (1998).
Liang, et al., "An implantable bi-directional wireless transmission system for transcutaneous biological signal recording", Physiological Measurement, 26:83-97 (2005).
Radio Frequency Identification RFID, Aim Inc., White Paper, Document Version 1.2, 17 pages (2001).
Sorrells, "Passive RFID Basics", Microchip Technology Inc., DS00680B, pp. 1-5 (1998).
U.S. Appl. No. 60/614,683, filed Sep. 30, 2004.
Almurashi, A.M., et al., "Emerging Diabetes Technologies: Continuous Glucose Monitors/ Artificial Pancreases" J. Indian Inst. Sci, 2023, 26 pages.
Atmel® 8-bit AVR® Microcontroller with 16K Bytes In-System Programmable Flash, Atmega169P, 2010, 395 pages.
Atmel® Product Guide, 2008, 90 pages.
Breen, C. The iPhone Pocket Guide, 6$^{th}$ Edition, 2012, 96 pages.
Cappon, G., et al., "Continuous Glucose Monitoring Sensors for Diabetes Management: A Review of Technologies and Applications" Diabetes Metabolism Journal, 2019;43:383-397.
Cather, CGM Frustrations Survey, Dexcom, dated Jun. 2020, 37 pages.
Certified Copy U.S. Pat. No. 11,000,216, issued on May 11, 2021, 86 pages.
Clinical Trials Competitor and Ecosystem Players, Abbott, dated Jun. 25, 2020, 29 pages.
Declaration of Karl R. Leinsing, MSME, PE, in Support of Abbott's Motion for Summary Judgment, executed on May 19, 2023, 81 pages.
Declaration of Lane Desborough, 2024, 150 pages.
DeSalvo, D. et al., "Remote Glucose Monitoring in Camp Setting Reduces the Risk of Prolonged Nocturnal Hypoglycemia" Diabetes Technology & Therapeutics, vol. 16, No. 1, 2014, p. 1-10.
Design Concepts, Project Status Update for Glucose Sensor Applicator, Dexcom, dated Apr. 21, 2014, 6 pages.
Dexcom® User Guide for Dexcom G5® Mobile Continuous Glucose Monitoring (CGM) System, 2016, 372 pages.
Dexcom™STS™-7 Continuous Glucose Monitoring System, Transmitter model No. 9400-02, 2006, 3 pages.
Email from Christopher Dougherty with slides re. Global Commercial Insights Meeting, Abbott, sent on Dec. 17, 2019 (69 pages).
File History of U.S. Pat. No. 9,801,541, Issued Oct. 31, 2017 (part 1-4).
File History of U.S. Pat. No. 11,213,204, Issued Jan. 4, 2022.
FreeStyle Libre 2 HCP Pulse, Mar. 2021 Report, Abbott, dated Apr. 13, 2021, 14 pages.
FreeStyle Libre 3 Continuous Glucose Monitoring System, User's Manual, 2023, 248 pages.
Garg, S.K., et al., "Flash Glucose Monitoring: The Future is Here" Diabetes Technology & Therapeutics, vol. 19, Supplement 2, 2017, 3 pages.
Hirsch, I.B, et al., "Role of Continuous Glucose Monitoring in Diabetes Treatment" American Diabetes Association, Abbott, 2018, 28 pages.
Keith-Hynes, P., et al., "The Diabetes Assistant: A Smartphone-Based System for Real-Time Control of Blood Glucose" Electronics, 2014, pp. 609-623.
McDaniels, D., et al., "Remote Management of Cardiac Patients: The Forefront of a New Standard" Modern Healthcare, 2011, 6 pages.
MySentry™ User Guide, Medtronic Minimed, 2010, 80 pages.
National Diabetes Statistics Report, Estimates of Diabetes and Its Burden in the United States, 2023, 15 pages.
Paradigm® REAL-Time Revel™ Insulin Pump User Guide, Medtronic Minimed, 2009, 179 pages.
Place, J., et al., "DiAs Web Monitoring: A. Real-Time Remote Monitoring System Designed for Artificial Pancreas Outpatient Trials" Journal of Diabetes Science and Technology, vol. 7, No. 6, 2013, pp. 1427-1435.
Press Release, Medtronic, "Medtronic Launches First-of-Its Kind mySentry™ Remote Glucose Monitor" 2012, 8 pages.
Seagrove Partners, Globeview™, International Diabetes Device 2022 Blue Book, 143 pages.
Seven®+Plus continuous glucose monitoring system, Users Guide, Dexcom, 2010, 144 pages.
The Minimed Paradigm® REAL-Time Insulin Pump and Continuous Glucose Monitoring System, Insulin Pump User Guide, Medtronic, 2007, 180 pages.

(56) References Cited

OTHER PUBLICATIONS

Wettlaufer, G., "Merlin.Net Automation of External Reports Verification Process" 2010, 53 pages.
Declaration of Brian D. Gross, 150 pages (2023).
Declaration of Morten O. Jensen, Ph.D., Dr.Med, 67 pages (2023).
DexcomG7, Start Here, Operational Manual, Dexcom, Inc. 9 pages (2022) (with an English abstract).
DexcomG7, Receiver: Start Here, Operational Manual, Dexcom, Inc., 8 pages (2022).
DexcomG7, Operational Manual, User Guide, Dexcom, Inc., 179 pages (2022) (with an English abstract).
Dexcom, Inserting Sensor, Instructions for Use, Dexcom, Inc., 2 pages (2021).
Diabetes Forecast—The Healthy Living Magazine of the American Diabetes Association, 18 pages, Nov. 2007.
U.S. Appl. No. 17/245,719, filed Apr. 30, 2021, 168 pages.
U.S. Appl. No. 17/411,154, filed Aug. 25, 2021, 54 pages.
U.S. Appl. No. 60/587,787, filed Jul. 13, 2004, 69 pages.
Medtronic MiniMed, Inc., Fact Sheet, Features and Benefits for the MiniMed Paradigm® REAL-Time System—https://web.archive.org/web/20071030065834/http://www.medtronicdiabetes.com/pdf/dtc_features_glance.pdf, 7 pages (2007) and Affidavit of Nathaniel E Frank-White, Internet Archive, 3 pages (2023).
Medtronic MiniMed, Inc., Features for the MiniMed Paradigm® REAL-Time System, The Wayback Machine—http://www.medtronicdiabetes.com/products/insulinpumps/features/index.html, 3 pages (2007) and Affidavit of Nathaniel E Frank-White, Internet Archive, 3 pages (2023).
Medtronic MiniMed, Inc., Frequently Asked Questions About the MiniMed Paradigm® REAL-Time System, The Wayback Machine—https://web.archive.org/web/20071023121607/http://www.medtronicdiabetes.com/products/insulinpumps/features/index.html, 9 pages (2007) and Affidavit of Nathaniel E Frank-White, Internet Archive, 3 pages (2023).
Medtronic MiniMed, Inc., Request Information for the MiniMed Paradigm® REAL-Time Insulin Pump and Continuous Glucose Monitoring System, The Wayback Machine—https://web.archive.org/web/20071009144413/http://www.medtronicdiabetes.com/index.html, 3 pages (2007) and Affidavit of Nathaniel E Frank-White, Internet Archive, 3 pages (2023).
The MiniMed Paradigma® Insulin Pump and Continuous Glucose Monitoring System, Sensor Features User Guide, Paradigme® 522 and 722 Sensor Features, Medtronic MiniMed, 76 pages (2006) and Affidavit of Nathaniel E Frank-White, Internet Archive, 3 pages (2023).
U.S. Food and Drug Administration, Premarket Approval (PMA), Paradigm Real Time System, 3 pages (2006).
United States Patent and Trademark Office, Before the Patent Trial and Appeal Board, *Dexcom, Inc.* v. *Abbott Diabetes Care Inc.*, Petitioner's Explanation of Material Differences Between Petitions in U.S. Pat. No. 11,298,056 issued on Apr. 12, 2022, 8 pages (2023).
United States Patent and Trademark Office, Before the Patent Trial and Appeal Board, *Dexcom, Inc.* v. *Abbott Diabetes Care Inc.*, Petition for Inter Partes Review of U.S. Pat. No. 11,298,056 issued on Apr. 12, 2022, 132 pages (2023).
United States Patent and Trademark Office, Before the Patent Trial and Appeal Board, *Dexcom, Inc.* v. *Abbott Diabetes Care Inc.*, Notice of Filing Date Accorded to Petition and Time for Filing Patent Owner Preliminary Response in U.S. Pat. No. 11,298,056 issued on Apr. 12, 2022, 6 pages (2023).
United States Patent and Trademark Office, Before the Patent Trial and Appeal Board, *Dexcom, Inc.* v. *Abbott Diabetes Care Inc.*, Petition for Inter Partes Review of U.S. Pat. No. 11,298,056 issued on Apr. 12, 2022, 76 pages (2023).
BBC News, Technology, Bluetooth rival unveiled by Nokia, 2 pgs. (Oct. 4, 2006).
Bergenstal et al., "Effectiveness of Sensor-Augmented Insulin-Pump Therapy in Type 1 Diabetes," N Engl J Med 363:311-320 (2010).
Bloodborne pathogens, Occupational Safety and Health Admin., Labor, 29 CFR Ch. XVII (Jul. 1, 2003 Edition) § 1910.1030, pp. 260-273.
Bluetooth Specification V 2.1, Jul. 26, 2007, pp. 1-541.
Bluetooth Specification V 2.1, Jul. 26, 2007, pp. 542-906.
Dexcom STS 7 Plus User's Guide, 2011, 144 pgs.
Dexcom STS 7 User Guide, 2007, 74 pgs.
Diglas et al., "Reduced pain perception with Pen Mate™ an automatic needle insertion device for use with an insulin pen," Practical Diabetes Int 16(2):39-41 (1999).
Expert Statement of Professor Pantelis Georgiou, Aug. 9, 2024, 52 pgs.
FDA Center for Drug Evaluation and Research, Jul. 18, 2005, 6 pgs.
FDA Medtronic Mini Guardian RT, Jul. 18, 2005, 13 pgs.
Freestyle Navigator User Guide, 2008, 195 pgs.
Guardian Real Time User Guide, 2006, 181 pgs.
Hirsch, "Realistic Expectations and Practical Use of Continuous Glucose Monitoring for the Endocrinologist," J Clin Endocrinol Metab 94:2232-2238 (2009).
Hughes, "The Business of Self-Monitoring of Blood Glucose: A Market Profile," Journal of Diabetes Science and Technology, 3(5):1219-1223 (2009).
Mastrototaro et al., "Accuracy of Real-Time Continuous Glucose Monitoring in the MiniMed Paradigm System," Diabetes 56(1):A112 (2007).
Moore, "The Potential Use of Radio Frequency Identification Devices for Active Monitoring of Blood Glucose Levels," Journal of Diabetes Science and Technology 3(1):180-183 (2009).
Pellikaan Declaration, Abbotts Opening Claim, Jul. 13, 2022, 51 pgs.
Pellikaan Declaration, Bergenstal, Jul. 22, 2010, 11 pgs.
Pellikaan Declaration, Expert Declaration of Sarrafzadeh, Sep. 6, 2024, 100 pgs.
Pellikaan Declaration, JDR CGM Study Group, Oct. 2, 2008, 14 pgs.
Pellikaan Declaration, Mastrototaro, Part 1, Jun. 22-26, 2007, 6 pgs.
Pellikaan Declaration, Mastrototaro, Part 2, 2008, 5 pgs.
Pellikaan Declaration, US FDA, Jul. 18, 2005, 14 pgs.
Pellikaan Declaration, Wolpert, Mar. 2008, 5 pgs.
The Juvenile Diabetes Research Foundation Continuous Glucose Monitoring Study Group, "Continuous Glucose Monitoring and Intensive Treatment of Type 1 Diabetes," N Engl J Med 359:1464-1476 (2008).
Wolpert, "Establishing a Continuous Glucose Monitoring Program," Journal of Diabetes Science and Technology 2(2):307-310 (2008).
Wright Jr. et al., "Ambulatory Glucose Profiling," Supplement to the Journal of Family Practice, 64(12):S44-S47 (2015).
Bluetooth, Bluetooth Basics, Benefits of Bluetooth Technology, https://web.archive.org/web/20060611161103/http://www.bluetooth.com/Bluetooth/Learn/Basics/, 2006, 1 page.
Declaration of Gary D. Fletcher, Ph.D., dated Oct. 10, 2023 for IPR2023-01409, U.S. Pat. No. 11,202,591 (U.S. Appl. No. 17/221,154).
Declaration of Nathaniel E. Frank-White, Nov. 9, 2023, 28 pages.
Dexcom Continuous Glucose Monitoring, Discover Dexcom G5 Mobile Continuous Glucose Monitoring (CGM) System, CGM unveils what no meter can . . . , Oct. 17, 2023, 18 pages.
Dexcom Continuous Glucose Monitoring, FDA Approves Dexcom G5® Mobile Continuous Glucose Monitoring System, Aug. 24, 2015, 6 pages.
Dexcom G4 Platinum Pediatric, User's Guide Dexcom G4® Platinum (Pediatric) Continuous Glucose Monitoring System Received with Share™, 2015, 234 pages.
FDA U.S. Food & Drug Administration, Premarket Approval (PMA), Sep. 16, 2006, https://www.accessdata.fda.gov/scripts/cdrh/cfdocs/cfpma/pma.cfm?ID=388585, 4 pages.
Federal Communications Commission Office of Engineering and Technology Policy and Rules Division, FCC Online Table of Frequency Allocations, Revised on Jul. 1, 2022, 180 pages.
File history of U.S. Appl. No. 17/221,154, filed Apr. 2, 2021 (Exhibit 1002—Part 1-8, 1093 pages in total).
IPhone User Guide for iOS 8.4 Software, 2015, 196 pages.

(56) References Cited

OTHER PUBLICATIONS

Klueh, et al., Inflammation and Glucose Sensors: Use of Dexamethasone to Extend Glucose Sensor Function and Life Span in Vivo, Journal of Diabetes Science and Technology, vol. 1, Issue 4, pp. 496-504 (2007).
Medtronic, CareLink Personal Therapy Management Software for Diabetes, 2007, 20 pages.
Memorandum Opinion, *Abbott Diabetes* v. *Dexcom, Inc.*, Mar. 22, 2023, 47 pages.
Seven STS® Continuous Glucose Monitoring System User's Guide, 2007, 74 pages.
Chuang et al., "Pilot Studies of Transdermal Continuous Glucose Measurement in Outpatient Diabetic Patients and in Patients during and after Cardiac Surgery," Journal of Diabetes Science and Technology, 595-602 (2008).
Letter from the Department of Health & Human Services, Food and Drug Administration (FDA) to Abbott Diabetes Care, Inc. re Premarket Approval Application (PMA) for P050020, FreeStyle Navigator Continuous Glucose Monitoring System, dated Mar. 12, 2008, 8 pages.
McCartney et al., "In vivo glucose sensing for diabetes management: progress towards non-invasive monitoring," BMJ, vol. 319, 4 pages (1999).
Opponent's Written Response in Opposition of EP 3 730 045, Sep. 27, 2023, 43 pages.
510(k) Summary of Safety and Effectiveness, Cleo™ 90 Infusion Set, 2004, 618 pages.
Accu-Chek Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Accu-Chek® Compact Plus, Blood Glucose Meter, Owner's Booklet, 2008, 100 pages.
Certified Copy of U.S. Appl. No. 10/633,367, 2003, 97 pages.
Cleo® 90 Infusion Set Training Guide, 1 page, 2007.
Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.
U.S. Appl. No. 60/587,787, 2004, 69 pages.
Freestyle Navigator User's Guide, 2008, pp. 1-195.
Garibotto, J. et al., "An Innovative Application of Shape Memory Alloy Technology Yields a Novel Therapeutic Approach to Diabetes Management", Insulet Corporation, 2009.
Insulet OmniPod Insulin Management System 019 UST400 User Manual, 2011, 190 pages.
Sen-serter User Guide, Metronic MiniMed, 2006, 96 pages.
Summary of Safety and Effectiveness Data, Continuous Glucose Monitor, FreeStyle Navigator® Continuous Glucose Monitoring System, 2008, 27 pages.
"Within Definition & Meaning" retrieved from "https://www.dictionary.com/browse/within" on Sep. 9, 2022, 5 pages.
Zisser, H. C., "The OmniPod Insulin Management System: the Latest Innovation in Insulin Pump Therapy", Diabetes Ther, 2010, vol. 1, No. 1, pp. 10-24.
Blood glucose monitoring, Wikipedia, 6 pages (2011).
Decuir, J., Bluetooth 4.0: Low Energy, IEEE, 68 pages (2011).
Dementyev, A., et al., Power consumption analysis of Bluetooth Low Energy, ZigBee and ANT sensor nodes in a cyclic sleep scenario, IEEE Conference Paper, 5 pages (2013).
Guardian® RT, Continuous Glucose Monitoring System, REF MMT-7900, User Guide, 128 pages (2005).
IEEE Grid, Your Networking Partner, vol. 59, No. 5, 36 pages (2012).
In Vivo Glucose Sensing, edited by D. Cunningham, et al., Wiley, 62 pages (2010).
Klonoff, D., A Review of Continuous Glucose Monitoring Technology, Diabetes Technology & Therapeutics, vol. 7, No. 5, pp. 770-775 (2005).
Klonoff, D., Continuous Glucose Monitoring, Roadmap for 21st century diabetes therapy, Diabetes Care, vol. 28, No. 5, pp. 1231-1239 (2005).
Medtronic, User Guide, Guardian® REAL-Time, Continuous Glucose Monitoring System, 181 pages (2006).
Morak, J., et al., Design and Evaluation of a Telemonitoring Concept Based on NFC-Enabled Mobile Phones and Sensor Devices, IEEE Transactions on Information Technology in Biomedicine, vol. 16, No. 1, pp. 17-23 (2011).
Movassaghi, S., et al., Wireless Technologies for Body Area Networks: Characteristics and Challenges, 2012 International Symposium on Communications and Information Technologies (ISCIT), IEEE, pp. 42-47 (2012).
Near field communication, Wikipedia, 14 pages (2014).
Specification vol. 0, Specification of the Bluetooth System, Experience More, Mater Table of Contents & Compliance Requirements, 2302 pages (2010).
Townsend, K., et al., Getting Started with Bluetooth Low Energy, O'Reilly, Chapter 1. Introduction, 23 pages (2020).
Townsend, K., et al., Getting Started with Bluetooth Low Energy, O'Reilly, book description, 3 pages (2020).
Bergenstal, et al., Recommendations for Standardizing Glucose Reporting and Analysis to Optimize Clinical Decision Making in Diabetes: The Ambulatory Glucose Profile (AGP), Diabetes Technology & Therapeutics, vol. 15, No. 3, pp. 198-211 (2013).
CareLink Personal Software Quick Start Guide, 2015, 2 pgs.
Clancy, et al., "A new device for assessing changes in skin viscoelasticity using indentation and optical measurement", Skin Research and Technology, 16:210-228 (2010).
Cleo® 90 Infusion Set, Product Literature, Smiths Medical, 2 pages (2022).
Cleo™ 90 Infusion Set Training Guide, Smiths Medical, 1 page (2006).
Dawson, "The Integration of Ground-based Real-time Telemetry Processing, On-board Chapter 10 Aircraft Data Recorders, and 802.11G Links," International Telemetering Conference Proceedings, Aug. 31, 2024, 5 pgs.
DexCom™ STS™ Continuous Glucose Monitoring System, User's Guide, DexCom, Inc., 58 pages (2006).
DexCom™ STS™ Sensor, User Guide, 51 pages (2006).
Diabetes Patents, FreeStyle Libre® Glucose Monitoring System, FreeStyle Libre® 2 Glucose Monitoring System and FreeStyle Libre® 3 Glucose Monitoring System, Abbott, 6 pages (2024).
FDA U.S. Food & Drug Administration, Premarket Approval (PMA), Dexcom G5 Mobile Continuous Glucose Monitoring System (Decision date: Sep. 16, 2016) 4 pages.
U.S. Pat. No. 7,731,691 issued Jun. 8, 2010, 739 pages.
US Trademark Registration No. 3154910 (CLEO), registered on Oct. 10, 2006, 67 pages.
FreeStyle Navigator Continuous Glucose Monitoring System, User's Guide, Abbott Diabetes Care Inc., 191 pages (2008).
FreeStyle Navigator Continuous Glucose Monitoring System, User's Guide, Abbott Diabetes Care Inc., 38 pages (2008).
FreeStyle Navigator® Continuous Glucose Monitoring System, User's Guide, 196 pages (2008).
Grace et al., "Vehicle Network Concept Demonstration," International Telemetering Conference Proceedings, Aug. 31, 2024, 11 pgs.
HDP Spec, Health Device Profile, Jun. 26, 2008, 44 pgs.
Hodack, "Implementing iNET and the Operational Issues Involved," International Telemetering Conference Proceedings, Aug. 31, 2024, 8 pgs.
Johnson, et al., "Chapter 20, Telemetry for Biosensor Systems," Electrochemical Methods of Neuroscience, 13 pgs. (2007).
Kumar Das, et al., Review—Electrochemistry and Other Emerging Technologies for Continuous Glucose Monitoring Devices, ECS Sensors Plus, 1 031601, 19 pages (2022).
Letter from the Department of Health & Human Services, Food and Drug Administration to Mr. David H. Short at Smiths Medical MD, Incorporated re the Cleo 90 Infusion Set, Section 510(k) No. K042172, Premarket Notification dated Oct. 7, 2004, 3 pages.
Mathis, et al., "TCP Selective Acknowledgment Options," Sun Microsystems, Oct. 1996, 14 pgs.

(56) References Cited

OTHER PUBLICATIONS

Mazze, et al., "Evaluating the Accuracy, Reliability, and Clinical Applicability of Continuous Glucose Monitoring (CGM): Is CGM Ready for Real Time", Diabetes Technology & Therapeutics, vol. 11, No. 1, pp. 11-18 (2009).
National Diabetes Statistics Report, CDC Diabetes, 14 pages (May 15, 2024).
Ocean Systems Test and Evaluation Program, Data Communications Plan, May 2006, 199 pgs.
Piper, et al., "Real-Time Continuous Glucose Monitoring in Pediatric Patients During and After Cardiac Surgery", Pediatrics, vol. 118, No. 3, pp. 1176-1184 (2006).
Rabiee, et al., "Numerical and Clinical Accuracy of a Continuous Glucose Monitoring System during Intravenous Insulin Therapy in the Surgical and Burn Intensive Care Units", Journal of Diabetes Science and Technology, vol. 3, Issue 4, pp. 951-959 (2009).
Sacks, et al., "Skin blood flow changes and tissue deformations produced by cylindrical indentors", Journal of Rehabilitation Research and Development, vol. 22, No. 3, pp. 1-6, 11 pages (1985).
Schneider, et al., "Evaluating the use of the Cleo® 90 infusion set for patients on a palliative care unit", International Journal of Palliative Nursing, vol. 15, No. 8, pp. 372-376 (2009).
Seven® Plus Continuous Glucose Monitoring System, Users Guide, Dexcom, 144 pages (2010).
Sohraby, et al., "Wireless Sensor Networks. Technology, Protocols, and Applications," 2007, 326 pgs.
Standards of Medical Care in Diabetes-2007, American Diabetes Association, Diabetes Care, vol. 30, Supplement 1, pp. S4-S41 (2007).
The Wayback Machine, Cleo™ 90 Infusion Set, Smiths Medical, 1 page (2006).
The Wayback Machine, DexCom Products and User Manuals—the Seven System and STS System Manuals, DexCom, 2 pages (2007).
The Wayback Machine, DexCom Products, The Seven System, DexCom, 2 pages (2007).
The Wayback Machine, FreeStyle Navigator Continuous Glucose Monitoring System, Introducing the new FreeStyle Navigator® Continuous Glucose Monitoring System, Abbott Laboratories, 2 pages (2008).
The Wayback Machine, FreeStyle Navigator Continuous Glucose Monitoring System, Answers to Frequently Asked Questions, Abbott Laboratories, 1 page (2008).
The Wayback Machine, FreeStyle Navigator® Continuous Glucose Monitoring System, Answers to Frequently Asked Questions, Abbott Laboratories, 2 pages (2007).
The Wayback Machine, Guardian® REAL-Time System, Features and Components, Medtronic MiniMed, Inc., 4 pages (2007).
The Wayback Machine, Medtronic Main Webpage, Medtronic MiniMed, Inc., 1 page (2007).
The Wayback Machine, Medtronic Product Information, Introducing the Guardian® REAL-Time Continuous Glucose Monitoring System, Medtronic MiniMed, Inc., 3 pages (2007).
The Wayback Machine, Medtronic Product Information, We are the Leader in Diabetes Management, Medtronic MiniMed, Inc., 2 pages (2007).
The Wayback Machine, News—Cleo™ 90 Infusion Set from Smiths wins medical design excellence award, Smiths Medical, 1 page (2006).
The Wayback Machine, News & Events, Smiths Medical, 1 page (2006).
The Wayback Machine, Products and Promotions, Smiths Medical, 1 page (2006).
The Wayback Machine, Smiths Medical Cleo 90 Infusion Set, Ambulatory Infusion Disposables, 2 pages (2022).
The Wayback Machine, Smiths Medical Latest News, Smiths Medical, 2 pages (2006).
The Wayback Machine, Smiths Medical Main Webpage, Smiths Medical, 2 pages (2022).
The Wayback Machine, The STS Seven Continuous Glucose Monitoring System, DexCom, 1 page (2007).
The Wayback Machine, U.S. Food and Drug Administration, Search Premarket Approval (PMA) Database, 1 page (2008).
U.S. Department of Veterans Affairs, Journal of Rehabilitation Research & Development (JRRD), "JRRD 1980-1989" vol. 17-26, 3 pages (1980-1989).
U.S. Food and Drug Administration, 510(k) Premarket Notification, Cleo 90 Infusion Set, 1 page (2004).
U.S. Food and Drug Administration, Premarket Approval (PMA) Search Database, 1 page (2024).
ZigBee Specification, Jan. 17, 2008, 604 pgs.

* cited by examiner

MEDICAL MONITORING SYSTEMS WITH CLOUD COMMUNICATION INTERFACE

PRIORITY

This application claims the benefit, under 35 U.S.C. § 119(e), of U.S. Provisional Patent Application No. 63/214,109, filed 23 Jun. 2021, which is incorporated herein by reference.

BACKGROUND

The disclosed subject matter relates to a system for monitoring medical data about or otherwise associated with a patient securely and with a direct communication interface between medical sensors which provide the data and a remote cloud server for storing, processing, and/or distributing the data.

Certain medical devices can wirelessly transmit data to, and receive data from, other computing devices. While some of these medical devices are equipped with powerful processors and operate using a permanent power supply, other medical devices are designed to operate efficiently, using little power. Low-power medical devices can also have less computational capabilities or resources than devices to which these medical devices are communicating. In some cases, these low-power medical devices have restricted communication abilities as well, typically limited to short-range communication with devices that are within the same room. The low-power medical devices offload much of their data processing to the other devices and can use the other devices as intermediary devices to connect to wider networks, including cloud servers. Cloud servers, in these cases, are usually relied on merely as backup locations for storing historical data or for processing large amounts of anonymized data. Due to the high likelihood of communication failure in this chain between the low-power medical device, intermediary device, and cloud server, it was not considered practical to use the computational efficiencies of the cloud server to improve the functionalities of the sensor or even intermediary device.

Moreover, low-power medical devices can be designed to be disposable and low cost, which requires sacrifices to be made during design and manufacture. Often, the sacrifices include the computational and communication abilities of the low-power medical device. In contrast, in order for intermediary devices to process the medical data provided by these low-power medical device, the intermediary devices must often be relatively expensive devices, equivalent to powerful mobile devices, laptops, or desktop computers. This increased cost increases the barriers to entry for patients who wish to take advantage of low-power medical devices to facilitate monitoring of their medical data. Without a connection to a sufficiently powerful processing device, the low-power medical devices have greatly limited functionality for the average user.

Accordingly, there is an opportunity for methods and systems that can be implemented by low-power, and low-cost, medical devices to make use of advances in cellular networks to increase access to fast and reliable access to remote computer servers.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

To achieve these and other advantages and in accordance with the purpose of the disclosed subject matter, as embodied and broadly described, the disclosed subject matter includes systems and method for a medical monitoring system with a cloud communication interface including medical sensors, data receiving devices, and remote computer servers or medical data servers. Exemplary systems and methods can include a medical monitoring system that includes a medical data server and a medical sensor. The medical sensor includes a sensor control device incorporating an analyte sensor and a cellular radio module in operable communication with the analyte sensor. The medical sensor can be configured to generate medical data indicative of levels of an analyte in a fluid of a patient using the analyte sensor and provide the medical data to the medical data server by communicatively coupling with the medical data server via one or more cellular networks using the cellular radio module. The medical data can include the recorded levels of the analyte. The medical sensor can provide the medical data to the medical data server without user input from the patient. The medical data server can be configured to determine an identifier for the patient based on the medical sensor upon receiving the medical data from the medical sensor. The medical data server can associate the received medical data with medical data stored in association with the identifier for the patient. The medical monitoring system can further include a first external device. The medical data server is then configured to provide the medical data to the first external device via the one or more cellular networks. The medical data server can be further configured to process the medical data provided by the medical sensor, generate a notification for the patient based on analysis of the medical data provided by the medical sensor, and provide the notification to the first external device via the one or more cellular networks. The first external device can be associated with a user authorized by the patient to receive the medical data. The analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. The medical data can further include temperature, heart rate, blood pressure, or movement data. The medical data server can be configured to process the medical data provided by the medical sensor and provide the processed medical data to another data server on behalf of the patient. In certain embodiments, the medical sensor provides the medical data to the medical data server according to one or more transmission parameters. The medical sensor can then be further configured to determine a network connectivity status of the cellular radio module to the one or more cellular networks, and modify the one or more transmission parameters according to the determined network connectivity status. In certain embodiments, the medical sensor further includes a storage memory. The medical sensor can then be further configured to determine that the medical sensor is temporarily unable to communicate with the medical data server via the one or more cellular networks, store the medical data in the storage memory, and subsequent to the medical sensor determining that the medical sensor is able to communicate with the medical data server again, provide the medical data stored in the storage memory to the medical data server via the one or more cellular networks. This can include providing a most recent recorded level of the analyte to the medical data server before providing other medical data stored in the storage memory. In certain embodiments, the medical data server can be configured to determine a location associated with the medical sensor based on the cellular networks and cellular radio module. The medical data server can process the medical data provided by the medical sensor based on the determined location.

According to other aspects of the disclosed subject matter, systems and method can include a method for activating a medical sensor in a medical monitoring system. The method can include receiving, by a medical data server of the medical monitoring system from the medical sensor, a request to activate the medical sensor. The request to activate the medical sensor can include a first identifier. The method can further include receiving by the medical data server from a first external device associated with a first user of the medical monitoring system, a request to authenticate the medical sensor for use by the first user. The request to authenticate the medical sensor can include a second identifier. The method can include determining, by the medical data server, if the first identifier corresponds to the second identifier, and, if the first identifier and the second identifier correspond, authenticating the medical sensor for use by the first user. In certain embodiments, the medical sensor is communicatively coupled with the medical data server via one or more cellular networks. In certain embodiments, after authenticating the medical sensor for use by the first user, the medical data server receives medical data from the medical sensor, processes the medical data, and provides the processed medical data to the first external device. In certain embodiments, the medical data server receives the authentication request before the activation request. In certain embodiments, the medical data server provides an authentication confirmation to the medical sensor or first external device. In certain embodiments, the second identifier is an alphanumeric identifier or a machine-readable identifier. In certain embodiments, the second identifier is received by the first external device from the medical sensor via a short-range communication.

According to other aspects of the disclosed subject matter, systems and methods can include a method for activating a medical sensor in a medical monitoring system. The method includes receiving, by a medical data server of the medical monitoring system from the medical sensor, a request to activate the medical sensor. The request to activate the medical sensor includes a first context including a time or location associated with the request to activate the medical sensor. The method includes receiving by the medical data server from a first external device associated with a first user of the medical monitoring system, a request to authenticate the medical sensor for use by the first user. The request to authenticate the medical sensor includes a second context including a time or location associated with the request to authenticate the medical sensor. The method includes determining, by the medical data server, if the first context corresponds to the second context and if the first context and the second context correspond, authenticating the medical sensor for use by the first user. In certain embodiments, the first context is received from the medical sensor after the activation of a physical interface of the medical sensor. In certain embodiments, the medical sensor is communicatively coupled with the medical data server via one or more cellular networks.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the methods and systems of the disclosed subject matter. Together with the description, the drawings explain the principles of the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts.

DETAILED DESCRIPTION OF EXAMPLE EMBODIMENTS

Figure 1:
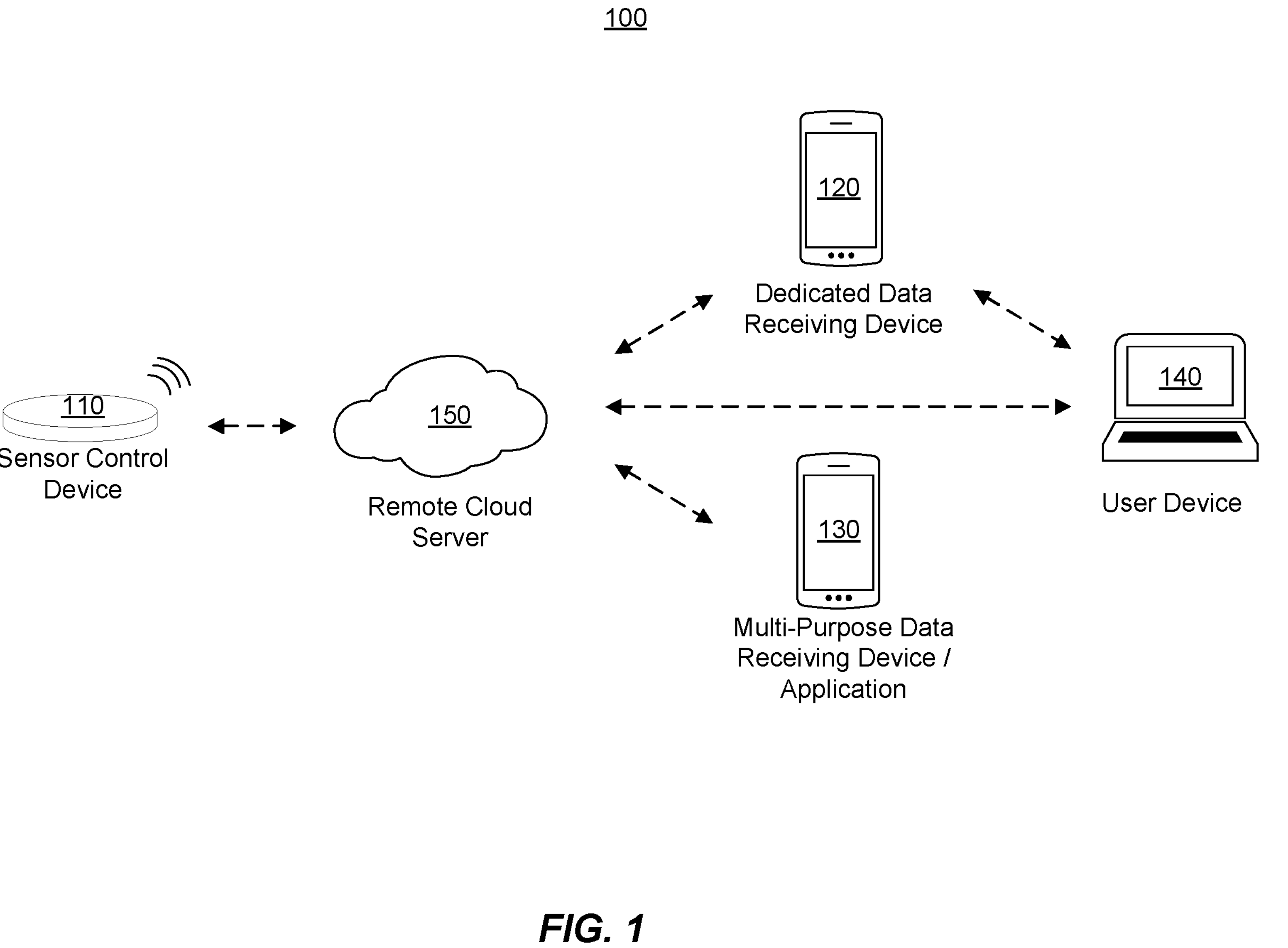
FIG. 1 is a diagram illustrating an operating environment of an example medical monitoring system for use with the techniques described herein.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system The systems and methods presented herein can be used for secure cloud communications in a medical monitoring system. For purpose of illustration of the disclosed subject matter, and not limitation, reference is made herein to secure communications using a medical device, such as a medical sensor. As used herein, "medical sensor" can refer to any device capable of receiving sensor information from a user useful for medical purposes, and can particularly refer to small-format, low-power medical devices, including for purpose of illustration but not limited to, body temperature sensors, blood pressure sensors, pulse or heart-rate sensors, glucose level sensors, analyte sensors, physical activity sensors, body movement sensors, or any other sensors useful for medical purposes. Analytes measured by analyte sensors can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. The purpose and advantages of the disclosed subject matter will be set forth and apparent from the description that follows. Additional advantages of the disclosed subject matter will be realized and attained by the methods, apparatus, and devices particularly pointed out in the written description and claims thereof, as well as from the appended drawings.

For purpose of illustration and not limitation, this disclosure includes methods for secured cloud communication by a medical sensor in accordance with the disclosed subject matter. Exemplary methods can include receiving by a medical sensor an activation signal. The activation signal can be received via an input to a sensor control device of the medical sensor such as through activation of a physical input on the medical sensor, through detection or activation of a connection through the communication module of the sensor control device, through activation of a communication module of the sensor control device via another device, input through a light or brightness sensor of the medical sensor, removal or introduction of a magnet (e.g., detection of a magnetic field or detection of the reduction of the magnetic field). The medical sensor can, in response to the activation signal, initiate communication with a remote computer server, such as a cloud server. Additionally or alternatively, the medical sensor can be continuously active, such as by operating in a low power mode. The medical sensor can periodically attempt to initiate a communication session and/or send or receive specified messages. During an initial round of communication, the medical sensor and cloud server can collaborate to verify identification information for users of the medical sensor and verify authentication values associated with the medical sensor and cloud server. In response to a successful verification, the medical sensor can begin to collect sensor information from a patient. As embodied herein, the sensor information can include medical data about the patient.

According to other aspects of the disclosed subject matter, systems and method can include receiving, by the medical sensor, an authentication request from a computing device. The medical sensor can use information included in the authentication request to generate a challenge response message for the computing device. As embodied herein, the challenge response message can be encrypted according to an agreed-upon encryption scheme. The medical sensor can receive a responsive challenge response message from the computing device and can further verify that the responsive challenge response message corresponds to an expected format and value. The medical sensor can subsequently send a sensor secret to the computing device. The sensor secret can also be encrypted according to an agreed-upon encryption scheme. As embodied herein, the sensor secret can include data unique to the medical sensor and random values. As embodied herein, the random value can be based on predefined values provided to the sensor, values generated by a communication module of the medical sensor, or values generated in response to user interactions. The medical sensor can encrypt one or more medical readings using an encryption key derived from the sensor secret and send the encrypted medical readings to the computing device. As embodied herein, the encryption key can be used with a specialized low-power stream cipher or block cipher. As embodied herein, the medical readings can include body temperature, heart rate, blood glucose levels, motion, and other medical readings.

According to other aspects of the disclosed subject matter, systems and methods can include receiving, by a first computing device from a medical sensor, a set of medical readings encrypted using a first key derived from a sensor secret and a first encryption algorithm. The sensor secret can include unique values associated with the medical sensor and random values generated by the medical sensor. The methods can include deriving, by the computing device, the first key based on the sensor secret. The methods can include decrypting, by the computing device, the set of medical readings using the derived first key. The methods can include encrypting the decrypted medical readings using a second key and a second encryption algorithm. The second key can include information unique to the computing device and random values generated by the computing device. The second encryption algorithm can be different, and as embodied herein, can be a more computationally complex encryption algorithm than the first encryption algorithm. The methods can include transmitting the encrypted medical readings to a second computing device. As embodied herein, the encrypted medical readings can be transmitted to second computing device via wired or wireless communication. The encrypted medical readings can be transmitted using a packet-level-encoding computing protocol. As embodied herein, the methods can include the second computing device decrypting the encrypted medical readings and transmitting them to a third computing device after encrypting the medical readings with the third key and a third encryption algorithm, where the first key, second key, and third key are all different and derived from different root values and where the first encryption algorithm, second encryption algorithm, and third encryption algorithm are all different. As embodied herein, the medical sensor (e.g., the sensor control device of the medical sensor) can include less powerful computational resources than the first computing device. The first computing device can include less powerful computational resources than the second computing device.

For purpose of illustration and not limitation, reference is made to the exemplary embodiment of a medical monitoring system 100 for use with the disclosed subject matter as shown in FIG. 1. FIG. 1 illustrates an operating environment of a medical monitoring system 100 with a cloud communication interface capable of embodying the techniques described herein. The medical monitoring system 100 with a cloud communication interface can include a system of components designed to provide monitoring of medical statistics about a human or animal body or can provide for other medical operations based on the configurations of the various components. For example, the medical monitoring system 100 with a cloud communication interface can provide continuous analyte monitoring to users or can provide for the delivery of drugs and other medicants. As described herein, analyte monitoring can include the continuous detection of levels of a specified analyte in a bodily fluid of the user by an analyte sensor (or other medical hardware) of the medical sensor that is in contact with the bodily fluid. The analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. As embodied herein, the system can include a sensor control device 110 worn by the user or attached to the body for which information is being collected. As embodied herein, the sensor control device 110 can be a sealed, disposable device, to improve ease of use and reduce risk of tampering, as discussed further herein. The medical monitoring system 100 with a cloud communication interface can further include a remote cloud server 150 in communication with the sensor control device 110. The remote cloud server 150 can, among other roles, be the central storage facility for medical data received from the sensor control device 110, identification information for the various users of the medical monitoring system 110, and provide operational instructions to the sensor control device 110 and other devices involved in the medical monitoring system.

As further illustrated in FIG. 1, the medical monitoring system 100 with a cloud communication interface can include a dedicated reading device 120 configured as described herein to facilitate retrieval of data, including medical data from the remote cloud server 150 for display to a user of the medical monitoring system 100, such as the user wearing the sensor control device 110, a guardian or other authorized user associated with the user wearing the sensor control device 110, or a medical professional authorized by the user wearing the sensor control device 110.

As embodied herein, the medical monitoring system 100 with a cloud communication interface can, additionally or alternatively, include a software or firmware library or application provided to a third-party and incorporated into a multi-purpose hardware device 130. Multi-purpose data receiving device 130 can be a mobile communication device such as, for example, a Wi-Fi or internet enabled smartphone, tablet, personal digital assistant (PDA) capable of communication with the remote cloud server 150. Examples of smartphones can include, but are not limited to, those phones based on a WINDOWS operating system, ANDROID operating system, IPHONE operating system, PALM, WEBOS, BLACKBERRY operating system, or SYMBIAN operating system, with data network connectivity functionality for data communication over an internet connection and/or a local area network (LAN). Multi-purpose data receiving device 130 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly can be capable of wireless communications similar to a smartphone. Other examples of wearable electronics include devices that are worn around or in the proximity of the user's wrist (e.g., a smart watch, etc.), neck (e.g., a necklace, etc.), head (e.g., a headband, hat, etc.), chest, or the like. Multi-purpose hardware can further include embedded devices, including but not limited to insulin pump or insulin pens, having an embedded library configured to communicate with the remote cloud server 150 to receive medical data. Multi-purpose device 130 embodying and executing the library can be said to form a data receiving device for communicating with the remote cloud server 150. As used herein, a dedicated data receiving device 120 refers to a hardware device specifically manufactured for communicating with the remote cloud server 150 within the medical monitoring system 100 with a cloud communication interface whereas a multi-purpose data receiving device 130 refers to a suitably configured hardware device which incorporates the software library or is executing the application.

Unless specifically noted, the described methods and systems involving a dedicated data receiving device 120 are equally applicable to a multi-purpose data receiving devices 130. It should be understood that the architecture and design principles discussed herein are equally applicable to any suitably configured system involving a medical device 110, a suitably configured dedicated data receiving device 120 or multi-purpose data receiving device 130, and other similar components as those described herein. The role of the medical device 110 can be defined by the nature of the medical hardware embodied in the medical device 110.

As embodied herein, the sensor control device 110 can include small, individually-packaged disposable devices with a predetermined active use lifetime (e.g., 1 day, 14 days, 30 days, etc.). As embodied herein, sensors 110 can be configured for one-time use and applied to the skin of the patient body remain adhered over the duration of the sensor lifetime. Alternatively, sensors 110 can be designed to be selectively removed and remain functional when reapplied.

Although the illustrated embodiments of the medical monitoring system 100 with a cloud communication interface include only one of each of the sensor control device 110, dedicated data receiving device 120, multi-purpose data receiving device 130, user device 140, and remote cloud server 150, this disclosure contemplates the medical monitoring system 100 with a cloud communication interface incorporate multiples of each components interacting throughout the system. For example, the embodiments disclosed herein include multiple sensors 110 that can be associated with multiple patients which are in communication with the remote cloud server 150. Additionally, the remote cloud server is illustrated as a single entity 150, however will be understood that it can encompass multiple networked servers that can be geographically distributed to reduce latency and introduce deliberate redundancy to avoid monitoring system downtime.

Figure 2:
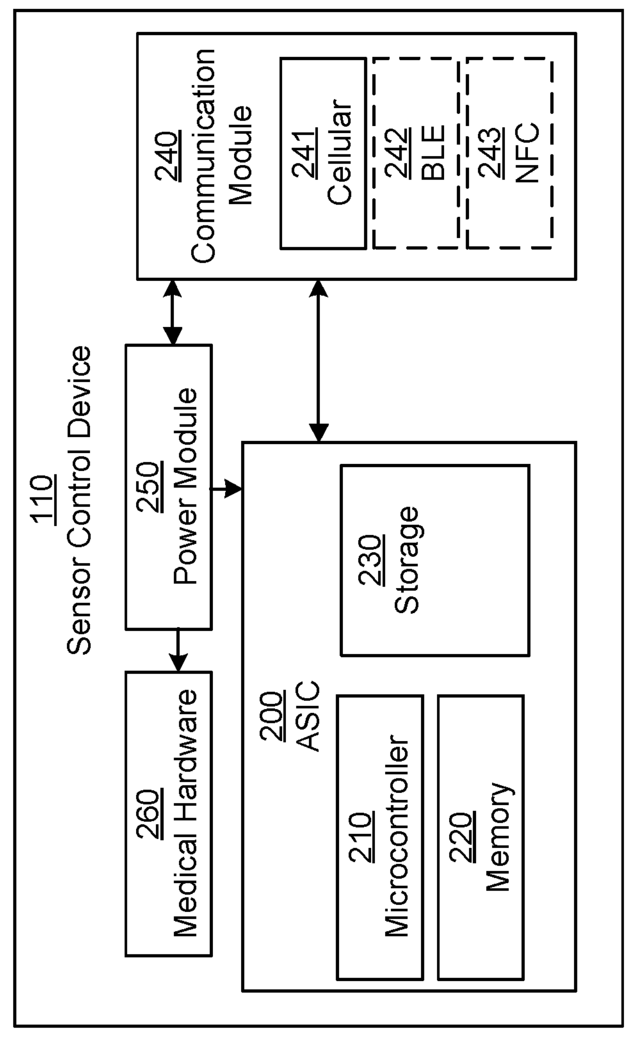
FIG. 2 is a block diagram illustrating an example sensor control device according to exemplary embodiments of the disclosed subject matter.

For purpose of illustration and not limitation, reference is made to the exemplary embodiment of a sensor control device 110 for use with the disclosed subject matter as shown in FIG. 2. FIG. 2 illustrates a block diagram of an example sensor control device 110 according to exemplary embodiments compatible with the security architecture and communication schemes described herein. As embodied herein, the sensor control device 110 can include an Application-Specific Integrated Circuit ("ASIC") 200 communicatively coupled with a communication module 240. As embodied herein, as the sensor control device 110 is designed to be power-efficient, low-cost, and possibly disposable, the ASIC 200 can include a microcontroller core 210, on-board memory 220, and storage memory 230. The storage memory 230 can store data used in the authentication and encryption security architecture disclosed herein. The data can have various elements and uses, including as described in the examples herein. The ASIC 200 can receive power from a power module 250, such as an on-board battery. The on-board battery can be manufactured using, for example, printed (e.g., 3D printed) battery techniques. The power module 250 can store only a relatively small charge. As embodied herein, the sensor control device 110 can be a disposable device with a predetermined life span. As embodied herein, the communication module 240 can provide for communication under battery power. Although this disclosure is described with respect to exemplary configurations of the sensor control device 110 and the ASIC 200, other suitable configurations are envisioned. As an example, processing hardware of the sensor control device 110 can be implemented as another type of special-purpose processor, such as a field programmable gate array (FPGA) or a system-on-chip (SOC) comprising multiple components packaged together on the same chip. As embodied herein, the processing hardware of the sensor control device 110 can include a general-purpose processing unit (e.g., a CPU) or another programmable processor that is temporarily configured by software to execute the functions of the sensor control device 110. More generally, the processing hardware can be implemented using hardware, firmware, software, or a suitable combination of hardware, firmware, and software. For purpose of illustration and not limitation, the processing hardware of the sensor control device 110 can be defined by one or more factors including computational capability, power capacity, memory capacity, availability of a network connection, etc. Additionally or alternatively, although illustrated in FIG. 2 as separate components, the ASIC 200 can be included within the communication module 240.

As embodied herein, the communication module 240 of the sensor control device 110 can be or include one or more modules to support the sensor control device 110 communicating with other devices of the medical monitoring system 100, especially the remote cloud server 150. In certain embodiments, the sensor control device 110 can communicate, for example, with a dedicated data receiving device 120 or user device 140 as a mode of backup communication with the remote cloud server 150. The communication module 240 can include, for example, a cellular radio module 241. The cellular radio module 241 can include one or more radio transceivers and/or chipsets for communicating using cellular networks, including, but not limited to third generation (3G), fourth generation (4G), and fifth generation (5G) networks. Using the cellular radio module 241 the sensor control device 110 can communicate with the remote cloud server 150 to provide medical data (e.g., sensor readings) and can receive data intended for the user, such as information relating to medical health and/or status, alerts, and/or information about the status of the sensor control device 110. Although this disclosure describes embodiments using communication using 5G networks, this disclosure contemplates suitable modifications to the techniques described herein without departing from the focus of this disclosure.

As another example, the communication module 240 can include a BLE 242 module and/or an NFC module 243 to facilitate communication with a dedicated data receiving device 120 or user device 140 acting as a NFC scanner or BLE endpoint. As used throughout this disclosure, Bluetooth Low Energy ("BLE") refers to a short-range communication protocol optimized to make pairing of Bluetooth devices simple for end users. As described herein, this can serve as a mode of back-up communication when the sensor control device 110 is otherwise incapable of communicating with the remote cloud server 150 to deliver medical data. The communication module 240 can include additional or alternative chipsets for use with similar short-range communication schemes, such as a personal area network according to IEEE 802.15 protocols, IEEE 802.11 protocols, infrared communications according to the Infrared Data Association standards (IrDA), etc. The communication module 240 can transmit and receive data and commands via interaction with similarly-capable communication modules of a dedicated data receiving device 120 or user device 140. Certain communication chipsets can be embedded in the ASIC 200 (e.g., an NFC antennae loop). Additionally, although not illustrated, the communication module 240 of the sensor control device 110 can include a radio for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)). As such, the communication module 240 is configured to communicate using all manner of communication networks, including short and long range, slow and high speed, and of any application size, including micro or personal networks up to global public or private Internetworks.

As embodied herein, the sensor control device 110 can use application layer encryption using one or more block ciphers to establish mutual authentication and encryption. The use of a non-standard encryption design implemented in the application layer has several benefits. One benefit of this approach is that in certain embodiments the user can complete the pairing of a sensor control device 110 and another device with minimal interaction, e.g., using only an NFC scan and without requiring additional input, such as entering a security pin or confirming pairing To perform its medical functionalities, the sensor control device 110 can further include suitable medical hardware 260 appropriate to its function. As embodied herein, the medical hardware 260 can include, for example, an autoinjector prescribed to a patient for self-administering a drug or other medicament. Accordingly, the medical hardware 260 can include a mechanism that drives a needle or a plunger of a syringe in order to subcutaneously deliver a drug. The syringe can be pre-filled with the drug and can operate in response to a triggering event. For example, the mechanism can drive the needle into the patient and advance the plunger to deliver the drug subcutaneously via the needle.

As embodied herein, the medical device 110 can be configured as an on-body injector attachable to a patient's body tissue (e.g., skin, organ, muscle, etc.) and capable of automatically delivering a subcutaneous injection of a fixed or patient-selected dose of a drug over a controlled or selected period of time. In such embodiments, the medical hardware 260 or medical device can include, for example, an adhesive or other means for temporarily attaching the medical hardware 260 to the patient's body tissue, a primary container for storing a drug or medicament, a drive mechanism configured to drive or permit the release of a plunger to discharge the drug from the primary container, a trocar (e.g., a solid core needle), a flexible cannula disposed around the trocar, an insertion mechanism configured to insert the trocar and/or flexible cannula into the patient and optionally retract the trocar leaving the flexible cannula in the patient, a fluid pathway connector configured to establish fluid communication between the primary container and the flexible cannula upon device activation, and an actuator (e.g., a user displaceable button) configured to activate the device. As embodied herein, the on-body injector can be pre-filled and/or pre-loaded.

In addition to mechanical components, the medical hardware 260 can include electric and/or electronic components. For example, an electronic switch can be coupled to the mechanism. The medical device 110 can establish an authenticated communication, receive an encrypted signal, decrypt the signal using the techniques of this disclosure, determine that the signal includes a command to operate the switch, and cause the switch to drive the needle. Thus, the medical device embodied herein can be configured to perform a medical function using the medical hardware 260 in response to a remote command.

As embodied herein, the medical hardware 260 can include a travel sensor and an analog-to-digital converter to generate a digital signal indicative of the distance travelled by the needle or plunger. Upon delivering the medicament, the medical device 110 can obtain a reading from the sensor, encrypt the reading using the techniques of this disclosure, and securely report the reading to the remote server 150. Additionally or alternatively, the medical device 110 can report other measurements or parameters, such as a time at which the medicament was delivered, volume of medicament delivered, any issues encountered while delivering the medicament, etc. The medical device 110 can be configured to provide data related to the operation of the medical hardware 260 to the remote cloud server 150.

The medical hardware 260 can be configured to implement any suitable combination of one or more medical functions and can include one or more sensing components. Such sensing components can be configured to detect an operational state of the medical device 110 (e.g., unpackaged/ready for administration, sterile barrier removal, contact with patient's body tissue, cannula and/or needle insertion, drug delivery initiation, actuator or button displacement, drug delivery completion, plunger position, fluid pathway occlusion, etc.), a condition of the medical device 110 or drug contained therein (e.g., temperature, shock or vibration exposure, light exposure, drug color, drug turbidity, drug viscosity, geographic location, spatial orientation, temporal information, ambient air pressure, etc.), and/or physiological information about the patient (e.g., body temperature, blood pressure, pulse or heart rate, glucose levels, physical activity or movement, fingerprint detection, etc.). This detected information can be offloaded from the sensor control device 110 to facilitate storage and analysis, for example by the remote cloud server 150. As embodied herein, the medical device 110 can be configured to both receive encrypted data from the remote cloud server 150 and transmit encrypted data to the remote cloud server 150. As embodied herein, the sensor control device 110 can be optionally configured to both receive encrypted data from a dedicated data receiving device 120 or multi-purpose data receiving device 130 and transmit encrypted data to the dedicated data receiving device 120 or multi-purpose data receiving device 130.

Referring still to FIG. 2, the ASIC 200 of the sensor control device 110 can be configured to dynamically generate authentication and encryption keys using the data retained within the storage memory 230. The storage memory 230 can also be pre-programmed with a set of valid authentication and encryption keys to use with particular classes of devices. The ASIC 200 can be further configured to perform authentication procedures with a remote cloud server 150 (e.g., handshake, mutual authentication, etc.) using received data and apply the generated key to sensitive data prior to offloading the sensitive data, such as sending the sensitive data to the remote cloud server 150 via the communication module 240. The generated key can be unique to the sensor control device 110, unique to a pair of devices (e.g., unique to a particular pairing of a sensor control device 110 and a particular remote cloud server 150), unique to a communication session between a sensor control device 110 and remote cloud server 150, unique to a message sent during a communication session, or unique to a block of data contained within a message. The techniques implemented by the ASIC 200 of the sensor control device 110 are discussed in more detail herein.

Figure 3:
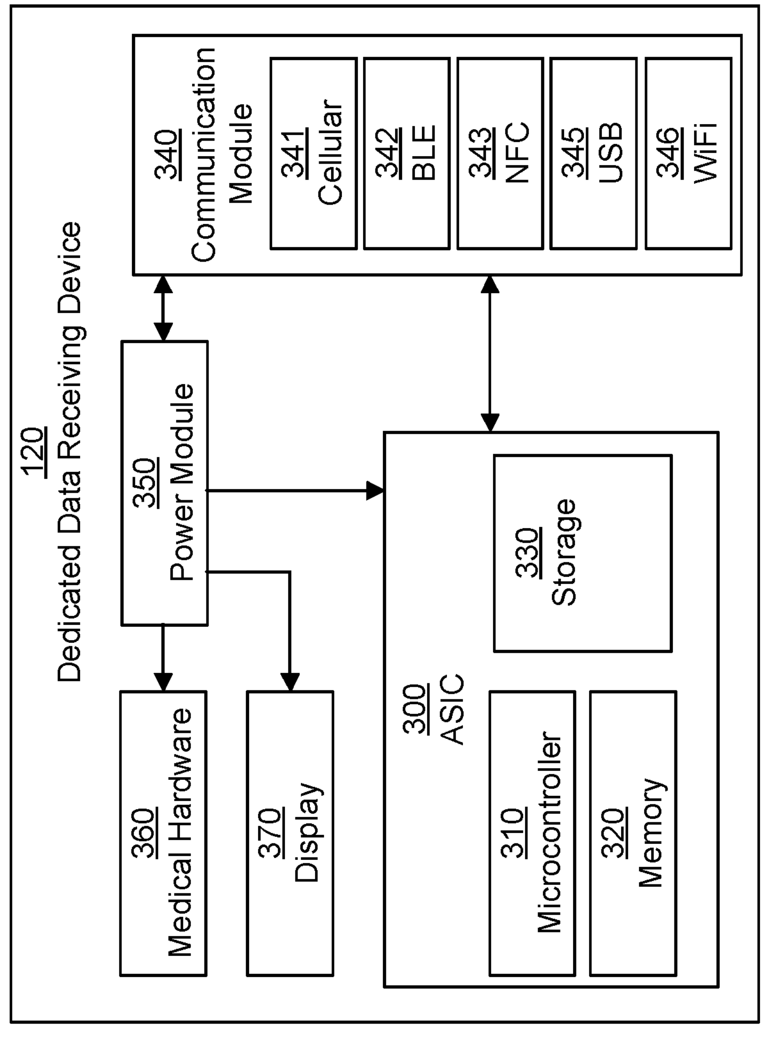
FIG. 3 is a block diagram illustrating an example dedicated data receiving device for communicating with the sensor control device according to exemplary embodiments of the disclosed subject matter.

For purpose of illustration and not limitation, reference is made to the exemplary embodiment of a dedicated data receiving device 120 for use with the disclosed subject matter as shown in FIG. 3. FIG. 3 illustrates an example dedicated data receiving device 120 compatible with the direct-to-cloud environment described herein with respect to exemplary embodiments. As embodied herein, the dedicated data receiving device 120 can include a small-form factor device. The dedicated data receiving device 120 can optionally not be as memory- or processing-power constrained as the sensor control device 110, and as embodied herein, the dedicated data receiving device 120 can include sufficient storage memory for operational software storage and data storage, and sufficient RAM for software execution to communicate with the remote cloud server 150 as described herein.

In particular, the dedicated data receiving device 120 can be designed with cost in mind, to reduce the financial loss due to accidental damage or destruction of the dedicated data receiving device 120. As described herein, in the medical monitoring system 100, the bulk of processing is performed by a remote cloud server 150. Thus, the dedicated data receiving device 120 need only accommodate the computing power (and financial cost) necessary for it to communicate with the remote cloud server 150 and possibly one or more other devices as a form of backup communication. The dedicated data receiving device 120 is therefore suitable for use by a wider range of individuals for monitoring their medical data (e.g., analyte levels) as an alternative to monitoring personal medical data using another expensive user device, such as a standard mobile device, tablet, or laptop.

As illustrated in FIG. 3, the dedicated data receiving device 120 includes an ASIC 300 including a microcontroller 310, memory 320, and storage 330 and communicatively coupled with a communication module 340. As embodied herein, the on-board storage 330 of the dedicated data receiving device 120 can store medical data received from the remote cloud server 150 before it is displayed to the user. As embodied herein, the ASIC 300 can be identical to the ASIC 200 of the sensor control device 110. Alternatively, the ASIC 300 can be configured to include additional computing power and functionality. Note, however, that because nearly all processing of medical data is offloaded to the remote cloud server 150 from the sensor control device 110 without touching the dedicated data receiving device 120 as an intermediary, and because the dedicated data receiving device 120 need not communicate directly with the sensor control device 110, the ASIC 300 can generally be simplified while still provided full-featured access to the medical monitoring system 100. As embodied herein, the ASIC 300 can be customized for the dedicated data receiving device 120. In addition or as a further alternative, data receiving device 120 can include a general-purpose microcontroller configured with software instructions to perform the operations described herein.

The dedicated data receiving device 120 can further include a display 370 for facilitating review of medical data provided by the remote cloud server 150. The display 370 can be a power-efficient display with a relatively low screen refresh rate to conserve energy use and further reduce the cost of the dedicated data receiving device. The display 370 can be a low-cost touch screen to receive user input through one or more user interfaces. Although not illustrated, the dedicated data receiving device 120 can include separate user interface components (e.g., physical keys, light sensors, microphones, etc.). Power for the components of the dedicated data receiving device 120 can be delivered by a power module 350, which as embodied herein can include a rechargeable battery, allowing for sustained operations and continued use.

As embodied herein, the communication module 340 of the dedicated data receiving device 120 can include a number of modules to support the dedicated data receiving device 120 communicating with other devices of the medical monitoring system 100 with a cloud communication interface, such as the remote cloud server 150 and sensor control device 110 in certain embodiments. Although illustrated as separate components, in particular embodiments, a processor of the communication module 340 can perform the processing operations ordinarily performed by the microcontroller 310 of the ASIC 300. Thus, the ASIC 300 can be removed and memory and other storage added to the communication module to simplify the hardware required of the dedicated data receiving device.

The communication module 340 can include, for example, a cellular radio module 341. The cellular radio module 341 can include one or more radio transceivers for communicating using cellular networks, including, but not limited to third generation (3G), fourth generation (4G), and fifth generation (5G) networks. Using the cellular radio module 341 the dedicated data receiving device 120 can communicate with the remote cloud server 150 to receive medical data or provide input received from a user (e.g., through one or more user interfaces). The dedicated data receiving device 120 can further, for example, receive software or firmware updates via the cellular radio module 341. Although this disclosure describes embodiments using communication using 5G networks, this disclosure contemplates suitable modifications to the techniques described herein without departing from the focus of this disclosure. Additionally the communication module 340 of the dedicated data receiving device 120 can include a WiFi radio module 346 for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)) or low power wireless area networks.

As another example, the communication module 340 can include a BLE 342 module and an NFC module 343. As embodied herein, the dedicated data receiving device 120 can be configured to operate, with respect to the sensor control device 110 as described herein, as an NFC scanner and a BLE end point via specific modules (e.g., BLE module 342 or NFC module 343) of the communication module 340. As described herein, this can serve as a mode of back-up communication when the sensor control device 110 is otherwise incapable of communicating with the remote cloud server 150 to deliver medical data. As embodied herein, the dedicated data receiving device 120 can be configured for communication via a Universal Serial Bus (USB) module 345 of the communication module 340. The dedicated data receiving device 120 can communicate with a user device 140 for example over the USB module 345. The dedicated data receiving device 120 can, for example, receive software or firmware updates via USB, receive bulk data via USB, or upload data to the remote cloud server 150 via the user device 140. USB connections can be authenticated on each plug event. Authentication can use, for example, a three-pass design with different keys. The USB system can support a variety of different sets of keys for encryption and authentication. Keys can be aligned with differential roles (clinical, manufacturer, user, etc.).

As embodied herein, the dedicated data receiving device 120 can optionally include medical hardware 360 similar to the medical hardware 260 of the sensor control device 110 or having increased capacity. For example, the medical hardware 360 can include a sensor for measuring levels of an analyte within a bodily fluid of the user by an analyte sensor that is or can be brought into contact with the bodily fluid. The analyte can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. As an example only, and not by way of limitation, in an embodiment in which the medical hardware 260 of the sensor control device 110 is configured for continuous glucose (or other analyte) monitoring, the medical hardware 360 of the dedicated data receiving device 120 can be configured with a blood glucose meter, compatible for use with blood glucose test strips, thus expanding on the glucose monitoring of the sensor control device 110.

Because the dedicated data receiving device 120 is designed to be a durable, low-cost alternative to more expensive options for accessing the medical monitoring system 100, the dedicated data receiving device 120 can be ruggedized to protect against accidental damage or destruction. All components of the dedicated data receiving device 120 can be selected to reduce the manufacturing cost, and the cost of providing to the cost, as well as improving usability and durability. As an example, the display can be made using scratch- and crack-resistant materials (e.g., rugged plastic instead of glass) that are easily readable in direct sunlight. As another example, the enclosure of the dedicated data receiving device can be made using wear-resistant materials (e.g., rugged plastic instead of aluminum or glass) which are selected to be more resistant to damage from falls, waterproof, heat-resistant, etc. Additionally, the dedicated data receiving device 120 can be provided with an array of cases to further enhance durability.

Figure 4:
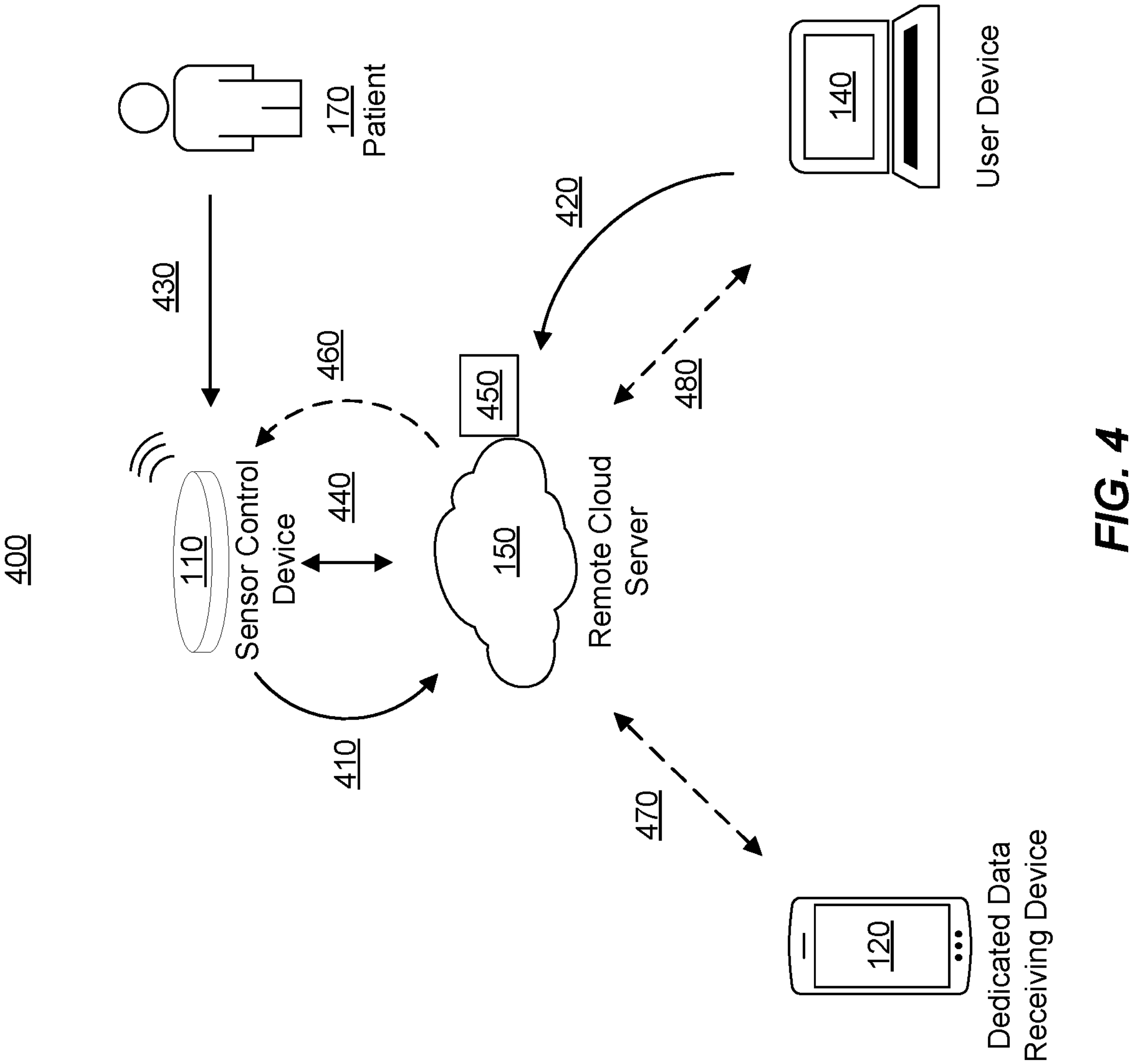
FIG. 4 is a diagram illustrating an example operational flow and data lifecycle of the medical monitoring system.

FIG. 4 illustrates an example flow of data through the medical monitoring system 100 with a cloud communication interface. FIG. 4 illustrates an exemplary embodiment of an operational flow and data lifecycle 400 of the medical monitoring system 100 with a cloud communication interface for use with the disclosed subject matter.

At step 410, the sensor control device 110 can send an activation signal to the remote cloud server 150. The activation signal can be provided automatically upon activation of the sensor control device 110 itself once the sensor control device 110 is able to connect to a network that provides a communication channel to the remote cloud server 150. For example, once the sensor control device 110 has been activated and is able to connect to a cellular network using a cellular radio 241 of its communication module 240, the sensor control device 110 can send a signal to the remote cloud sensor 150. In particular embodiments the sensor control device 110 can send a dedicated activation signal indicating that the sensor 150 has just been activated for the first time by a user. In other embodiments, the sensor control device 110 can be configured to send a standard signal to the remote cloud server 150 (e.g., a report of medical data or a so-called "heartbeat" signal). The remote cloud server 150 can determine that the sensor control device 110 had not previously communicated with the remote cloud server 150 and interpret the signal as an activation signal. In particular embodiments, the activation signal can be triggered upon deployment of a physical actuator, such as a mechanical button or switch. The activation signal can be further triggered upon actuation of a touch screen, or an electrical or mechanical switch. For example, the activation signal can be provided upon receipt by the sensor control device 110 of an NFC scan, presentation of a predetermined magnetic field, or detection of a light source or absence of a light source.

Substantially contemporaneously with the activation signal, at step 420, the user can send a second activation signal or authentication to the remote cloud server 150. To allow the sensor control device 110 to be configured with simplified computing capability and user interface options, the medical monitoring system 100 can accommodate the user providing confirmation of the activation of the sensor control device 110 using a different device. This confirmation can also serve as authentication for the sensor control device 110 and the medical readings obtained therefrom to be associated with the user in the data maintained by the remote cloud server 150. As an example, the user can provide the authentication signal by using a user device 140 to log into an application or web portal provided by the manufacturer of the sensor control device 110 or operator of the medical monitoring system 100. Upon logging in, the user can be shown a list of sensors 110 associated with their account. The user can be provided a user interface element into which the user can enter an identification code associated with the sensor control device 110. The remote cloud server 150 can compare the activation signal from the sensor control device 110 with the authentication signal from the user and, upon confirming a match or correspondence between the activation signal and authentication signal, instruct the sensor control device 110 to begin recording and sending medical data and/or associating data from the sensor control device 110 with the user. As illustrated, the user 170 uses a secondary user device 140 to send the second activation signal, although the user 170 can use any device that is suitably in communication with the remote cloud server 150 and capable of providing secondary verification of the activation of the sensor control device 110 to the remote cloud server 150 consistent with the embodiments described herein.

At step 430, the sensor control device 110 can collect medical data, such as from the user 170 (e.g., a human or animal body). In some cases, the user 170 is not the same user as activated the sensor, for example in the context of a medical professional activating a device on behalf of a patient or a "blinded" embodiment as described herein. For example, the sensor control device 110 can collect data at predetermined intervals upon activation.

At step 440, the sensor control device 110 can transmit the medical data to the remote cloud server 150 over a communication interface via its communication module 240 (e.g., via a cellular radio connection or Wi-Fi connection, etc.). In addition to the medical data, the sensor control device 110 can transmit additional information to facilitate exchange along the chosen protocol. For example, message payloads from the sensor control device 110 to the remote cloud server 150 can include manufacturer-specific values, manufacturer-identifying values, identifying values for the sensor, transmission power level values, sensor status information, etc. This information can be used to identify the sensor control device 110 from among a crowd of sensor control devices that are also sending medical data to the remote cloud server. Sensor status information can include information about the remaining battery level of the sensor control device 110, the temperature of the sensor control device 110 or the ambient environment of the sensor control device 110, etc. The remote cloud server 150 can send a return signal to the sensor control device 110 acknowledging receipt of the transmitted information. The sensor control device 110 can interpret the return signal as permission to delete redundant data.

At step 450, after receiving the medical data from the sensor control device 110, the remote cloud server 150 processes the data and provides for notifications to the user. As described herein, processing the data can include identifying the patient associated with the data (e.g., based on an identifier for the sensor control device 110 that is associated with an identifier for the patient). Processing the data can further include associating the received data with previously received data for the patient based on the identification. As embodied herein, the data received from the sensor control device 110 can include raw values from an analog-to-digital converter on the sensor control device 110. Thus, the remote cloud server 150 can process the raw values into more easily interpretable representations, e.g., of the levels of the analyte being detected by the sensor control device 110. For example, the remote cloud server 150 can apply algorithms to convert the received values. The algorithms can take into consideration, for example, the values from the sensor control device 110, the remaining power levels of the sensor control device 110, the temperature of the sensor control device 110 and its ambient environment, etc. The remote cloud server 150 thus can be configured to perform the bulk of the processing of the data. In other embodiments, some of the processing can be performed by the sensor control device 110 on-device (e.g., by the ASIC 200 or communication module 240). For example, the sensor control device 110 can convert raw measurements from an analog-to-digital converter to more direct measurements of an analyte of interest. The data sent to the remote cloud server 150 can include these measurements. In step 450 then, the remote cloud server 150 records and processes these measurements using one or more applicable algorithms and analyzes the data for predetermined trends or conditions in the data and prepares alerts or other notifications that should be provided to the user. As embodied herein, the algorithms and/or the selection of algorithms can be based on user-provided information. As an example, the user can inform the remote cloud server 150 (e.g., through a dedicated data receiving device 120, multi-purpose data receiving device, or user device 140) of possible interferents. The algorithms used by the remote cloud server 150 can accordingly adjust the processing of the data based on the user-provided information.

Steps 460, 470, and 480 pertain to example methods for the remote cloud server 150 to alert the user 170 (or an authorized recipient of the alerts for the user 170) based on the medical data received from the sensor control device 110. These methods can be considered optional, as the medical monitoring system 100 need not necessarily implement all of them into order to practice the embodiments described herein.

A first notifying technique, illustrated as step 460, involves the remote cloud server 150 providing instructions back to the sensor control device 110 to provide an alert or notification to the sensor control device 110. In some embodiments, the sensor control device 110 includes some limited methods of communicating information to the user 170 who is wearing the sensor control device 110. The sensor control device 110 can include a small display, which can be interactive. The sensor control device 110 can include, instead of a full display, a collection of indicator lights which can provide for status levels according to a set pattern (e.g., green indicating levels are acceptable, yellow indicating levels are low, red indicating levels are high, blinking to indicate that levels are changing or expected to change rapidly, etc.). The sensor control device 110 can include a small speaker to provide information. For example, the speaker can announce when analyte levels are outside of a threshold safety range or when they have entered one or more threshold critical ranges. The sensor control device 110 can include limited haptic feedback through specific vibrations or patterns of vibrations. For example, the sensor control device 110 can vibrate twice in five seconds to alert the user that some informational message is available for them to view (e.g., through another device as described herein), the sensor control device 110 can vibrate rapidly over ten seconds if there is a critical alert, etc. The sensor control device 110 can provide stimulation to the user through electrical feedback. For example, the sensor control device 110 can lightly shock the user to alert the user that an informational message is available for the user to view. The sensor control device 110 can issue a more powerful shock, for example, if the message includes an urgent alert (such as the onset of a medically dangerous event). In some embodiments, the user 170 can acknowledge receipt of a notification or dismiss it using an interactive component of the sensor control device 110. The sensor control device 110 can further interface with other connected devices (e.g., so-called "internet of things" (IOT) devices) through the communication module 240. For example, the sensor control device 110 can turn on connected lights within the room of the user, cause a connected speaker to play an audible announcement, and/or cause a visual notification to be displayed on a connected television (or other device with a display screen) such as by turning the connected television on or by modifying the display of the connected television.

A second notifying technique, illustrated as step 470, involves the remote cloud server 150 providing information, including alerts, notifications, instantaneous readings, medical data trends, etc., to the dedicated data receiving device 120 for review by the user 170 or an authorized recipient. The authorized recipient can include a family member (e.g., parent or other caregiver) or medical professional. The authorized recipient can be remote from the user (e.g., a patient's primary care physician, parent of a child a school, etc.). As described herein, the dedicated data receiving device 120 can be a cost-effective separate device for reviewing medical data within the medical monitoring system 100, e.g., in lieu of requiring the user 170 to provide a full-featured user device 140 such as a laptop or multi-purpose data receiving device 130 such as a mobile phone. The dedicated data receiving device 120 is referred to as a "dedicated" device because of its limited functionality outside of the context of the medical monitoring system 100. Because the dedicated data receiving device 120 is connected to the remote cloud server 150 via one or more wireless networks including Wi-Fi or cellular networks (e.g., 4G, 5G), medical data or notifications generated by the remote cloud server 150 can be quickly sent to the dedicated data receiving device 120 for display. The dedicated data receiving device 120 can provide any of the same array of user notification methods described above, including visual (e.g., notification lights or an interactive user interface), audible, or haptic. The dedicated data receiving device 120 can include more full featured versions of these notification methods and can include several of them because the dedicated data receiving device can include a larger battery than the sensor control device 110 and a battery that is easily rechargeable or replaceable battery.

In particular embodiments, the data receiving device includes a multi-purpose device, such as a drug delivery device. The drug delivery device can include a mechanism to inject a selected drug, such as insulin, upon receiving an appropriate signal from the remote cloud server. As an example only, the data receiving device incorporating the drug delivery device can receive glucose data corresponding to the wearer of the device. The drug delivery device can determine based on the glucose data that the dosage of insulin should be adjusted. Additionally, the remote cloud server 150 can provide configuration instructions to the drug delivery device that can adjust insulin doses or rates, or trigger insulin directly. This can form part of a closed loop system for drug delivery. Therefore, in addition to providing notifications, the data receiving device can take action on behalf of the wearer.

A third notifying technique, illustrated as step 480, involves the remote cloud server 150 providing information, including alerts, notifications, instantaneous readings, medical data trends, etc., to a user device 140 for review by the user 170 or an authorized recipient. In this context the user device 140 can include any multi-function computing device capable of executing an application provided by the operator of the medical monitoring system 100 or capable of accessing a website or web portal provided by the operator and may, e.g., include a multi-purpose data receiving device 130. Thus, the user device 140 can include a laptop, tablet, smartphone, etc. capable of communicating with the remote cloud server 150 via a wide area network. Because the user device 140 can take a variety of form factors, the medical monitoring system 100 can provide for numerous notification techniques to provide necessary information to the user 170 or an authorized recipient. For example, the application provided by the operator of the medical monitoring system 100 can request access to features of the user device 140, such as a system native notification service to allow for notifications to be issued. The application can request access to provide visual, audible, and/or haptic notifications when pushed by the remote cloud server 150. In addition to directed notifications the user device 140 can facilitate review of current and historical medical data. For example, the user can use the user device 140 to log into the website, web portal, or application. By authenticating their account, the remote cloud server 150 can provide access to the medical data associated with the user account. Thus, the user 170 is not required to carry a dedicated data receiving device 120 with them at all time. For convenience, they can easily access important medical information based on the readings of the sensor control device 110 using any suitable computing device.

Although not illustrated, in certain embodiments, the sensor control device 110 can be communicatively coupled to a dedicated data receiving device 120, multi-purpose data receiving device 130, or user device 140 to act as a backup mode of communication in the event that the sensor control device 110 is unable to communicate with the remote cloud server 150. For example, the cellular radio module 241 of the sensor control device 110 can malfunction or otherwise fail to operate as expected. The communication module 240 of the sensor control device 110 can include modules or transceivers to facilitate efficient short-range communication (e.g., NFC, BLE, etc.). The dedicated data receiving device 120, multi-purpose data receiving device 130, and/or user device 140 can include a paired module for communication with the sensor control device 110. The paired device can act as a relay or bridge for the sensor control device 110 to ensure that the sensor control device 110 can communicate with the remote cloud server 150. Additionally or alternatively, the dedicated data receiving device 120 can be communicatively coupled to a proprietary application executing on a multi-purpose data receiving device 130 and/or user device 140 as a backup means of communicating to the remote cloud server 150 in the event that the dedicated data receiving device 120 is incapable of connecting to a suitable network. For example, the cellular radio module 341 and/or WiFi module 346 of the dedicated data receiving device 120 can malfunction. A short-range communication module (e.g., NFC module 343, BLE module 342, etc.) can be used to connect with the multi-purpose data receiving device 130 or user device 140. The multi-purpose data receiving device 130 or user device 140 can be used as a relay or bridge for the dedicated data receiving device 120 to ensure that the dedicated data receiving device 120 can communicate with the remote cloud server 150.

If the user device 140 supports short-range communication, an application provided by the operator of the medical monitoring system 100 can ensure that the short-range communication remains secure. Data transmitted between any two devices of the medical monitoring system 100 can be protected using a proprietary authentication and encryption scheme. In general, the two devices must first be authenticated to each other (e.g., by confirmation of secret keys) and can agree on an encryption key for data transmission. For example, the encryption key can include random and context-dependent values to reduce the risk to data interception. In certain embodiments, the level of encryption required can scale with the computing power and device battery capacity of the two devices. For example the communication session between a dedicated data receiving device 120 or user device 140 and the remote cloud server 150 can use a more computationally-intensive encryption scheme than a communication session between the sensor control device 110 and the remote cloud server 150. This can also reflect the risks inherent to the data that can be transmitted between the devices. For example, the user device 140 and dedicated data receiving device 120 can provide access to a broader picture of the health of the user 170, while the sensor control device 110 can provide only a limited snapshot of the medical data of the user and can provide data in a format that is only useful to the remote cloud server 150, reducing the effect of the risk of exposure or interception.

As described herein, the dedicated data receiving device 120 and user device 140 can have increased processing power or capabilities compared to sensor control device 110 and can therefore engage in more robust data security approaches in transmitting the data to the remote cloud server 150. The communication exchanges between the dedicated data receiving device 120 or user device 140 and the remote cloud server 150 can involve exchanges and confirmation of the data transmitted. As embodied herein, prior to the data transmitted between the remote cloud server 150 and other devices personally identifying information for the patient 140 can be removed from the data, encrypted, or otherwise obscured to anonymize the data. The receiving device can associate that data back with the user 140 (if needed) using other information, e.g., an authentication token used to connect to the cloud server 150 or identifying information for the receiving device. Furthermore, data can be compared against previously-received data to ensure that the data is not a duplicate of another data set.

Not illustrated is the manufacture of the devices used throughout the data flow illustrated in FIG. 4, including the sensor control device 110, dedicated data receiving device 120, as well as software or application programming interfaces that can be used by or with the remote cloud server 150, multi-purpose data receiving devices 130, and other user device 140. The manufacturer can choose to provide the information and programming necessary for the devices to securely communicate through secured programming and updates (e.g., one-time programming, encrypted software or firmware updates, etc.). For example, the manufacturer can provide information that can be used to generate encryption keys for each device, including secured root keys for the sensor control device 110 and optionally for the dedicated data receiving device 120 that can be used in combination with device-specific information and operational data (e.g., entropy-based random values) to generate encryption values unique to the device, session, or data transmission as need. The manufacturer can imbue each sensor control device 110 with a unique identifier ("UID") and other identifying information, such as an identifier for the manufacturer, identifier for the communication module and manufacturer, or any other suitable identifying information for the sensor or sensor components. As an example, the UID can be derived from sensor-unique data, such as from a serial number assigned to each ASIC 200 embodied in the sensor control device 110 by the ASIC vendor, from a serial number assigned to a communication module 240 embodied in the sensor control device 110 by a communication module vendor, from a random value generated by the sensor manufacturer, etc. Additionally or alternatively, the UID can also be derived from manufacturing values including a lot number for the sensor control device 110 or its components, a day, date, or time of manufacturer of the sensor control device 110 or its key components, the manufacturing location, process, or line of the sensor or its key components, and other information that can be used to identify when and how the sensor was manufactured. The UID can be accompanied by encryption keys and several generated random values that are also unique to each sensor control device 110. Similar processes can be used to establish the secure identity of the dedicated data receiving device 120.

As described herein, the medical monitoring system 100 can support the use of low-latency cellular networks (e.g., 5G) as a communication medium between a sensor control device 110 and the remote cloud server 150 or between a dedicated data receiving device 120 and the remote cloud server 150. Thus, the sensor control device 110 and dedicated data receiving device 120 can communicate with the remote cloud server 150 through the use of public networks (or a combination of public and private networks) without requiring an intermediary device of the medical monitoring system 100 to interpret, process or otherwise facilitate communication of the data. The use of low-latency cellular networks can be particularly advantageous in the context of medical monitoring because the involved devices can maintain a consistent connection with the remote cloud server 150 and offload significant processing requirements to the more powerful remote cloud server 150 without losing the benefits of on-device processing such as providing instantaneous alerts to the user. Furthermore, the consistent connection between the remote cloud server 150 and other devices can facilitate rapid data sharing between a patient, a physician, and other users of the medical monitoring system 100 that have been authorized to receive informational messages and/or alerts on behalf of the patient (e.g., family members). Additionally or alternatively, the remote cloud server 150 can determine and issue sensor control device 110 reconfiguration instructions to the sensor control device 110 based on data received from the sensor control device 110 and/or instructions from, for example, an authorized physician.

The sensor control device 110 can communicate with the remote cloud server 150 on a frequent and regular basis to provide sensitive data (e.g., medical data) for processing by the remote cloud server 150. As an example only and not by way of limitation, the sensor control device 110 can communicate with the remote cloud server 150 such as every 30 seconds, every minute, every two minutes, every five minutes, every fifteen minutes, etc. The rate of communication and other transmission parameters, between the sensor control device 110 and remote cloud server 150 can be moderated based on the communication network status available to the sensor control device 110, the rate of data generation (e.g., sampling rate), and power consumption. In cases where the sensor control device 110 is expected and able to send consistent updates to the remote cloud server, the memory 220 of the sensor can store the data collected until the sensor control device 110 is able to connect to an appropriate network and offload the data to the remote cloud server 150. The sensor control device 110 can further communicate with the remote cloud server 150 to provide different types of information on a less frequent basis, such as information with a lower urgency or necessity of constant reporting. For example, the sensor control device 110 can communicate status information of the sensor control device 110 such as the remaining battery levels of the sensor control device 110 once per day.

As embodied herein, the sensor control device 110 has a relatively consistent connection with the remote cloud server 150, and thus the on-device processing capabilities of the sensor control device 110 can be simplified, which can reduce the cost of manufacturing the sensor control device 110 and to improve the battery life of the sensor control device 110. Instead, the medical monitoring system 100 can rely on the remote cloud server 150 to perform the bulk of processing. The remote cloud server 150 can in turn be configured to perform the processing of the data reported by the sensor control device 110, for example determining levels of an analyte based on raw signals reported by an analog-to-digital converter of the sensor control device 110. As described herein, the remote cloud server 150 can process data received from the sensor control device 110 to identify values of immediate concern (e.g., detected analyte levels are presently outside of normal or safe ranges). The remote cloud server 150 can store the data received from the sensor control device 110 to enable historical evaluation and identify short and long term trends in the data. For example, the remote cloud server 150 can determine whether analyte values are currently within a safe range, but are trending outside of the range or can determine whether the user's management of the analyte levels has become more or less consistent over a long period of time.

The medical monitoring system 100 can provide the data for review by one or more users through a variety of interfaces. For example, a user of the medical monitoring system 100 can configure a dedicated data receiving device 120 or multi-purpose data receiving device 130 to receive alerts and updates from the remote cloud server 150 based on data provide by the sensor control device 110 to the remote cloud server 150. As another example, the medical monitoring system 100 can provide a website, web portal, or application programming interface ("API") through which a user can access detailed analysis of data reported by a sensor control device 110 to the remote cloud server 150. The web portal and API can ensure that data is highly accessible to the user or any other authorized user from any compatible device configured to use the API or even with a web browser. Therefore, the remote cloud server 150 can greatly expand the number of authorized users who can assist in monitoring the medical status of a patient, especially when the patient is otherwise in capable of reviewing the medical status reported by their sensor control device 110. For example, an athlete can be wearing a sensor control device 110 while competing and be distracted, even if the remote cloud server 150 instructs that alerts should be provided to the patient. The athlete can configure one or more observers (e.g., a coach) to be an authorized recipient of alerts on their behalf. Additionally, the athlete's physician can be notified of medical events while the athlete is competing. This instantaneous data sharing can be beneficial to allow patients and caregivers to identify conditions and make treatment decisions in real-time, which can provide an improvement over prior systems involving communication between the sensor control device 110 and other local intermediary devices for processing.

In addition to reviewing the data from a sensor control device 110 associated with a patient, authorized users can issue instructions based on the data. The instructions can, for example, relate to altering the performance of a sensor control device 110, dedicated data receiving device 120, or the remote cloud server 150 with respect to how data is collected by and from the sensor control device 110, how information based on the data is provided to one or more users, and how the data is processed by the remote cloud server. As embodied herein, a physician can review data from a sensor control device 110 and determine that changes relating to the performance of the sensor control device 110 should be altered based on her analysis of the data. The physician can enter instructions into a portal of the remote cloud server 150. The remote cloud server 150 can give the instructions effect. For example, the physician can determine that, based on data trends, the sensor control device 110 should perform readings and report medical data more frequently over the next 24 hour period. The remote cloud server 150 can use its connection with the sensor control device 110 to issue reconfiguration instructions to cause the sensor control device 110 to more actively gather medical data (e.g., analyte levels) and transmit the medical data to the remote cloud server 150. Additionally or alternatively, the remote cloud server 150 can be authorized to issue certain types of device reconfiguration instructions automatically based upon algorithmic analysis of reported data and/or comparison of a detected state of the sensor control device 110 and/or patient to a previously detected state where a physician issue a device reconfiguration instructions. Continuing the previous example, the remote cloud server 150 can, after the 24 hour period has completed, re-evaluate the current trend information and determine that whatever condition of condition was detected by the physician has abated. The remote cloud server 150 can then issue instructions to the sensor control device 110 to cause the sensor control device 110 to return to previous operating modes to preserve the device battery.

Some medical monitoring systems use on-device processing, also referred to as edge processing, to analyze and provide notifications to users based on the results of measurements from a sensor. For example, such a sensor can include sufficient computational capabilities to perform interpretation and detection algorithms related to the medical function of the sensor. In other embodiments, such a sensor can pair with a data receiving device (which can include a dedicated device or a multi-purpose device) which would perform the requisite processing and function as a location for the delivery of notifications. Remote cloud servers in such systems often acted merely as historical data repositories and as a way to enhance the storage capabilities of sensors and data receiving devices, which would necessarily be limited by the cost to provide for effective long-term storage solutions. The embodiments described herein provide a significant advancement over prior systems at least because the sensor control device 110 is capable of directly offloading additional processing requirements to the more computationally-powerful and computationally-efficient remote cloud server 150 without detracting from the ability to provide immediate access to the medical data and related notifications.

As described herein, the sensor control device 110 of the medical monitoring system 100 have simplified or can be free of interfaces for standard user input. However, to allow a user of the medical monitoring system 100 to be able to determine when to activate the sensor control device 110 and to associate the sensor control device 110 (and the data received therefrom) with their records within the medical monitoring system 100 in order to review their medical data, the disclosed subject matter provides examples of components and techniques for activating and authenticating a cost-effective medical sensor in a direct-to-cloud medical monitoring system.

In one embodiment, the sensor control device 110 can be provided to an end-user in a deactivated or low-power (e.g., sleep) state. The sensor control device 110 can be automatically activated (e.g., transitioned from the deactivated or low-power state to an activate or awake state) once applied to the user using a suitable applicator. The sensor control device 110 can be manually activated through the use of a physical interface on the sensor such as a button or tab. For example, the sensor control device 110 can be shipped with a tab that creates a barrier between the leads of a battery and the sensor control device 110 itself. The sensor control device 110 can then be activated when the tab is pulled. As another example, the sensor control device 110 can include a button that sends an interrupt signal to the ASIC 200 of the sensor control device 110. The interrupt signal can be interpreted by the ASIC 200 in a context-dependent manner. One of the interpretations can be a command to instruct the sensor control device 110 to transition to an active state. As another example, the sensor control device 110 can include a light sensor that is configured to produce electrical signals to send interrupt signals to the ASIC 200 upon exposure to light (e.g., to detect when the sensor control device 110 has been removed from its packaging) or upon exposure to certain wavelengths and/or intensities of light.

Once activated, the sensor control device 110 can attempt to connect to a wide area network or cellular network compatible with its communication module 240. If the sensor control device 110 is able to connect to the network, the sensor control device 110 can communicate with the remote cloud server 150 (the address of which can be preprogrammed into the memory of the sensor control device 110). The initial communication from the sensor control device 110 can include at least enough information for the sensor control device 110 to identify itself to the remote cloud server 150, such as a unique identifier for the sensor control device 110. For example, in cases where the sensor control device 110 is activated as a part of the process of being applied to a user, the sensor 150 can automatically begin collecting medical data. In certain embodiments, the sensor control device 110 can delay sending any medical data to the remote cloud server 150 until instructed to do so by the remote cloud server (e.g., once the sensor control device 110 has been authenticated as described below). In other embodiments, the sensor control device 110 can send medical data to the remote cloud server 150, but it can be held by the remote cloud server 150 and not associated with any particular user until authentication has completed.

The sensor control device 110 can be provided with a unique identifying code (UID), e.g., printed, stamped, or labeled to the sensor itself, an applicator for the sensor, packaging for the sensor, or in other materials provided with the sensor (e.g., an insert card in the packaging) or provided by a medical professional. For example, a prescribing doctor or administering nurse can provide the UID to the user. As another example, the medical professional can receive the UID and can go through the steps of activating and authenticating the sensor control device 110 on the patient's behalf using the UID. The UID can be provided in the form of a human-readable code (e.g., a multi-value alphanumeric code), a machine-readable code (e.g., a 2D barcode, matrix barcode, etc.), or both.

The user can be instructed to provide the UID to the remote cloud server 150 after the sensor control device 110 has been activated. For example, the user can access the remote cloud server 150 through a dedicated data receiving device 120 that has already been authenticated to be associated with the user's medical data. The user can additionally or alternatively access the remote cloud server 150 through an application executing on a user device 140, through an API provided by the operator of the medical monitoring system 100, through a website or web portal associated with the medical monitoring system 100, etc. Upon logging in, the user can be shown a list of sensors 110 associated with their account. The user can be provided a user interface element into which the user can enter an identification code associated with the sensor control device 110. The user can then provide the UID for the sensor control device 110 to the remote cloud server 100. If the UID is a human-readable code, the user can be provided a field through which to enter the UID (e.g., a virtual or physical keyboard associated with a text entry field). Additionally or alternatively, the user can use a camera or similar input function of the dedicated data receiving device 120 or user device to scan a machine-readable code for entry into a suitable user interface. The UID can then be provided to the remote cloud server 150 from the dedicated data receiving device 120 or user device 140.

Once the remote cloud server 150 receives the UID from the user, the remote cloud server 150 can compare the UID to the identifier provided by the sensor control device 110. If the remote cloud server 150 is able to identify a recently-activated sensor control device 110 with a corresponding UID, the remote cloud server 150 can associate that sensor control device 110 with the user in the medical monitoring system. The remote cloud server 150 can indicate to the user and to the sensor control device 110 that has been successful. The sensor control device 110 can be instructed to send medical data updates according to its schedule. If medical data had previously been sent by the sensor control device 110 that data can be processed by the remote cloud server 150 and associated with the user for viewing as part of the user's instantaneous or historical data. If the sensor control device 110 had been instructed not the send medical data to the remote cloud server 150 until authentication is completed, but has still be collecting medical data, the collected data can be provided, backfilling the historical data for the user.

Figure 5A:
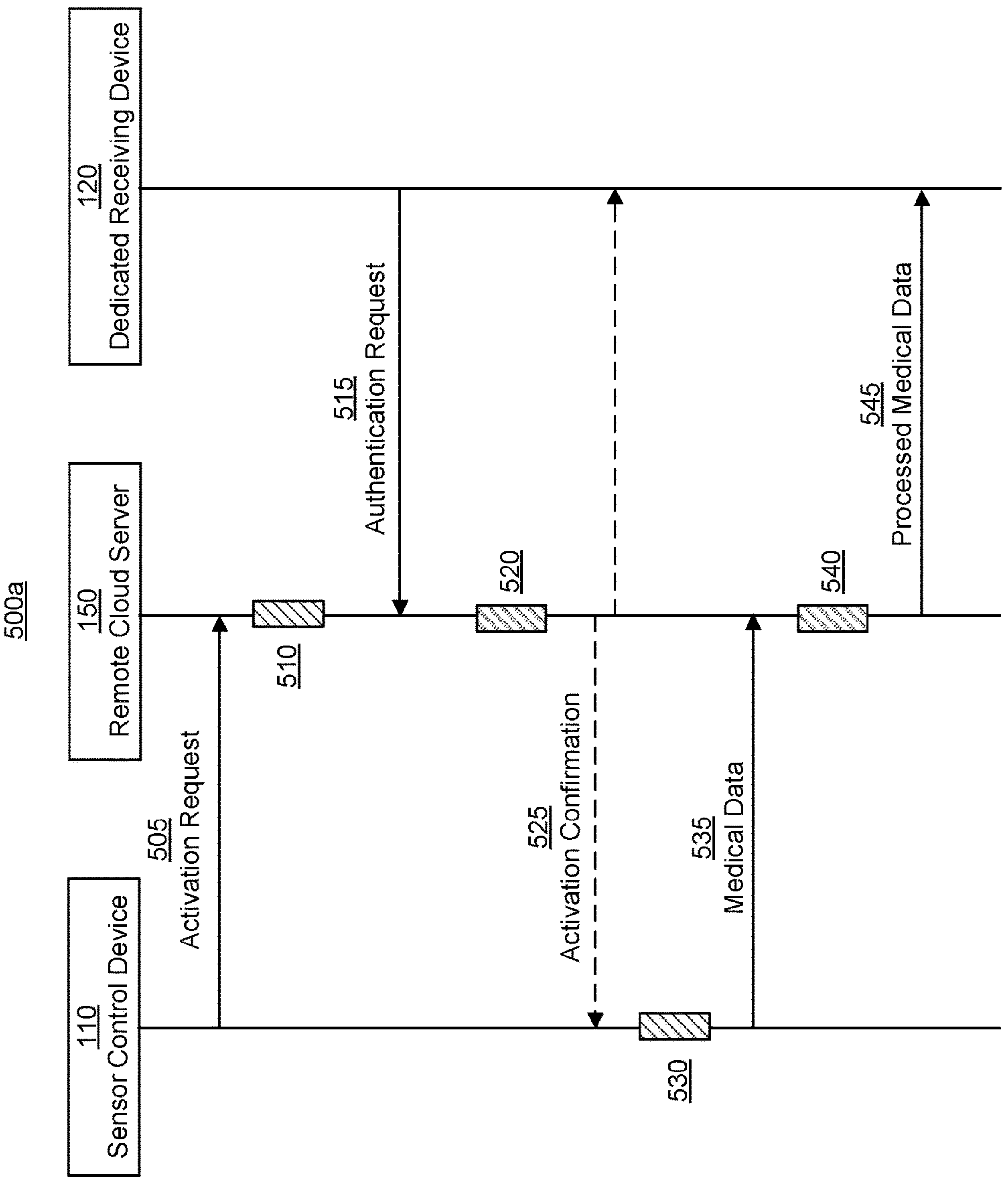
FIGS. 5A and 5B are diagrams illustrating an example operational and data flow activation of devices on the medical monitoring system according to the disclosed subject matter.

FIG. 5A is a diagram illustrating an example operational and data flow for activation of devices on the medical monitoring system according to the disclosed subject matter. In the process 500*a* illustrated in FIG. 5A, the activation/authentication procedure begins with a request from the sensor 120. The process 500*a* begins at 505, when a sensor control device 110 sends an activation request to a remote cloud server 150. The activation request can include associated information, such as a UID for the sensor control device 110 and contextual information such as the location of the sensor control device 110 at the time of sending the activation command. The activation request can be sent in response to the user activating the sensor (e.g., through a physical or other simple user interface) or applying the sensor control device 110. At 510 the remote cloud server 150 stores the activation command and associated information in an associated data store. At 515, the dedicated data receiving device 120 sends an authentication request to the remote cloud server 150. The authentication request can also include associated information, such as the UID of the sensor control device 110, an identifier for the user of the dedicated data receiving device 120, an identifier for the dedicated data receiving device 120, and contextual information. At 520, the remote cloud server 150 compares the information from the activation request and the authentication request. If the remote cloud server 150 identifies a correspondence between the sensor control device 110 and the dedicated data receiving device 120 (e.g., based on the activation request and authentication request both including the same UID or otherwise being associated with the same user), at 525 the remote cloud server 150 can optionally send an activation confirmation to one or both of the sensor control device 110 and the dedicated data receiving device 120. Additionally or alternatively, the remote cloud server 150 can compare the context information associated with the activation request and authentication request to determine whether the activation request and authentication request are likely to be related. As an example, the remote cloud server 150 can determine whether there is a substantial match between the location associated with the activation request and the authentication request or a substantial match between the times associated with the activation request and the authentication request. The activation confirmation can be a final opportunity for the user to verify the sensor control device 110 that they wish to associate with their data. If the sensor control device 110 is configured to receive an activation confirmation, the sensor control device 110 can begin collecting medical data at 530. In certain embodiments, the sensor control device 110 can begin collecting medical data as soon as the activation request is sent at 505 to ensuring that the maximum amount of medical data is being collected. At 535, the sensor control device 110 sends collected medical data to the remote cloud server 150 for additional processing. The sensor control device 110 can continuously collect and send the medical data as the battery life and communication status of the sensor control device 110 are maintained. The collected medical data can be provided in a raw measurement form that can be used with additional processing to provide a result, such as an analyte level, that is more useful to the user, as described herein. At 540, the remote cloud server 150 processes the data received from the sensor control device 110. Processing the data can involve converting the data received from the sensor control device 110 into a more useful format or representation for the user. Processing the data can also involve generating trends, recommendations, or other analyses for the user based on the medical data. At 545 the remote cloud server 150 provides the processed medical data to the dedicated data receiving device 120 for review by the user.

The order of activation can be reversed in some embodiments. Rather than requiring that the sensor control device 110 be activated first followed by authentication by the user, the medical monitoring system 100 can support the user triggering activation by entering a UID or merely requesting a new sensor control device 110 to be activated. For example, the user can first enter the UID provided with the sensor control device 110 into the application or website as previously described. This can prime the remote cloud server 150 to expect the sensor control device 110 with the corresponding UID to being sending data. Additionally, if the sensor control device 110 is already connected to a wide area network, the remote cloud server 150 can attempt to send instructions to the sensor control device 110. The instructions can cause the sensor 1110 to provide some indication to the user that the sensor control device 110 has been activated (e.g., emit a particular sound or light) before the user applies the sensor control device 110.

Figure 5B:
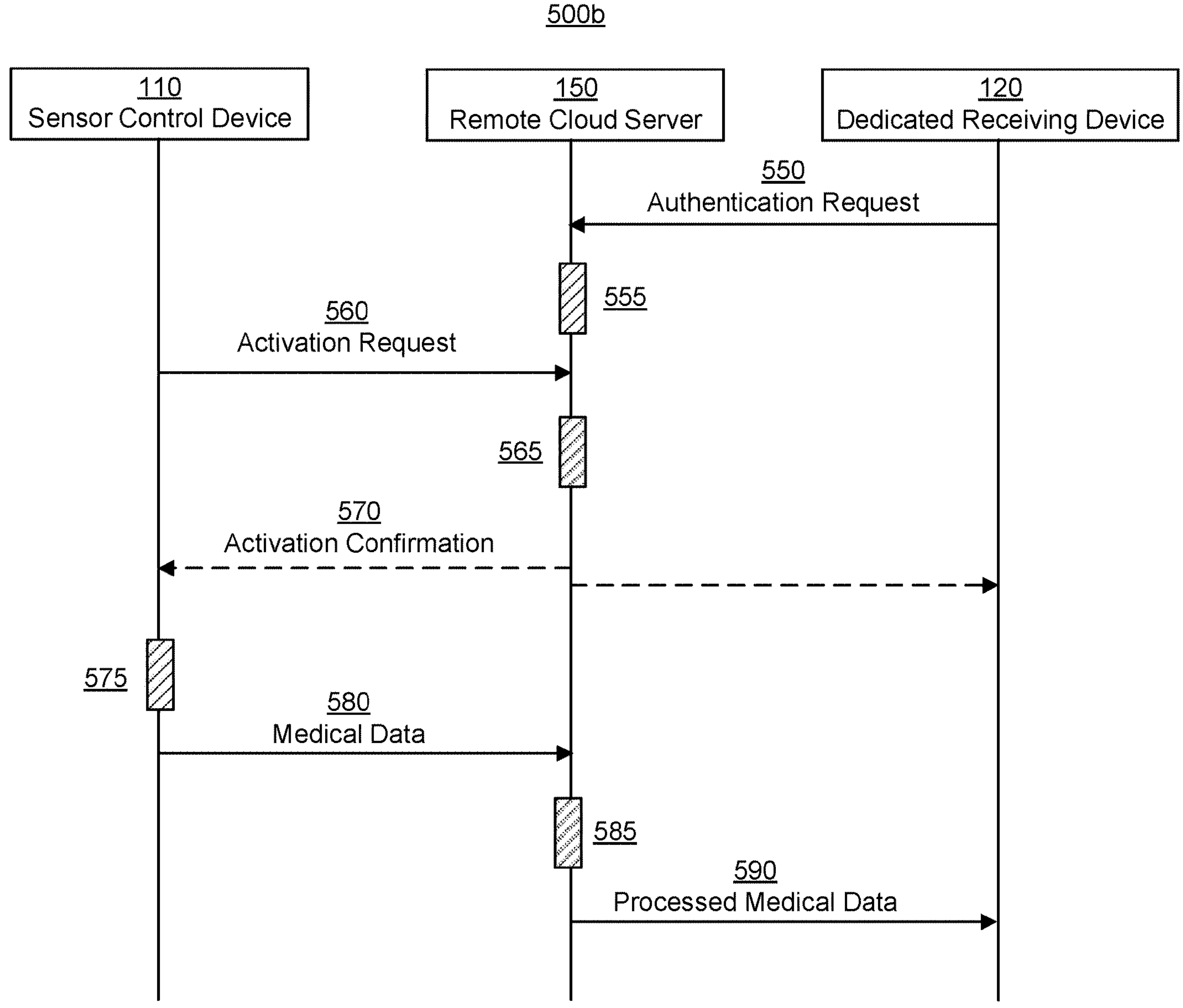

FIG. 5B is a diagram illustrating an example operational and data flow for activation of devices on the medical monitoring system according to the disclosed subject matter. In the process 500*b* illustrated in FIG. 5B, the activation/authentication procedure begins with a request from the dedicated data receiving device 120. The process 500*b* begins at 550, when the dedicated data receiving device 120 sends an authentication request to the remote cloud server 150. The authentication request can include associated information, such as the UID of a sensor control device 110 that the user associated with the dedicated data receiving device 120 plans to use, an identifier for the user, an identifier for the dedicated data receiving device 120, and contextual information. At 555 the remote cloud server 150 stores the authentication request and associated information in an associated data store. At 560, a sensor control device 110 sends an activation request to the remote cloud server 150. The activation request can also include associated information, such as a UID for the sensor control device 110 and contextual information such as the location of the sensor control device 110 at the time of sending the activation command. The activation request can be sent in response to the user activating the sensor (e.g., through a physical or other simple user interface) or applying the sensor control device 110. At 565, the remote cloud server 150 compares the information from the activation request and the authentication request. If the remote cloud server 150 identifies a correspondence between the sensor control device 110 and the dedicated data receiving device 120 (e.g., based on the activation request and authentication request both including the same UID or otherwise being associated with the same user), at 570 the remote cloud server 120 can optionally send an activation confirmation to one or both of the sensor control device 110 and the dedicate data receiving device 120. The activation confirmation can be a final opportunity for the user to verify the sensor control device 110 that they wish to associate with their data. If the sensor control device 110 is configured to receive an activation confirmation, the sensor control device 110 can begin collecting medical data at 575. In certain embodiments, the sensor control device 110 can begin collecting medical data as soon as the activation request is sent at 560 to ensure that the maximum amount of medical data is being collected. At 580, the sensor control device 110 sends collected medical data to the remote cloud server 150 for additional processing. The sensor control device 110 can continuously collect and send the medical data as the battery life and communication status of the sensor control device 110 are maintained. The collected medical data can be provided in a raw measurement form that can be used with additional processing to provide a result, such as an analyte level, that is more useful to the user, as described herein. At 585, the remote cloud server 150 processes the data received from the sensor control device 110. Processing the data can involve converting the data received from the sensor control device 110 into a more useful format or representation for the user. Processing the data can also involve generating trends, recommendations, or other analyses for the user based on the medical data. At 590 the remote cloud server 150 provides the processed medical data to the dedicated data receiving device 120 for review by the user.

Although FIG. 5A and FIG. 5B illustrate the process involving the dedicated data receiving device 120, another user device 140 can be substituted for the dedicated data receiving device 120 without departing from the teachings of the embodiments described herein. In another embodiment, the user can request a new sensor control device 110 to be paired to their data in the medical monitoring system 100 and provide their location with the request. The medical monitoring system 100 can monitor sensor activations, which can also be provided with approximate locations depending on how the sensor control device 110 is connecting with the medical monitoring system, for sensor activations that are near the provided location. Upon detecting a nearby activation, the medical monitoring system 100 can prompt the user for confirmation by merely asking the user to compare the UID of the sensor control device 110, rather than enter the entire UID. The medical monitoring system can support multiple approaches for activating and authenticating sensors according to patient preferences.

If the remote cloud server 150 is unable to authenticate the sensor control device 110, the user can receive a notification from the medical monitoring system 100 and/or from the sensor control device 110 directly. For example, the user can receive a notification via a device associated with the user through the medical monitoring system or receiving a notification message via an additional communication channel (e.g., SMS, email) that indicates that an attempt to activate and authenticate a sensor has been made and failed. Similarly the sensor control device 110 can provide an indication such as an error tone or alert light indicating that authentication was not successful. The user can re-attempt to authenticate the sensor control device 110, use an additional authentication method, or can attempt to use a new sensor control device 110.

The dedicated data receiving device 120 can have access to significant medical history information of the user and can also be a principle component of the direct-to-cloud medical monitoring system 100, and as such, authentication of the dedicated data receiving device by a user can be required by the system 100 before the user's account information can be accessed. In certain embodiments, the dedicated data receiving device 120 includes a standard login interface through which a user can enter, for example, a user identifier and password, in order to access information stored by the remote cloud server 150. In the interest of patient security, the medical monitoring system 100 can provide for a multi-device authentication method through which a user can securely authenticate the dedicated data receiving device 120.

Figure 6:
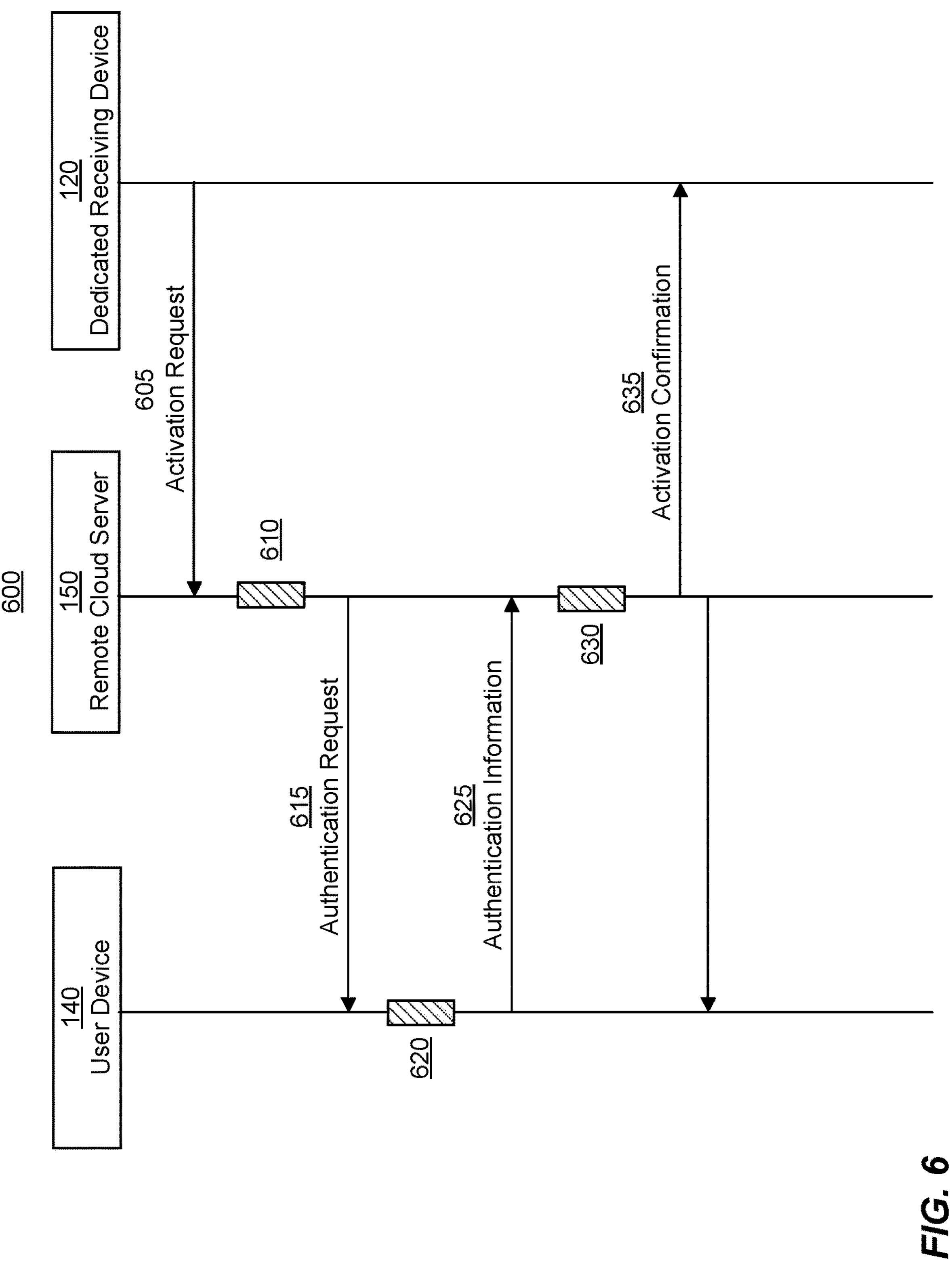
FIG. 6 is a diagram illustrating an example operational and data flow activation of devices on the medical monitoring system according to the disclosed subject matter.

FIG. 6 is a diagram illustrating an example operational and data flow for activation of a dedicated data receiving device 120 on the medical monitoring system according to the disclosed subject matter. In the process 600 illustrated in FIG. 6, the activation/authentication procedure begins with a request from the dedicated data receiving device 120. At 605, the dedicated data receiving device 120 sends an activation request to the remote cloud server 150. The activation request can include associated information, such as a UID for the dedicated data receiving device 120 and contextual information such as the location of the dedicated data receiving device at the time of sending the activation command. The activation request can also include an identifier for the user to whose account the activation request seeks to grant access. As described herein, the activation request can be sent as directed by the user of the dedicated data receiving device. At 610 the remote cloud server 150 stores the activation command and associated information in an associated data store. At 615, remote cloud server 150 sends an authentication request to a user device 140. The authentication request can be in the form of a notification sent through an application executing on the user device 140 (e.g., an application associated with the medical monitoring system 100) or can be sent via one or more typical communication channels such as email or SMS. The authentication request can alert the user that a dedicated data receiving device is pending activation. The authentication request can further include a code associated with the activation request, which can be further distinct from an identifier of the dedicated data receiving device.

At 620, the user device 140 receives confirmation from the user via a user interface of the user device. The confirmation can include a confirmation of an identifier for the dedicated data receiving device 120 which the user has requested to add. At 625, the user device 140 sends authentication confirmation information to the remote cloud server 150. The authentication confirmation information can include the identifier entered by the user at step 620 as well as additional contextual information such as the location of the user at the time of entering or accepting the activation request. At 630, the remote cloud server 150 compares the information from the activation request and the authentication information. If the remote cloud server 150 determines that the activation request is valid, (e.g., through a correspondence between the identifier of the dedicated data receiving device 120 and the identifier provided in the authentication information) and the dedicated data receiving device 120 (e.g., based on the activation request and authentication request both including the same UID or otherwise being associated with the same user), at 635 the remote cloud server 150 can send an activation confirmation to one or both of the user device 140 and the dedicated data receiving device 120. The remote cloud server 150 can begin to provide access to the user's medical data through the dedicated data receiving device 120 and can use the dedicated data receiving device to provide alerts, notifications, and other information the user.

As described herein, the medical monitoring system 100 makes use of the availability of reliable cellular networks to ensure that the sensor control device 110 is able to maintain connections with the medical monitoring system 100, and in particular to continuously send medical data to the remote cloud server 150, even when wide area networking is not available. Even if supplemented by the sensor control device 110 taking advantage of certain wireless local area networks, network coverage cannot be assumed to be universal. In particular, some geographic regions are not covered by cellular networks (e.g., due to low population density). Some areas can be prone to outages and spotty coverage. Occasionally a user can be unable to avoid scenarios were the sensor control device 110 can be temporarily disconnected from all networks (e.g., driving through along tunnel, entering an elevator, etc.). Therefore, the medical monitoring system 100 can optionally include fallback provisions to provide for backup communication between the sensor control device 110, the remote cloud server 150, and, ultimately, the user so that the user can be notified of moment-to-moment changes in their health.

First, the medical monitoring system 100 can proactively identify areas of high impact for additional cellular network coverage. For example, the operator of the medical monitoring system 100 can identify regions where users who have been invited or instructed to use the medical monitoring system 100 are likely to be underserved by commercial cellular networks. The operator can compare de-identified locations of subscriptions and prescriptions to maps of cellular network coverage. The operator can identify locations of sensor activations and locations associated with other devices in communication with the medical monitoring system 100. After identifying gap areas, the operator can install or request installation of additional cellular network compatible devices and hotspots in those areas. In addition, the operator can offer devices to users of the medical monitoring system that simulate a cellular network connection (at least from the perspective of the sensors 110) by offering a wireless connection that coordinates with home or office internet available to the user. Therefore, a user can supplement their own connection to the medical monitoring system 100 without losing the advantages and convenience of all-wireless communication.

The medical monitoring system 100 can monitor a communication status of the sensor control device 110 and alert the user when connectivity with the sensor control device 110 is lost or when it appears likely that connectivity can be lost soon. For example, as part of device status information that can be sent by the sensor control device 110 to the remote cloud server 150 on a regular basis, the sensor control device 110 can include a network connection strength or other identifying information for the network(s) to which the sensor control device 110 is connected. The remote cloud server 150 can track network status to predict future network status. If the remote cloud server 150 detects that the sensor control device 110 is disconnected, the remote cloud server 150 can push a notification to the user through the users devices registered to the medical monitoring system. The notification can include sending a notification to a dedicated data receiving device 120 or other user device 140. The notification can also include sending a SMS message or email to the user via registered addresses presented by the user. The notification can include such information as the time that the sensor control device 110 disconnect was detected, the duration of the disconnection, the last-known location of the sensor control device 110, and other related information. If the notification is of a predicted disconnect, the notification can be sent to the sensor control device 110 itself if the sensor control device 110 is configured to provide notifications as described herein. A low-network connection alert can then be activated by the sensor control device 110. The threshold for detecting when a low-network alert should be sent by the remote cloud server 150 can be adjustable and customized for individual users and sensors according to their typical network environment. Additionally, the threshold amount of time that triggers a notification of sensor disconnect is adjustable and can be customized based on, for example, the typical network status of the user's environment, the type of medical data collected, the amount of storage available to the sensor control device 110, and other related information.

When the sensor control device 110 is unable to communicate with the remote cloud server 150 (e.g., because of a network outage, scheduled or unscheduled unavailability, etc.) the sensor control device 110 can be configured to hold a predetermined about amount of medical data within its on-device storage 230. Then, once the connection is restored, the sensor control device 110 can upload the stored medical data to the remote cloud server 150. The sensor control device 110 can upload the data with a priority scheme in mind. For example, the sensor control device 110 can upload a set amount of most recent data first, to facilitate the remote cloud server 150 processing the user's current health status. The sensor control device 110 can then provide older medical data stored by the sensor control device 110 to the remote cloud server 150 to facilitate deeper trend analysis by the remote cloud server 150.

Additionally, the medical monitoring system 100 can provide for backup communications between the sensor control device 110 and other devices within the medical monitoring system 100, such as the dedicated data receiving device 120, multi-purpose data receiving device 130, and/or user device 140. As described herein, in addition to a cellular radio module 241, the sensor control device 110 can include other communication sub-modules to enable backup communications. For example, the communication module 240 of the sensor control device 110 can include an NFC module 243 to enable the sensor control device 110 to communicate data with a more powerful intermediary device (including a dedicated data receiving device 120 or other user device 140) that can either maintain a cellular network connection, connect to another network and/or through another communication channel, or perform on-device processing to provide rudimentary analysis for the sensor control device 110. The NFC module 243 can be selectively activated by bringing the sensor control device 110 in close proximity to the intermediary device. The intermediary device can provide power to the NFC module 243 while in a close range, meaning that the NFC module 243 can have a limited impact on the power levels of the sensor control device 110. Alternatively, or in addition, to the NFC module 243, the communication module 240 can include a BLE module 242 to be selectively activated when the cellular radio module 241 is unable to connect to cellular networks. The communication module 240 can use the BLE module 242 to connect with an intermediary device which can supplement the connection to the remote cloud server 150 or perform local and on-device processing. As embodied herein, the intermediary device can include a dedicated data receiving device 120, multi-purpose data receiving device 130, or user device 140 that is connected with remote cloud server 150 through, e.g., a cellular radio module and/or WiFi module. The intermediary device can include a dedicated data receiving device 120 or multi-purpose data receiving device 130 that is connected to a user device (e.g., laptop or personal computer) via a wired connection (e.g., through a USB module), which is in turn connected with the remote cloud server 150 through a wired or wireless connection. Additionally or alternatively, the NFC module described above and/or a USB module can be incorporated to provide backup access, even if the sensor control device 110 battery level is critically low.

As described herein, the cellular radio module 241 of the sensor control device 110 can be used to identify the location of a wearer in the event of emergencies or at the request of the patient or one or more authorized users. Cellular communication enables for the determination of an approximate location of a cellular transceiver. In particular, through the use of techniques such as cellular-tower triangulation, the location of a compatible device can be determined, even without the assistance of a hardware dedicated to resolving the location of a device (e.g., GPS). In particular, 5G communication technologies can significantly increase resolution and accuracy of location determinations. These location-determination techniques can be used to, for example determine the location of a patient during a medical, or other, emergency. The patient can activate a feature of the sensor control device 110 (e.g., actuate a button) requesting assistance. Upon receiving a notice of activation of the feature, the sensor control device 110 can resolve its location using, for example, the cellular radio module 241. Additionally or alternatively, the sensor control device 110 can transmit the request for assistance to the remote cloud server 150. The remote cloud server 150 can then apply location determination algorithms to signals received from the sensor control device 110 and determination an approximate location of the sensor control device 110. The remote cloud server 150 can further initiate other actions using the approximate location (e.g., determined by the sensor control device 110 or remote cloud server 150). For example, the remote cloud server 150 can send a request to the patient to confirm their approximate location. As another example, the remote cloud server 150 can send a notice of the request for assistance to one or more users authorized by the patient (e.g., physicians, trusted or emergency contacts). As another example, the remote cloud server 150 can automatically (and/or based on an explicit patient request) contact emergency services, report the request for assistance, the approximate location, and/or a summary of a medical event that the patient is possibly experiencing based on recently received data from the sensor control device 110. The request for assistance can be initiated automatically by the remote could server 150 based on algorithmic analysis of the sensor data. For example, if the sensor control device 110 includes medical hardware to determine analyte levels of the patient, the remote cloud server 150 can initiate emergency assistance activities based on analysis of the analyte levels indicating that the patient may be experiencing unsafe levels of the analyte. As another example, if the sensor control device 110 includes medical hardware to determine the heart rate of the sensor control device 110, the remote cloud server 150 can initiate emergency assistance activities based on determining that the heart rate is suddenly dangerously low or dangerously high.

In addition to using an approximate location of the sensor control device 110 determined using the cellular radio module 241 for emergency events, the approximate location can be used to modify performance of the sensor control device 110, analysis of reported sensor data, and/or how data is communicated to the patient. As embodied herein, certain features of the sensor control device 110 can be selectively enabled and disabled based on geographic region. For example, certain categories of information can be blocked from being reported in a first country, while they are approved for use in a neighboring country. The remote cloud server 150 can determine an approximate location of the patient based on the location of the sensor control device 110 (as determined using the cellular radio module 241 described herein) and selectively enable or disable the reporting based on the location. Therefore, a single sensor control device 110 can be sold and features can be enabled or disabled as required based on location, rather than requiring multiple versions of the same sensor control device 110. As another example, when a patient is traveling, the approximate location of the user can be used to ensure that algorithm calculations are consistent and modified to account for changes in the patient's current time zone. Furthermore, localization of the sensor control device 110 can be used to determine, for example, the algorithms used to analyze reported medical data, a language used in providing information to the patient and/or authorized users, how certain information is presented to the user (e.g., remaining sensor life reported in days or hours), and other location-dependent features.

As described herein, the direct-to-cloud communication interface for medical data processing can allow for a simplified sensor design, including for example a reduced amount of on-device processing by the sensor control device 110, which can reduce the cost of manufacturing the sensors 110. As an additional benefit, the simplified electronics of the sensor control device 110 can also contribute to reduce cost and improve battery life. Components of the sensor control device 110, for example, an ASIC 200 or microcontroller 210 can be simpler, or potentially eliminated entirely, and thus sensor control device 110 can be configured to use less power supplied from the power module 250. This reduced power consumption can help offset any increased power consumption caused by the use of certain cellular radio modules 241. For example, certain iterations of 5G-compatible radios have a higher average power usage than BLE or NFC radios. The sensor control device 110 can be designed to counteract the effect of the increased power usage from the cellular radio module 241 while ensuring a cost-effective and convenient end-user experience. For example, the simplified ASIC 200 and other related hardware of the sensor control device 110 can be implemented in a reduced footprint within the sensor control device 110 itself. The overall size of the sensor control device 110 can thus be reduced, or alternatively, a larger battery (e.g., within the power module 250) can be included to extend the operating period of the sensor control device 110 having a similar size. As another example, the power module 250 can be designed to accommodate a rechargeable battery. With a rechargeable battery, the maximum operating lifecycle of the sensor control device 110 is tied more to the operating lifecycle of the medical hardware 260 (e.g., due to changes in patient comfort, sensor sensitivity, etc.). The sensor control device 110 for example, can include a port through which the battery can be recharged as needed. This can include for example, a USB port that can also serve as a form of providing for a USB connection as described herein. Additionally or alternatively, the sensor control device 110 can include wireless charging circuitry that can allow for the sensor battery to be recharged without the user needing to maintain a wired connection to a power source.

The sensor control device 110 can be programmed with power consumption regulating algorithms that can be used to manage the power consumption of the sensor control device 110 over time to ensure that the sensor control device 110 reaches its stated operating life expectancy (e.g., 1 week, 2 weeks, 1 month, etc.). For example, the sensor control device 110 can be configured to selectively activate and de-activate components of the communication module 240 to manage the power consumption of the communication module 240. When the communication module 240 is not active, e.g., not sending or receiving data, the communication module 240 can be transitioned to a low-power state to reduce power usage. The communication module 240 can re-activated after a set period of time to send and/or receive expected data. The transition to a low-power state can be managed programmatically and in response to contextual conditions. For example, power management instructions can be provided by the operator of the medical monitoring system 100. The power management instructions can be supplemented by the remote cloud server 150 in embodiments where the remote cloud server 150 can send instructions to the sensor control device 110. Power management instructions can also modify the transmission rate and power levels of the communication module to reduce the energy used while transmitting. The power management instructions can define a model for determining how energy is to be used. For example, the power management instructions can define time periods where the communication module 240 is instructed to use less energy such as when the user is expected to be sleeping (and thus is less likely to have their medical condition change suddenly) or working (and this is more likely to be within range of reliable cellular and Wi-Fi networks, so a lower transmission power is appropriate). The power management instructions can also provide for overrides to the low-energy use periods based on trends in the user's apparent health. For example, if the remote cloud server 150 determines that detected analyte levels are trending outside of an acceptable range, the sensor control device 110 can be instructed to prevent the communication module from entering the low-power state to ensure that the sensor control device 110 continues to provide data to the remote cloud server.

As embodied herein, the connection between the sensor control device 110, dedicated data receiving device 120, and remote cloud server 150 can be used to ensure compliance of the patient with safety protocols of the medical monitoring system 100. For example, the operator of the medical monitoring system can issue product recommendations and/or recalls for certain devices (e.g., sensors 110 or dedicated data receiving devices 120). The operator can provide notice of the recommendations to physicians who are then tasked with ensuring compliance by their patients. The operator can provide notice to patients directly (e.g., through contact information received during product registration). However, both of these approaches involve the patient correlating the recommendations with their own devices and behaviors. Using the medical monitoring system 100 embodied herein, the operator can ensure compliance with product recommendations, such as usage recommendations, expiration dates, etc. For example, the operator can associate certain sensor model numbers or serial numbers with recall procedures and/or recommendations regarding the operator of the sensor control device 110. The operator can issue notifications to patients associated with sensors that match the model numbers or serial numbers. The operator can further enforce the product recalls automatically, for example, by disallowing continued use of recalled sensors and issuing replacement sensor to the affected patients. The operator can also enforce recommendations relating to sensor operation by issuing software or firmware updates and/or updates to sensing parameters as described herein.

Another embodiment of the medical monitoring system 100 with a cloud communication interface enables the patient (e.g., the individual wearing the sensor control device 110) to wear the sensor control device 110 at the direction of a medical professional while the data obtained by the sensor control device 110, operating information and other information provided by the sensor control device 110 is not displayed or otherwise communicated to the patient in real time (a so-called "blinded mode"). For example, in a "blinded" mode, the medical professional can wish to record real-time analyte levels from the user over a "wear period," which can be an extended period of time (e.g., one week or more), without having the actions or activities of the patient altered or affected by presentation of the data obtained or related notifications. The sensor control device 110 can connect to the remote cloud server 150, e.g., via cellular networks, without relying on expensive intermediary device hardware (e.g., an additional user device), and thus the medical professional can receive real-time updates to the user's analytes (or any other information recorded and transmitted by the sensor control device 110) without needing to ensure that the user has access to an intermediary device.

In some systems operating in a blinded mode, the medical professional can be unable to obtain the medical data until the completion of the blinded operation to receive data for their patient. For example, in such systems, the medical professional can be unable to obtain the medical data until the patient returns to the medical professional's offices, or returns the sensor control device 110 to the medical professional's offices, to process the medical data from sensor control device 110. In contrast, using techniques described herein, the medical professional can monitor the status of the patient in real-time while the user remains blinded to the data, and thus can review the data and/or make a diagnosis remotely during the wear period and/or prior to the patient returning to the medical professional's office. The medical monitoring system 100 described herein can also support the use of a hybrid "blinded mode" in which ordinary information provided by the sensor control device 110 is not communicated to the patient, but the patient and/or medical professional are alerted upon detection of medical events such as a dangerous levels of the analyte. In the event that sensor control device 110 disconnected from the medical monitoring system 100 and was incapable of delivering the data in real-time, the patient can be encouraged to return to an area with cellular network coverage or can physically return the sensor to the medical professional (e.g., visiting the office or sending by mail).

Additionally, using the medical monitoring system 100 with a cloud communication interface, the patient can purchase sensors 100 individually or on a subscription basis. The cost of the subscription can be based also on accessing the medical monitoring system 100 with a cloud communication interface. Varying levels of subscription plans can dictate factors such as the type of the sensor (e.g., the types of analytes monitored by the sensor control device 110), the type of access provided to the patient (e.g., how the patient receives their data and whether the patient can access historical data or only data from the current sensor), the number of devices that can be used to review the patient's data (e.g., only a single dedicated data receiving device 120, multiple dedicated data receiving devices 120, only a user device 140, multiple user devices 140), the number of individual accounts that can be used to monitoring the patient's data (e.g., the patient, the patient and one or more authorized users, etc.), and other features that would be relevant to monitoring and enhancing understanding of the patient's health through analyte monitoring. When sensor control device 110 are required to be replaced, assuming the patient's subscription is active, a new sensor control device 110 can be delivered to the patient without additional effort.

Figure 7:
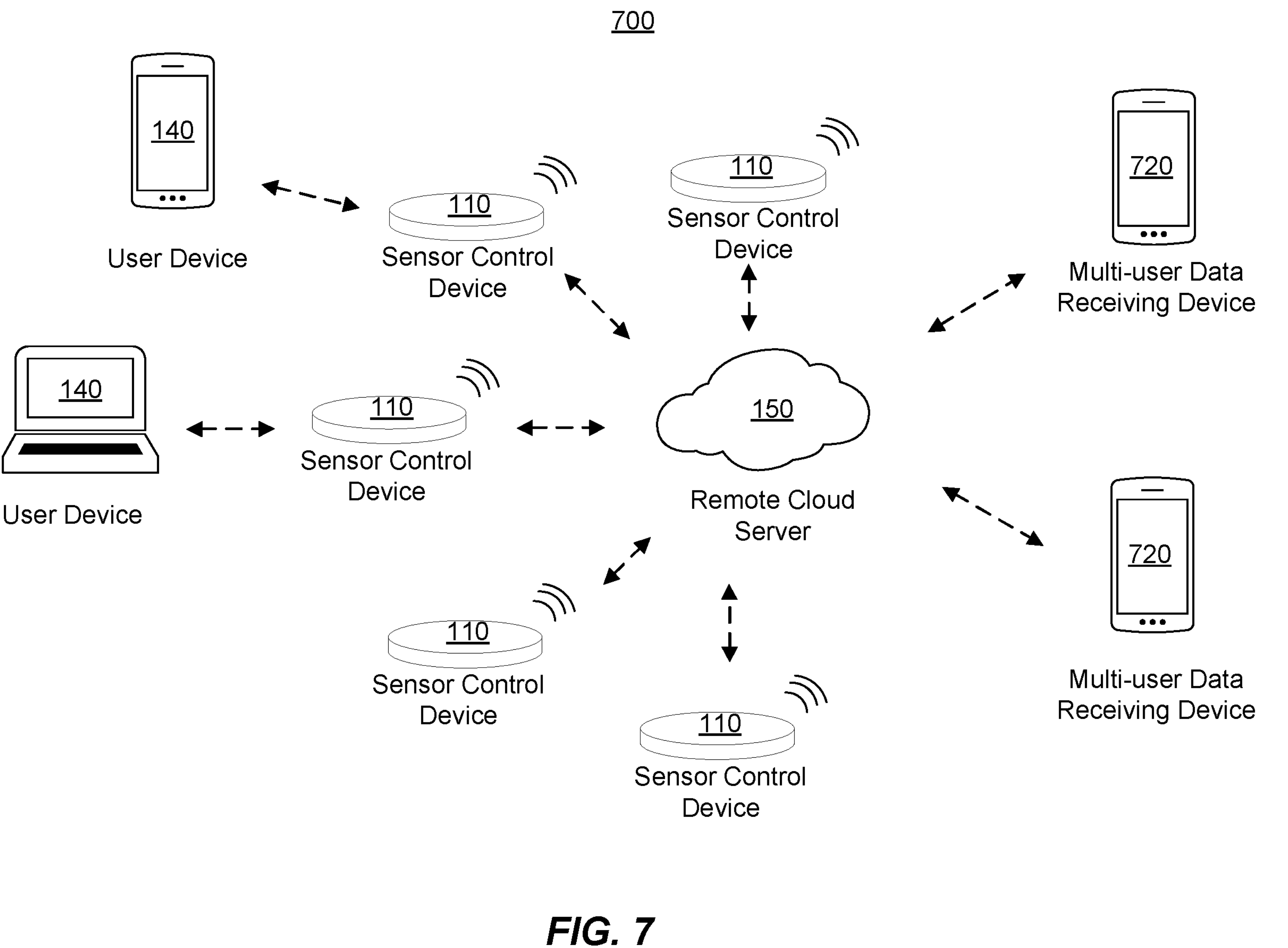
FIG. 7 is a diagram illustrating an operating environment of an example medical monitoring system capable of embodying the techniques described herein.

Another embodiment of the medical monitoring system 100 with a cloud communication interface facilitates a single user receiving medical data and updates from multiple sensors 110 that are providing medical data from multiple patients simultaneously. FIG. 7 illustrates an example operating environment of an example medical monitoring system 700 capable of embodying the techniques described herein in which a multi-user data receiving device 720 receiving medical data from multiple sensors 110. Such an embodiment can be used, for example, in a hospital or clinic where a multi-user data reeving receiving device 720 (e.g., a dedicated data receiving device 120) can easily access and receive data for multiple patients. Each sensor control device 110 can be configured to provide medical data updates directly to a cloud server 150, and as such, challenges to synchronize data between multiple intermediary data receiving devices before distribution can be avoided.

Some systems including an intermediary device for each sensor can involve pairing the intermediary device with an individual sensor and communicating with the sensor to receive data. Such an intermediary device can typically perform some on-device processing before either providing the results of the processing for display or potentially uploading the data to other devices such as a cloud server from which the data can be later retrieved. Use of such systems can involve careful management of intermediary devices, including for example in settings where many patients can be interacting or a limited number of caregivers and medical professionals can be overseeing multiple patients at the same time. If paired intermediary devices were accidentally taken out of range of the paired sensor, the intermediary device can be prevented from receiving data, which can prevent analysis and display of the data on the intermediary device, but also can prevent the intermediary device from reaching the other devices for wider distribution.

According to techniques described herein, a single multi-user data receiving device 720 can easily access data from multiple sensors 110 at least in part because the sensors 110 do not involve an intermediary device to facilitate the data being uploaded to the cloud server 150. Each sensor control device 110 first provides the data to the remote cloud server 150 which can distribute medical data and alerts to the appropriate data receiving device(s) 720. Therefore, in, for example, a hospital setting, a single data receiving device 720 can be used to monitor the status of all patients using the sensor control device 110 in a wing, floor, or other unit. For security and privacy purposes, the data receiving device can be registered and authenticated for each of the sensors 110 before data and alerts are provided. Additionally or alternatively, a data receiving device 720 can be made aware of all monitored sensors 110 or nearby sensor control device 110. A user of the data receiving device 720 (e.g., a nurse) would then be prompted to provide proof of authorization to review data from a monitored sensor control device 110 (e.g., by entering a username and/or password, by using a proximity card or NFC device to authenticate access, etc.). Because a relatively small number of data receiving devices 720 can be used to monitor a nearly limitless number of patient sensors 110, the use of techniques herein can contribute to the effective management of costs for these types of settings. Additionally, the ruggedized and longevity-focused design can help dedicated data receiving devices 120 survive the rigors of use in high intensity environments such as hospitals, further helping to control costs.

In addition to using a so-called "public" remote cloud server 150 associated with medical monitoring system 100, particular embodiments of the medical monitoring system 100 can support the use of "private" servers for larger institutions that provide the same kinds of services as the remote cloud server 150 described herein. Private servers can be particularly useful in scenarios where it is considered less desirable for patient data to be sent on commercial cellular networks, but the advantages of the sensors 110 with a cloud communication interface are still desired. For example, a hospital system can establish its own cellular network that is only accessible when on hospital grounds. A server can be installed at the hospital to perform the same functions as the remote cloud server 150. Activated sensors 110 can automatically connect to the private cellular network provided by the hospital system while patients are in the hospital. However, medical data from the sensors 110 can reach the private server before distribution to multi-user data receiving devices 720 (e.g., also located within the hospital). The private servers can also be networked across multiple locations, such that a hospital system or other medical provider having multiple locations can securely share data about patients with similar convenience.

As described herein, to support a dedicated data receiving device 120 serving as a monitoring hub or multi-user data received device 720 for medical data from multiple sensors 110 at the same time, the data receiving device can be authenticated for each sensor control device 110. When activating a new sensor control device 110, the same authentication techniques as previously described can be appropriate. In additional embodiments, authentication can involve pairing an already active sensor control device 110 with a multi-user data receiving device 720.

Numerous techniques can be used to facilitate multi-device authentication. First, a user of the multi-user data receiving device (e.g., a nurse) can identify and enter a UID associated with the active sensor. For example, the sensor control device 110 can include the UID printed or otherwise fixed to the sensor control device 110. The multi-user data receiving device can include an interface method by which the nurse enters the UID (e.g., physical or virtual keyboard to enter an alphanumeric UID, camera and scanner to enter a machine-readable UID, etc.). The UID is sent the remote cloud server 150. The remote cloud server 150 identifies a user profile associated with the UID and recognizes the request to add an authorized device. Based on preferences associated with the user profile, the remote cloud server 150 can send an authentication request to the user, e.g., using another registered device such as the user's personal dedicated data receiving device 120 or another user device 140. The user assents to the sharing of medical data and the remote cloud server 150 grants access to the multi-user data receiving device and begins sending data and notifications.

Additionally or alternatively, the multi-user data receiving device 720 and sensor control device 110 can include a close-contact input method where physical access to the device is required to activate the close-contact input. For example, the multi-user data receiving device 720 can include a button, light sensor, microphone or other similar input. As described herein, the sensor control device 110 can include a variety of similar inputs. To begin the authentication process, the close-contact input on the sensor control device 110 is actuated. This sends a signal to the ASIC 200 or other processing core of the sensor control device 110. In response, the sensor control device 110 sends a notification to the remote cloud server 150 indicating that the close-contact input has been activated. As described above, the close-contact input can be used for a variety of purposes depending on the context. The remote cloud server 150 evaluates the context and performs the appropriate action. In this case, the multi-user data receiving device 720 is instructed to send a signal to the remote cloud server 150 that includes a pairing or authentication request. This can be done through a user interface of the multi-user receiving device or by activation of the close-contact input of the multi-user data receiving device 720. The remote cloud server 150 evaluates the context of the authentication request from the multi-user device and the signal from the sensor control device 110. For example, the remote cloud server 150 can evaluate a time associated with the authentication request and signal and a location associated with the authentication request and signal. The remote cloud server 150 can also identify the networks used to deliver each of the authentication request and signal or users already associated with each. Based on the context, the remote cloud server 150 determines that the signal received from the sensor control device 110 was an authentication request and pairs the request with the authentication request from the multi-user data receiving device 720. In some embodiments, the remote cloud server 150 proceeds to allow the multi-user data receiving device 720 to access medical data reported by the sensor control device 110, which can include only medical data going forward from the authentication request as well as historical data. In other embodiments, the remote cloud server 150 sends an authentication confirmation to the patient, for example a notification pushed to the user's personal dedicated data receiving device 120, another user device 140, or via a backup communication channel (e.g., email or SMS).

Additionally or alternatively, the multi-user data receiving device 720 and sensor control device 110 can include short-range communication modules to facilitate a direct pairing between the device. For example, the multi-user data receiving device 720 and sensor control device 110 can each include NFC modules which require the devices to be in close proximity to be activated and communicate. This enables communication over the short-range communication module to act as a form of verifying physical access to both devices simultaneously. As an example, and as described herein, an NFC module can be included in the sensor control device 110 that is capable of receiving power through and NFC signal sent by the multi-user data receiving device 720. Once powered, the NFC module sends a signal to the ASIC 200 or other processing core of the sensor control device 110. The sensor control device 110 can send a signal to the remote cloud server 150 and proceed as described to verify and grant access to the multi-user data receiving device 720. Alternatively, once activated, the NFC module 243 (or other short-range communication module, such as a BLE module configured for short-range operation) of the sensor control device 110 and the NFC module 343 (or other short-range communication module) of the multi-user data receiving device 720 can initiate an exchange of information to speed up authentication by the remote cloud server 150. For example, the multi-user data receiving device 720 can provide an identifier, which can be unique to the multi-user data receiving device 720 and/or to the particular authentication exchange, to the sensor control device 110. The sensor control device 110 can then include this identifier in an affirmative authentication request to the remote cloud server 150. Similarly, the sensor control device 110 can provide an identifier, which can be unique to the sensor control device 110 and/or to the particular authentication exchange, to the multi-user data receiving device 720. The multi-user data receiving device 720 can include the identifier in an authentication request to the remote cloud server 150. Because each device can affirmatively identify the device to which it is sought to be paired, this can reduce the need for the remote cloud server 150 to rely on contextual information to identify the requests and identify a correspondence between the requests.

Once the multi-user data receiving device 720 is authenticated to receive data from multiple sensors 110, the multi-user data receiving device 720 can provide a variety of user interfaces to facilitate the review of medical data from each sensor control device 110. For example, the multi-user data receiving device 720 can show summary data from each device on a single user interface. The multi-user data receiving device 720 can be instructed to show detailed information, including historical information, for a particular device. The multi-user data receiving device 720 can request authentication or evidence of authorization to review summary or detailed information from a sensor control device 110 from the user of the multi-user data receiving device 720. The user can enter the requested information (e.g., a username and/or password, activation of a proximity card, NFC-enabled device, magnetic swipe card, etc.) before it is shown. Access can be granted only to specific users, even among shared multi-user devices 720. The multi-user data receiving device 720 can also show alerts or notifications for each of the authenticated sensors 110. The multi-user data receiving device 720 can also include user interfaces to customize or add notes to the displays of the authenticated sensors 110 that can facilitate a medical professional to easily identify the patient from whom the sensor control device 110 is providing data. For example, a user of the multi-user data receiving device 720 can indicate the name, identification, or room number of the patient, which can reduce confusion when responding to urgent events.

Some patients can desire to only temporarily authorize another user to accessing medical data from a sensor control device 110 and/or receive notifications regarding the medical data at a multi-user data receiving device 720. Therefore, as embodied herein, the medical monitoring system 100 can support manually and automatically revoking permission to access medical data and alerts. First, as described herein, sensors 110 of the type described for use with the medical monitoring system 100 can have a predefined active use period or wear period (e.g., 1 week, two weeks, 1 months, etc.). Sensors capable of use within the medical monitoring system 100 with a cloud communication interface can also have varying active use time periods, with those intended for at home use having a longer use (and an associated higher cost) than those intended for use in settings where multi-user monitoring are common (e.g., hospitals). In granting authorization to access medical data from a sensor 100, a patient can specify, and/or the medical monitoring system 100 can default to, only granting access to medical data (and alerts) from a particular sensor, historical medical data, or a specified combination thereof. At the expiration of the lifecycle of said sensor 100, access for the multi-user data receiving device 720 can be automatically revoked. A patient can further specify a particular timeframe for access to medical data from the sensor control device 110, such as where the patient has recently activated an at-home sensor control device 110 and does not need to activate a new one for use in the multi-user environment. For example, the patient can authorize medical data for the sensor control device 110 to be accessible via the multi-user data receiving device 720 for a day or even a few hours. This authorization can also be adjusted by the patient, such as through a user device 140 or personal dedicated data receiving device 120. A patient can further specify or schedule a timeframe for access independent of a lifecycle of a particular sensor control device 110, for example, a multi-user data receiving device 720 associated with a school nurse can be granted access during school hours and while school is in session, regardless of the particular sensor control device 110 that is activated. In this manner, patient privacy and convenience can be balanced using the medical monitoring system 100.

Although these embodiments have been described in the context of a hospital setting, it will be appreciated that the multi-user data receiving device 720 can be useful in a number of contexts where sensors 110 with a cloud communication interface are used to monitor medical data. For example, a nurse or other medical professional associated with a school can monitor medical data (e.g., analyte levels) of select students at the school. The nurse can then take proactive measures to prevent medical emergencies by monitoring the trending patterns of the medical data, even at a time when the student is distracted. As another example, a single user (e.g., a parent or guardian) of a family with multiple individuals wearing sensor control device 110 can monitor medical data of the individuals in the family. The individual can receive notification and/or take proactive measures on behalf of the members of the family. As another example, a user authorized on behalf of a medical professional can monitor the medical data of multiple clients to provide coaching services related to a managing, for example healthy analyte levels. The user can provide recommendations, e.g., of behavioral or dietary adjustments, to the monitored users. As another example, a coach of an athletic team can monitor medical data of multiple athletes while the athletes are competing and are not otherwise able to receive alerts or monitor their own data.

Another embodiment of the medical monitoring system 100 with a cloud communication interface enables the patient (e.g., the individual wearing the sensor control device 110) to wear the sensor control device 110 to provide automatic updates of the patient's status and physiological signals. Because the sensor control device 110 is configured to automatically communicate with a remote cloud server 150, sensor control device 110 can be used to provide information about the general well-being of the patient to persons monitoring the patient remotely, even if the patient is currently or can be in an environment where the communication infrastructure would not ordinarily facilitate continuous or periodic reporting by the patient manually. As an example, the patient can be travelling to a region where the patient does not have access to a full-featured user device 140 through which to upload data from the sensor control device 110. As another example, the patient can be otherwise occupied and not have the time or spare attention to ensure that their data is being uploaded through an intermediary device. This can include patients traveling in remote or dangerous regions or performing dangerous activities (e.g., military operations, mountain climbing, jungle traversal, etc.). Therefore, the direct-to-cloud approach to data delivery by the sensor control device 110 can facilitate the patient automatically providing status information to other user's monitoring the patient's condition as long as the sensor control device 110 is within communicative range of a cellular network or other suitably configured network boosting device.

As the data collected by the sensor control device 110 and exchanged between the sensor control device 110 and data receiving device pertain to medical information about a user, the data is highly sensitive and can be beneficial to be protected. Medical data associated with a patient is sensitive data at least in part because this information can be used for a variety of purposes, including for health monitoring and medication dosing decisions. In addition to patient data, the medical monitoring system 100 with a cloud communication interface can enforce security hardening against efforts by outside parties to reverse-engineering. The security architecture described herein can include various combinations of control features described herein, including, but not limited to the protection of communication between devices, the protection of intellectual property within components and applications, and the protection of secrets and primary keying material. As embodied herein, encryption and authentication can be used as two of the primary technical controls for providing protective features. As embodied herein, the various components of the medical monitoring system 100 with a cloud communication interface can be configured compliant with a security interface designed to protect the Confidentiality, Integrity and Availability ("CIA") of this communication and associated data. To address these CIA concerns, security functions can be incorporated into the design of the hardware and software of the medical monitoring system 100 with a cloud communication interface.

As embodied herein, to facilitate the confidentiality of data, communication connections between any two devices (e.g., a sensor control device 110 and remote cloud server 150) can be mutually authenticated prior to transmitting sensitive data by either device. Communication connections can be encrypted using a device-unique or session-unique encryption key. As embodied herein, the encryption parameters can be configured to change with every data block of the communication.

As embodied herein, to guarantee the integrity of data, encrypted communications between any two devices (e.g., a sensor control device 110 and remote cloud server 150) can be verified with transmission integrity checks built into the communications. As embodied herein, session key information, which can be used to encrypt the communication, can be exchanged between two devices after the devices have each been authenticated. Encrypted communications between a sensor control device 110 and a remote cloud server 150 can be validated with an error detection code or error correction code, including as an example and not by way of limitation, non-secure error-detecting codes, minimum distance coding, repetition codes, parity bits, checksums, cyclic redundancy checks, cryptographic hash functions, error correction codes, and other suitable methods for detecting the presence of an error in a digital message.

As embodied herein, minimum distance coding includes a random-error correcting code that provides a strict guarantee on number of detectable errors. Minimum distance coding involves choosing a codeword to represent a received value that minimizes the Hamming distance between the value and the representation. Minimum distance coding, or nearest neighbor coding, can be assisted using a standard array. Minimum distance coding is considered useful where the probability that an error occurs is independent of the position of a given symbol and errors can be considered independent events. These assumptions can be particularly applicable for transmissions over a binary symmetric channel.

Additionally or alternatively, as embodied herein, a repetition code relates to a coding scheme that repeats bits across a channel to guarantee that communication messages are received error-free. Given a stream of data to be transmitted, the data divided into blocks of bits. Each block is transmitted and re-transmitted some predetermined number of times. An error is detected if any transmission of the repeated block differs.

In addition, or as a further alternative, as embodied herein, a checksum is a value relative to a message based on a modular arithmetic sum of message code words of a fixed word length. The checksum can be directed from the entire message or a block of the message. Checksums are generated using a checksum function or cryptographic hash function that is configured to output significantly different checksum values (or hash values) for minor changes to the targeted message. A parity bit is a bit added to a group of bits in transmission to ensure that the counted number of certain bits in the outcome is even or odd. For example, the parity bit can be used to ensure that the number of bits with value 0 is odd. A parity bit can then detect single errors or a repeating fixed number of errors. A parity bit can be considered a special case of a checksum.

As embodied herein, to further reduce the risk of compromise of individual devices and the medical monitoring system 100 with a cloud communication interface, root keys (e.g., keys used to generate device-unique or session-unique keys) can optionally not be stored on the sensor control device 110 and can be encrypted in storage by the remote cloud server 150 or on other device having more computing power than the sensor control device 110 (e.g., dedicated data receiving device 120). As embodied herein, the root keys can be stored in an obfuscated manner to prevent a third-party from easily accessing the root keys. The root keys can also be stored in different states of encryption based on where in the storage they are stored. As an example, the root keys can be stored in an unencrypted form in areas of the memory that are inaccessible to third-parties (e.g., because of other read- and write-locking mechanisms).

As embodied herein, to facilitate the availability of data, sensor control device 110 operations can be protected from tampering during service life, in which the sensor control device 110 can be designed as disposable, by restricting access to write functions to the memory 220 via a communication interface (e.g., BLE and NFC). Access to read functions of the memory 220 can also be enforced, especially where the read function attempts to access particular areas of the memory 220 that have been designated secure or sensitive. The sensor control device 110 can further shut down any communication connection request that does not complete authentication within a specified amount of time to safeguard against specific denial of service attacks on the communication interface including attempted man-in-the-middle (MITM) style attacks. Furthermore, the general authentication and encryption design, described herein, can support interoperable usage where sensor control device 110 data can be made available to other "trusted" data receiving devices without being permanently bound to a single device.

As embodied herein, the devices, including sensor control device 110 and dedicated data receiving device 120, can each employ a variety of security practices to ensure the confidentiality of data exchanged over communication sessions and facilitate the relevant devices to find and establish connections with trusted endpoints. As an example, the sensor control device 110 can be configured to proactively identify and connect with trusted cellular networks and continuously verify the integrity of those connections. The sensor control device 110 can further deny and shut down connection requests if the requestor cannot complete a proprietary login procedure over a communication interface within a predetermined period of time (e.g., within four seconds). These characteristics safeguard against specific denial of service attacks.

As embodied herein, the sensor control device 110 and dedicated data receiving device 120 can support establishing long-term connection pairs by storing encryption and authentication keys associated with particular remote cloud server 150, network paths to the remote cloud servers, etc. For example, the sensor control device 110 or data receiving device can associate a connection identifier with encryption and authentication keys used to establish the connection to the remote cloud server 150 or another device when used in backup communication. In so doing, the devices can re-establish dropped connections more quickly, at least in part because the devices can avoid establishing a new authentication pairing and can proceed directly to exchanging information via encrypted communication protocols. After a connection is successfully established, the device can refrain from broadcasting connection identifiers and other information to establish a new connection and can communicate using an agreed channel-hopping scheme to reduce the opportunity for third-parties to listen to the communication.

Communication transmission integrity can be actively managed using on-chip hardware functions. While encryption provides a secure means of transmitting data in a tamper-proof manner, encryption and decryption are computationally expensive processes. Furthermore, transmission failures cannot be differentiated from attacks. As described previously, a fast, hardware-based error detection code can be used for transmission integrity. As an example, as embodied herein, an appropriately-sized error detection code for the length of the message (e.g., a 16-bit CRC) can be used, although this disclosure anticipates other suitable hardware-based error detection codes. Functions involving additional security rely on encryption.

As embodied herein, the low-power medical monitoring system 100 can employ periodic key rotation to further reduce the likelihood of key compromise and exploitation. a key rotation strategy employed by the medical monitoring system 100 with a cloud communication interface can be designed to ensure backward compatibility of field-deployed or distributed devices. As an example, the medical monitoring system 100 with a cloud communication interface can employ keys for downstream devices (e.g., devices that are in the field or cannot be feasibly provided updates) that are designed to be compatible with multiple generations of keys used by upstream devices. Rotation of keys can begin with the manufacturer or operator of the medical monitoring system 100 with a cloud communication interface. During manufacture of a new key generation of sensors 110, the manufacturer can propagate the new generation of keys to newly manufactured sensors 110. The manufacturer can also push updates to deployed devices in communication with the remote cloud server 150. As a further alternative, key rotation can be based on an agreed-upon schedule, where the devices are configured to adjust the keys used according to some time- or event-driven function.

As embodied herein, the encryption scheme described herein can involve several functions related to, for example, cryptographic performance. One class of these functions include symmetric encryption functions so that the same key can be used to encrypt outbound data and decrypt inbound data. Included in this class of functions can be block ciphers or related families of functions. A block cipher refers to an encryption function that applies a deterministic algorithm with a known key to encrypt a block of values, rather than encrypting one bit at a time as in stream ciphers. A block cipher can be particularly useful in the system architecture of the medical monitoring system 100 with a cloud communication interface because, as described previously, the sensor control device 110 (and to a lesser extent, the dedicated data receiving device 120) can have less available computing power due at least in part to design options selected to control cost, reduce size, and preserve battery life. However, stream cipher algorithms can be used according to the techniques disclosed herein with appropriate modifications to account for power and computing resources restrictions of this system architecture. Encryption algorithms that can be used include any suitable cipher techniques.

As an example, the medical monitoring system 100 with a cloud communication interface can support a first, lightweight block cipher or stream cipher for cryptography. As another example, the medical monitoring system 100 with a cloud communication interface can further support additional, more cryptographically complex, block ciphers or stream ciphers for cryptography. In particular embodiments, the first, lightweight block cipher or stream cipher can be preferentially used for devices having less access to power and computing potential, while a second block cipher or stream cipher can be a more cryptographically complex block cipher or stream cipher for use by devices with fewer restrictions on power and computing resources. The first block cipher or stream cipher can be chosen for implementations where the volume of data produced and transmitted is relatively small, rendering the more complex cryptography of the second block cipher or stream cipher unsuitable or impractical. The first block cipher or stream cipher can therefore be referred to as a lightweight block cipher or lightweight stream cipher in comparison to the second block cipher or stream cipher. The low-power medical monitoring system 100 can support the use of additional block ciphers and stream ciphers as appropriate. Each of the block ciphers and stream ciphers can be performed by software modules or dedicated hardware modules.

As an example, a lightweight block cipher can employ an add-rotate-xor ("ARX") framework. In this example, no schedule key is used. Given the data to be encrypted and key, each split into at least four blocks, the algorithm begins xoring each block of the data with the corresponding block of the key. The algorithm proceeds through a predetermined number of rounds of a permutation function, with the number of rounds being chosen to balance security and performance. Each round of the permutation function can include the following the operations performed in order: add the second block of data to the first block of data; rotate the second block a predetermined amount; xor the first block to data to the second block of data; rotate the first block of data a predetermined amount; add the fourth block of data to the third block of data; rotate the third block of data a predetermined amount; xor the third block of data to the fourth block of data; add the fourth block of data to the first block of data; rotate the fourth block of data a predetermined amount; xor the first block of data to the fourth block of data; add the second block of data to the third block of data; rotate the second block of data a predetermined amount; xor the third block of data to the second block of data; and rotate the third block of data a predetermined amount. As a final step, after the predetermined number of rounds, the algorithm again xors each block of the data in the current state with the corresponding block of the key.

As another example, a lightweight block cipher can employ an ARX algorithm. Given the block to be used with the cipher split into two words and a key, the algorithm can progress for a predetermined number of rounds. During each round, the bits of the first word of the block are rotated by a first predetermined amount, the second word of the block is added to the first word of the block, the key is xored into the first word of the block, the bits of the second word of the block are rotated by a second predetermined amount, and the first word of the block is xored into the second word of the block. As embodied herein, the keys used for each round can be computed on-demand or pre-cached depending on available computing resources.

As another example, a lightweight stream cipher can make use of xor, 32-bit addition, and constant-distance rotation. The cipher can be represented by an internal state including sixteen words arranged as a square matrix. The words include four predetermined words, eight words of key, two words of stream position, and two words of nonce. The cipher operates by performing four quarter-round operations per round, with rounds alternating by operations on the rows or columns of the internal slate. The quarter-round operations performed per round receive as input four words and perform a set series of xor, addition, and rotation operations on the input words. In a first example, the quarter-round operations follow the pattern: the addition of the first and four words are rotated by a predetermined amount and xored with the second word; the addition of the first word and second word is rotated by a predetermined amount and xored with the third word; the addition of the second word and third word is rotated by a predetermined amount and xored with the fourth word; and the addition of the third word and the fourth word is rotated by a predetermined amount and xored with the first word. The predetermined amounts can vary for each operation. After a set number of rounds, the mixed array is added to the original internal slate to prevent recovery of the initial key. A variant of the stream cipher can involve a rearranged internal slate and variations on the quarter-round operations. The quarter operations can be modified to still receive four input words, with the quarter-round operations following the pattern: the second word is added to the first word; the resulting first word is xored with the fourth word; the result is rotated by a predetermined amount; the new fourth word is added to the third word; the resulting third word is xored with the second word; the result is rotated by a predetermined amount. This pattern is repeated with different values for the predetermined-rotation. Each quarter-round updates each word twice. Additionally, the stream cipher can be modified so that quarter-rounds operated on the columns and diagonals instead of the columns and rows.

As an example, a more cryptographically complex block cipher can employ a predetermined number of rounds consisting of expansion, key mixing, substitution and permutation. Prior to the main set of rounds, the block can be divided into two halves, which each half being alternately processed to facilitate symmetry in encryption and decryption. During expansion, the current half-block is expanded by duplicating half of the bits in the half-block so that the block includes a set of operative bits comprising a copy of four input bits and copy of immediately adjacent bit from each side of the input bits. During the mixing step, a subkey is combined with the expanded half-block using xor—the exclusive-or operation. The subkeys are determined according to a key schedule based on the main encryption key. After the subkey has been mixed the block is divided into a number of substitution boxes. Each substitution box reduces the count of its input bits according a non-linear transformation provided by a lookup table. The bits output from the substitution step are rearranged according to a predetermined permutation. The operations to form the key schedule can involve retrieving a subset of the bits of the key, dividing the subset, performing a bitwise rotation by a predetermined amount and recombining the two halves to form the subkey.

As another example, a more cryptographically complex block cipher can be based on a substitution-permutation network. The cipher can include operations such as a key expansion step, in which round keys are derived from a cipher master key using a predefined key schedule, and an initial key addition step in which each byte of the block is xored with a byte of the round key. The operations can include a predetermined number of rounds in which one or more of the following steps occur: each byte is replaced with another byte in a non-linear substitution step according to a lookup table; selected bytes are shifted cyclically for a certain number of steps with the shift amount varying incrementally; subdivisions of the bytes are mixed through an invertible linear transformation; and the round key is xored into the resulting block.

As another example, a more cryptographically complex stream cipher can generate a pseudorandom stream of bits, or keystream, which is combined with the data to be encrypted using xor. The keystream is generated using a key-scheduling algorithm. In the key-scheduling algorithm, an internal array is initialized to the identity permutation of a predetermined length. For a set number of rounds equal to the predetermined length, an internal value is derived by adding the current value of the internal value, the value stored at the position of the internal array corresponding to the round number, and the value of the position of the key determined by performing the modulo of the round number to the length of the key. The internal value is then set to the modulo of the result of this operation and the maximum number of rounds. To end the round, values of the internal array at the positions indexed by the round number and the internal value are swapped. Once the key-scheduling algorithm has been completed, a pseudo-random generation algorithm modifies the state of the internal array and outputs a byte of the keystream. Encrypted data is achieved by xoring the output byte of the keystream with a byte of the data to be encrypted. In each iteration of the pseudo-random generation algorithm, a first internal value is incremented. A second internal value is assigned the value of the second internal value incremented by the value of the internal array at the position of the first internal value. The values of the internal array at the positions indexed by the first internal value and the second internal are swapped. The value of the keystream is then output as the value of the internal array at the position indexed by the addition of the values of the internal array at the first internal value and second internal value. To prevent index out of bounds errors, where values are used to index the internal array, a modulo can be performed between the value and the length of the internal array.

Moreover, block cipher or stream cipher implementations can be chosen based on known weaknesses or attack vectors. As an example, known attacks against a cipher can be evaluated and compared against the volume of data that can be generated, including during the entire active use life of a sensor control device 110, as a method of evaluating worst case scenarios regarding malicious third-parties. As described above, several of the keys are derived from device-unique values, and as such, including a single key or cipher reduces the potential impact. Additionally, the amount of compromised values needed to conduct a supply-chain level attack, e.g., to learn the value of root keys, significantly restricts the practicality of such attacks. As described herein, sensors 110 can use a randomly generated key and key recovery attempts can have little long-term value.

As embodied herein, the particular implementation of a cipher, e.g., the selection of block size and key size can be made based on the size of data blocks to be transmitted over the various communication interfaces supported by the communication module (e.g., communication module 240 and communication module 340). For example, as embodied herein, data blocks transmitted over NFC or BLE can be aligned on 8-byte boundaries, and a 64-bit cipher block size can be chosen. As embodied herein, the particular implementation of the cipher can be made based on desired encryption strength, leading to a change in the selection cipher block size. A stronger cipher typically involves more computational overhead and imposes additional time to decrypt data, e.g., during mutual authentication exchanges. Additionally, the cipher block size can be chosen based on the computing architecture of the microcontroller 210 of the ASIC 200 of the sensor control device 110 and the communication protocol used between the sensor control device 110 and data receiving devices. As embodied herein, the key size made be selected based on the particular memory constraints of the computing platforms used.

As discussed herein, the sensor control device 110 can be a device with restricted processing power, battery supply, and storage. The encryption techniques used by the sensor control device 110 (e.g., the cipher algorithm or the choice of implementation of the algorithm) can be selected based at least in part on these restrictions. The dedicated data receiving device 120 can be a more powerful device with fewer restrictions of this nature. Therefore, the dedicated data receiving device 120 can employ more sophisticated, computationally intense encryption techniques, such as cipher algorithms and implementations. For example, where a sensor control device 110 implements a lightweight block cipher a dedicated data receiving device 120 can implement a more complex cipher. Thus, the communication between the dedicated data receiving device 120 and the remote cloud server 150 can be considered more secure based on the advanced level of encryption used. This accords with the amount of data transmitted, as the dedicated data receiving device 120 can store and transmit greater amounts of sensitive medical data to the remote cloud server 150 over its lifetime than the sensor control device 110 would be capable of storing and transmitting. This also provides a benefit of enforcing greater levels of encryption with sensitive medical data as the data is transmitted farther from the sensor control device 110 and is at greater risk of interception or exposure.

In addition to the specific embodiments claimed below, the disclosed subject matter is also directed to other embodiments having any other possible combination of the dependent features claimed below and those disclosed above and in the attached figures. As such, the particular features disclosed herein can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Embodiments disclosed herein include:

Embodiment A. A medical monitoring system that comprises: a medical data server; and a medical sensor. The medical sensor comprises: an analyte sensor, and a cellular radio module in operable communication with the analyte sensor. The medical sensor is configured to: generate medical data indicative of levels of an analyte in a fluid of a patient using the analyte sensor; and provide the medical data to the medical data server by communicatively coupling with the medical data server via one or more cellular networks using the cellular radio module, the medical data comprising the recorded levels of the analyte.

Embodiment A may have one or more of the following additional elements in any combination: Element 1: wherein the medical sensor provides the medical data to the medical data server without user input from the patient; Element 2: wherein the medical data server is configured to: upon receiving the medical data from the medical sensor, determine an identifier for the patient based on the medical sensor; and associate the received medical data with medical data stored in association with the identifier for the patient; Element 3: further comprising a first external device; wherein the medical data server is configured to provide the medical data to the first external device via the one or more cellular networks; Element 4: wherein the medical data server is further configured to: process the medical data provided by the medical sensor; generate a notification for the patient based on analysis of the medical data provided by the medical sensor; and provide the notification to the first external device via the one or more cellular networks; Element 5: wherein the first external device is associated with a user authorized by the patient to receive the medical data; Element 6: wherein the medical data server is configured to: process the medical data provided by the medical sensor; and provide the processed medical data to another data server on behalf of the patient; Element 7: wherein the medical sensor provides the medical data to the medical data server according to one or more transmission parameters, and wherein medical sensor is further configured to: determine a network connectivity status of the cellular radio module to the one or more cellular networks; and modify the one or more transmission parameters according to the determined network connectivity status; Element 8: wherein the medical sensor further comprises a storage memory, and wherein the medical sensor is further configured to: determine that the medical sensor is temporarily unable to communicate with the medical data server via the one or more cellular networks; store the medical data in the storage memory; and subsequent to the medical sensor determining that the medical sensor is able to communicate with the medical data server again, provide the medical data stored in the storage memory to the medical data server via the one or more cellular networks; Element 9: wherein when providing the medical data stored in the storage memory to the medical data server, the medical sensor is configured to: provide a most recent recorded level of the analyte to the medical data server before providing other medical data stored in the storage memory; Element 10: wherein the medical data server is configured to: determine a location associated with the medical sensor based on the cellular networks and cellular radio module; and process the medical data provided by the medical sensor based on the determined location.

Embodiment B. A method for activating a medical sensor in a medical monitoring system, the method comprising: receiving, by a medical data server of the medical monitoring system from the medical sensor, a request to activate the medical sensor, wherein the request to activate the medical sensor comprises a first identifier; receiving by the medical data server from a first external device associated with a first user of the medical monitoring system, a request to authenticate the medical sensor for use by the first user, wherein the request to authenticate the medical sensor comprises a second identifier; determining, by the medical data server, if the first identifier corresponds to the second identifier; and if the first identifier and the second identifier correspond, authenticating the medical sensor for use by the first user.

Embodiment B may have one or more of the following additional elements in any combination: Element 11: wherein the medical sensor is communicatively coupled with the medical data server via one or more cellular networks; Element 12: wherein, after authenticating the medical sensor for use by the first user, the medical data server: receives medical data from the medical sensor; processes the medical data; and provides the processed medical data to the first external device; Element 13: wherein the medical data server receives the authentication request before the activation request; Element 14: wherein the medical data server provides an authentication confirmation to the medical sensor or first external device; Element 15: wherein the second identifier is a machine-readable identifier; Element 16: wherein the second identifier was received by the first external device from the medical sensor via a short-range communication.

Embodiment C. A method for activating a medical sensor in a medical monitoring system, the method comprising: receiving, by a medical data server of the medical monitoring system from the medical sensor, a request to activate the medical sensor, wherein the request to activate the medical sensor comprises a first context comprising a time or location associated with the request to activate the medical sensor; receiving by the medical data server from a first external device associated with a first user of the medical monitoring system, a request to authenticate the medical sensor for use by the first user, wherein the request to authenticate the medical sensor comprises a second context comprising a time or location associated with the request to authenticate the medical sensor; determining, by the medical data server, if the first context corresponds to the second context; and if the first context and the second context correspond, authenticating the medical sensor for use by the first user.

Embodiment C may have one or more of the following additional elements in any combination: Element 17: wherein the medical sensor is communicatively coupled with the medical data server via one or more cellular networks.

Embodiment D. A medical monitoring system comprising: a medical data server; a plurality of medical sensors, each medical sensor comprising a cellular radio module; and a data receiving device comprising a cellular radio module; wherein the medical data server is configured to: process medical data received from each medical sensor of the plurality of medical sensors by communicatively coupling with the medical sensor via one or more cellular networks using the cellular radio module of the medical sensor; and provide the processed medical data to the data receiving device by communicatively coupling with the data receiving device via the one or more cellular networks using the cellular radio module of the data receiving device.

Embodiment D may have one or more of the following additional elements in any combination: Element 18: wherein the medical sensor and data receiving device communicate through the medical data server via the one or more cellular broadband networks; Element 19: wherein the medical data server is further configured to: receive an identifier associated with an additional medical sensor from the data receiving device; authenticate the data receiving device for receiving medical data from the additional medical sensor; and provide processed medical data from the additional medical sensor to the data receiving device; Element 20: wherein the medical data server is further configured to: identify an external device associated with the additional medical sensor; send an authentication confirmation request to the external device associated with the additional medical sensor; and provide processed medical data from the additional medical sensor to the data receiving device upon receiving the authentication confirmation from the external device; Element 21: wherein the medical data server is further configured to: receive an authentication request from an additional medical sensor, wherein the authentication request is sent by the additional medical sensor after activation of a close-contact input of the medical sensor, and wherein the authentication request comprises a context of the authentication request; receive a pairing request from the data receiving device, wherein the pairing request comprises a context of the pairing request; and provide processed medical data from the additional medical sensor to the data receiving device upon identifying a correspondence between the authentication request and pairing request based on the context of the authentication request and the context of the pairing request; Element 22: wherein the one or more cellular broadband networks are private cellular broadband networks managed by a host of the medical monitoring system; Element 23: wherein the medical data server is further configured to: analyze the medical data received from each medical sensor of the plurality of medical sensors to identify a predetermined trend or condition in medical data associated with a first medical sensor; and provide, to the data receiving device, a notification corresponding to the identified trend or condition and identifying the first medical sensor; Element 24: wherein the medical data server is further configured to: receive one or more restrictions associated with providing processed medical data associated with a first medical sensor to the data receiving device, the restrictions comprising a location or a time period for use of the medical sensor; determine that the one or more restrictions are not satisfied; and cease to provide the processed medical data associated with the first medical sensor to the data receiving device in response to a determination that the one or more restrictions are not satisfied.

Embodiment E. A data receiving device for a medical monitoring system, the data receiving device comprising: one or more processors, a display, a cellular radio module; and one or more computer-readable non-transitory storage media in communication with the one or more processors and comprising instructions that, when executed by the one or more processors are configured to cause the data receiving device to perform operations comprising: pairing the data receiving device with a medical sensor through communication with a medical data server of the medical monitoring system using the cellular radio module; receiving medical data originating at the medical sensor from the medical data server of the medical monitoring system through communication with the medical data server using the cellular radio module; and displaying the medical data in a user interface of the display.

Embodiment E may have one or more of the following additional elements in any combination: Element 25: wherein pairing the data receiving device with the medical sensor through communication with the medical data server of the medical monitoring system using the cellular radio module comprises: receiving an identifier for the medical sensor through an input of the data receiving device; providing the identifier for the medical sensor to the medical data server of the medical monitoring system via one or more cellular networks using the cellular radio module; and receiving confirmation of the pairing from the medical data server of the medical monitoring system; Element 26: wherein the identifier is a machine-readable identifier and the input of the data receiving device is a short-range communication interface or a camera; Element 27: wherein the identifier is a human-readable identifier and the input of the data receiving device is a keyboard or a touch-screen user interface; Element 28: wherein instructions are further configured to cause the data receiving device to perform further operations comprising: analyzing the medical data to identify a predetermined trend or condition in the medical data; and displaying a notification corresponding to the identified trend or condition in the medical data in the user interface of the display; Element 29: wherein instructions are further configured to cause the data receiving device to perform further operations comprising: receiving a notification for a user of the data receiving device from the medical data server of the medical monitoring system; and displaying the notification for the user of the data receiving device received from the medical data server in the user interface of the display; Element 30: wherein the medical data comprises analyte, temperature, blood pressure, heart rate, or movement data; Element 31: wherein the analyte comprises glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, or uric acid; Element 32: wherein one or more components of the data receiving device are ruggedized to protect against accidental damage or destruction.

Embodiment F. A method for activating a data receiving device for a first user in a medical monitoring system, the method comprising: receiving, by a medical data server of the medical monitoring system from the data receiving device, a request to activate the data receiving device, wherein the request to activate the data receiving identifies the first user; sending, by the medical data server to a computing device associated with the first user, a request to authenticate the data receiving device to receive medical data associated with the first user; receiving by the medical data server from the computing device associated with the first user, confirmation of the request to authenticate the data receiving device; receiving, by the medical data server from a medical sensor associated with the first user, medical data associated with the first user; and providing, by the medical data server to the data receiving device, the medical data associated with the first user received from the medical sensor.

Embodiment F may have one or more of the following additional elements in any combination: Element 33: wherein the medical data server communicates with the medical sensor and data receiving device via one or more cellular broadband networks and respective cellular radio modules; Element 34: further comprising: prior to providing the medical data associated with the first to the data receiving device, sending, by the medical data server, an activation confirmation notification to the user device or the data receiving device.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical monitoring system comprising:

a medical data server configured to authenticate a medical sensor for use by an application executing on a first external device associated with a first user; and the medical sensor comprising a housing, the housing comprising:

a storage memory;

a glucose sensor, wherein at least a portion of the glucose sensor is configured to be in contact with a fluid under a skin of a patient, and a cellular radio module;

wherein the medical sensor is configured to:

generate medical data indicative of levels of glucose in the fluid of the patient;

provide the medical data to the medical data server by communicatively coupling with the medical data server via one or more cellular networks using the cellular radio module, the medical data comprising the levels of the glucose;

provide, subsequent to medical data server authentication of the medical sensor for use by the application executing on the first external device, the medical data to the first external device;

determine that the medical sensor is temporarily unable to communicate with the medical data server via the one or more cellular networks;

store the medical data in the storage memory; and subsequent to a determination that the medical sensor is able to communicate with the medical data server again, provide the medical data stored in the storage memory to the medical data server via the one or more cellular networks by provision of a most recent recorded level of glucose to the medical data server before provision of other medical data stored in the storage memory.

2. The medical monitoring system of claim 1, wherein the medical sensor provides the medical data to the medical data server without user input from the patient.

3. The medical monitoring system of claim 1, wherein the medical data server is configured to:

upon receiving the medical data from the medical sensor, determine an identifier for the patient based on the medical sensor; and associate the received medical data with medical data stored in association with the identifier for the patient.

4. The medical monitoring system of claim 1, wherein the medical data server is configured to provide the medical data to the first external device via the one or more cellular networks.

5. The medical monitoring system of claim 4, wherein the medical data server is further configured to:

process the medical data provided by the medical sensor;

generate a notification for the patient based on analysis of the medical data provided by the medical sensor; and provide the notification to the first external device via the one or more cellular networks.

6. The medical monitoring system of claim 4, wherein the first user is authorized by the patient to receive the medical data.

7. The medical monitoring system of claim 1, wherein the medical data server is configured to:

process the medical data provided by the medical sensor; and provide the processed medical data to another data server on behalf of the patient.

8. The medical monitoring system of claim 1, wherein the medical sensor provides the medical data to the medical data server according to one or more transmission parameters, and wherein medical sensor is further configured to:

determine a network connectivity status of the cellular radio module to the one or more cellular networks; and modify the one or more transmission parameters according to the determined network connectivity status.

9. The medical monitoring system of claim 1, wherein the medical data server is configured to:

determine a location associated with the medical sensor based on the cellular networks and cellular radio module; and process the medical data provided by the medical sensor based on the determined location.

* * * * *